US008602987B2

(12) United States Patent
Addington et al.

(10) Patent No.: US 8,602,987 B2
(45) Date of Patent: *Dec. 10, 2013

(54) TECHNIQUES FOR EVALUATING STRESS URINARY INCONTINENCE (SUI) USING INVOLUNTARY REFLEX COUGH TEST

(75) Inventors: W. Robert Addington, Melbourne Beach, FL (US); Robert E. Stephens, Parkville, MO (US); Michael M. Phelipa, Melbourne, FL (US); Mary W. Briganti, Melbourne, FL (US); Stuart P. Miller, Melbourne Beach, FL (US)

(73) Assignee: Pneumoflex Systems, LLC, Melbourne, FL (US)

( * ) Notice: Subject to any disclaimer, the term of this patent is extended or adjusted under 35 U.S.C. 154(b) by 922 days.

This patent is subject to a terminal disclaimer.

(21) Appl. No.: 12/643,251

(22) Filed: Dec. 21, 2009

(65) Prior Publication Data
US 2010/0137737 A1 Jun. 3, 2010

Related U.S. Application Data

(63) Continuation-in-part of application No. 11/550,125, filed on Oct. 17, 2006.

(60) Provisional application No. 60/727,740, filed on Oct. 18, 2005, provisional application No. 60/752,351, filed on Dec. 21, 2005, provisional application No. 61/139,649, filed on Dec. 22, 2008, provisional application No. 61/244,167, filed on Sep. 21, 2009.

(51) Int. Cl.
*A61B 5/00* (2006.01)
(52) U.S. Cl.
USPC .............. 600/301; 600/546; 600/561
(58) Field of Classification Search
None
See application file for complete search history.

(56) References Cited

U.S. PATENT DOCUMENTS

| 2,337,373 A | 12/1943 | Chernack | 138/53 |
| 2,918,893 A | 12/1959 | Norton | 116/114 |

(Continued)

FOREIGN PATENT DOCUMENTS

| EP | 0 608 593 | 8/1994 | A61B 5/20 |
| EP | 0 694 284 | 1/1996 | A61B 5/0215 |

(Continued)

OTHER PUBLICATIONS

Van Hengstum, et al. "*Effect of Positive Expiratory Pressure Mask Physiotherapy (PEP) Versus Forced Expiration Technique 9FET/PD) on Regional Lung Clearance in Chronic Bronchitis*" PubMed: Eur. Erspir. J. 1991; 4 (6): 651-4. (Abstract Only).

(Continued)

*Primary Examiner* — Bill Thomson
*Assistant Examiner* — Davin K Sands
(74) *Attorney, Agent, or Firm* — Allen, Dyer, Doppelt, Milbrath & Gilchrist, P.A.

(57) ABSTRACT

A system and method evaluates a patient for stress urinary incontinence. An involuntary reflex cough event is induced within the patient that activates the nucleus ambiguous and medial motor cell column of the patient and stimulates involuntary cough activated paraspinal muscles in the pelvis of the patient. And elecromyogram (EMG) is obtained from the involuntary cough activated paraspinal muscles and its duration determined. Any urine leakage time that occurs during the involuntary reflex cough event is identified and correlated within a processor together with the urine leakage time and EMG and duration of cough event to determine stress urinary incontinence.

25 Claims, 36 Drawing Sheets

(56) References Cited

U.S. PATENT DOCUMENTS

| | | |
|---|---|---|
| 3,286,713 A | 11/1966 | Kurtz et al. |
| 3,373,735 A | 3/1968 | Gallagher |
| 3,426,758 A | 2/1969 | Haraautuneian ............... 128/349 |
| 3,895,629 A | 7/1975 | Snyder ......................... 128/171 |
| 4,080,970 A | 3/1978 | Miller .......................... 128/350 |
| 4,214,593 A | 7/1980 | Imbruce et al. ............. 128/748 |
| 4,221,215 A | 9/1980 | Mandelbaum ............... 128/155 |
| 4,327,731 A | 5/1982 | Powell ......................... 128/287 |
| 4,613,323 A | 9/1986 | Norton et al. .................. 604/43 |
| 4,632,119 A | 12/1986 | Reichstein ................... 128/632 |
| 4,790,328 A | 12/1988 | Young ......................... 600/561 |
| 4,973,314 A | 11/1990 | Garret ......................... 604/180 |
| 4,976,261 A | 12/1990 | Gluck et al. ............. 128/207.15 |
| 5,146,916 A | 9/1992 | Catalani ................... 128/207.14 |
| 5,433,216 A | 7/1995 | Sugrue et al. ................. 128/778 |
| 5,462,539 A | 10/1995 | Herman et al. ............ 604/385.1 |
| 5,862,804 A | 1/1999 | Ketchum ..................... 128/885 |
| 5,904,656 A | 5/1999 | Addington et al. .......... 600/529 |
| 5,904,666 A | 5/1999 | Dedecker et al. .............. 604/65 |
| 5,916,153 A | 6/1999 | Rhea, Jr. ..................... 600/310 |
| 5,947,943 A | 9/1999 | Lee .............................. 604/361 |
| 5,980,507 A | 11/1999 | Fassuliotis et al. .......... 604/540 |
| 6,004,268 A | 12/1999 | Addington et al. .......... 600/300 |
| 6,056,699 A | 5/2000 | Sohn et al. .................... 600/561 |
| 6,267,729 B1 | 7/2001 | Addington et al. ........ 604/890.1 |
| 6,267,792 B1 | 7/2001 | Nagamiya et al. ............. 48/197 |
| 6,284,942 B1 | 9/2001 | Rabin .......................... 604/361 |
| 6,561,195 B2 | 5/2003 | Addington et al. .......... 128/898 |
| 6,568,397 B1 | 5/2003 | Addington et al. .......... 128/897 |
| 6,581,605 B2 | 6/2003 | Addington et al. .......... 128/897 |
| 6,602,243 B2 | 8/2003 | Noda ........................... 604/544 |
| 6,648,906 B2 | 11/2003 | Lasheras et al. ............. 607/105 |
| 6,655,376 B2 | 12/2003 | Addington et al. ...... 128/200.24 |
| 6,679,249 B2 | 1/2004 | Addington et al. ...... 128/200.14 |
| 6,863,664 B2 | 3/2005 | Wada et al. ............. 604/385.17 |
| 6,918,924 B2 | 7/2005 | Lasheras et al. ............. 607/105 |
| 7,140,370 B2 | 11/2006 | Tresnak et al. .......... 128/207.14 |
| 7,311,696 B2 | 12/2007 | Christon et al. ......... 604/385.01 |
| 7,322,359 B2 | 1/2008 | Ketchum ..................... 128/886 |
| 7,332,642 B2 | 2/2008 | Liu ............................... 604/361 |
| 7,343,915 B2 | 3/2008 | Addington et al. ...... 128/203.12 |
| 7,381,190 B2 | 6/2008 | Sugrue et al. ................ 600/561 |
| 7,794,425 B2 | 9/2010 | Gobel ...................... 604/101.05 |
| 2001/0050086 A1 | 12/2001 | Addington et al. .......... 128/898 |
| 2002/0049425 A1 | 4/2002 | Mosel et al. ................. 604/544 |
| 2002/0077680 A1 | 6/2002 | Noda ........................... 607/105 |
| 2002/0112731 A1 | 8/2002 | Ketchum ..................... 128/866 |
| 2003/0028075 A1 | 2/2003 | Ulmsten et al. ................ 600/29 |
| 2003/0078553 A1 | 4/2003 | Wada et al. .................. 604/361 |
| 2003/0114809 A1 | 6/2003 | Gagliardi et al. ............. 604/361 |
| 2003/0114835 A1 | 6/2003 | Noda ........................... 604/544 |
| 2004/0015100 A1 | 1/2004 | Schmidt ....................... 600/561 |
| 2004/0116457 A1 | 6/2004 | Ishihara et al. ............... 514/290 |
| 2004/0133067 A1 | 7/2004 | Tracey ........................... 600/29 |
| 2004/0172010 A1 | 9/2004 | Addington et al. ........ 604/890.1 |
| 2004/0181161 A1* | 9/2004 | Addington et al. .......... 600/529 |
| 2004/0267336 A1 | 12/2004 | Morrison et al. .............. 607/66 |
| 2005/0038328 A1* | 2/2005 | Stoehrer et al. .............. 600/301 |
| 2005/0059900 A1 | 3/2005 | Berger et al. ................. 600/546 |
| 2005/0065450 A1 | 3/2005 | Stuebe et al. ................. 600/547 |
| 2005/0265978 A1* | 12/2005 | Chancellor et al. ........... 424/93.7 |
| 2005/0288603 A1* | 12/2005 | Goping ......................... 600/561 |
| 2007/0123793 A1 | 5/2007 | Addington et al. .......... 600/546 |
| 2007/0185371 A1* | 8/2007 | Bortolotti ....................... 600/29 |
| 2007/0225576 A1 | 9/2007 | Brown et al. ................. 600/301 |
| 2008/0077043 A1 | 3/2008 | Malbrain et al. ............. 600/547 |
| 2008/0208151 A1 | 8/2008 | Zacharias et al. ............ 604/361 |
| 2008/0255529 A1 | 10/2008 | Christon et al. .............. 604/361 |
| 2008/0255530 A1 | 10/2008 | Christon et al. .............. 604/361 |
| 2008/0262454 A1 | 10/2008 | Christon et al. .............. 604/361 |
| 2009/0012350 A1* | 1/2009 | Tihon ............................. 600/30 |

FOREIGN PATENT DOCUMENTS

| | | | |
|---|---|---|---|
| WO | 99/53837 | 10/1999 | ............ A61B 5/08 |
| WO | 03/092495 | 11/2003 | ............ A61B 5/05 |
| WO | 2004/073516 | 9/2004 | ............ A61B 5/08 |
| WO | 2004073516 | 9/2004 | |
| WO | 2007/018963 | 2/2007 | ............ A61B 5/03 |
| WO | 2007/079271 | 7/2007 | ............ A61B 5/03 |
| WO | 2007/081626 | 7/2007 | ............ A61B 5/10 |
| WO | WO 2007079271 A2 * | 7/2007 | ............ A61B 5/03 |
| WO | WO 2007081626 A2 * | 7/2007 | ............ A61B 5/07 |
| WO | 2008/094771 | 8/2008 | ........... A61B 10/00 |

OTHER PUBLICATIONS

"*Urinary Incontinence in Women*" American Family Physician: American Family Physician vol. 62, No. 11 Dec. 1, 2000.
"*Exercising Your Pelvic Muscles*" American Family Physician: American Family Physician vol. 62, No. 11 Dec. 1, 2000.
Addington et al. "*Intra-abdominal Pressures during Voluntary and Reflex Cough*" Cough: vol. 4, 2, 30 Arpil 2008; pp. 1-9.
Azpiroz et al. "*Anorectal Functional Testing: Review of Collective Experience*" PMID: 11866256; Am. J. Gastroenterol. Feb. 2002; 97(2)L 2320-240. (Abstract Only).
Bolster et al. "*Responses of the Anterolateral Abdominal Muscles During Cough and Expiratory Threshold Loading in the Cat*" Journal of Applied Physiology 88: 1207-1214, 2000.
Brown et al. "*Prevalence of Urinary Incontinence and Associated Risk Factors in Postmenopausal Women*" Obstetrics & Gynecology: 1999: 94: 66-70.
Bump et al. "*Cigarette Smoking and Pure Genuine Stress Incontinence of Urine: A Comparison of Risk Factors and Determinants Between Smokers and Nonsmokers*" Am. J. Obstet Gynecol. Feb. 1994; 170(2): 579-82. (Abstract Only).
Bump et al. "*Valsalva Leak Point Pressures in Women With Genuine Stress Incontinence: Reproducibility, Effect of Catheter Caliber, and Correlations With Other Measures of Urethral Resistance. Continence Program for Women Research Group*" Am. J. Obstet. Gynecol. Aug. 1995; 173(2):551-7. (Abstract Only).
Carry et al. "*Intra-abdominal Pressure*" Ann. Fr. Aneshth. Ranim. 1994; 13(3): 381-99. (Abstract Only).
Chang et al. "Transrectal Sonographic Cystourethrography: Studies in Stress Urinary Incontinence" ScienceDirect-Urology; vol. 36, Issue 6, Dec. 1990, pp. 488-492. (Abstract Only).
Chiara et al. "Expiratory Muscle Strength Training in Persons With Mulitple Sclerosis Having Mild to Moderate Disability: Effect on Maximal Expiatory Pressure, Pulmonary Function, and Maximal Voluntary Cough" Arch Phys Med REhabil. vol. 87, Apr. 2006 pp. 468-473.
Ciofu et al. "*Contribution of VLPP (Valsalva Leak Point Pressure) in the Urodynamic Assessment*" Gynecol. Obstet. Fertil. Feb. 2004; 32(2): 160-3. (Abstract Only).
Cobb et al., "*Normal Intraabdominal Pressure in Healthy Adults*," Journal of Surgical Research, vol. 129, Feb. 18, 2005, pp. 231-235.
Cormier et al., "*Diagnosis of Female Bladder Outlet Obstruction and Relevance of the Parameter Area Under the Curve of Detrusor Pressure During Voiding: Preliminary Results*," Journal of Urology, May 2002, vol. 167, pp. 2083-2087.
Culligan et al. "*Urinary Incontinence in Women: Evaluation and Management*" American Family Physician, vol. 62 No. 11. Dec. 1, 2000.
Deffieux et al. "*Pelvic Floor Muscle Activity During Coughing: Altered Pattern in Women with Stress Urinary Incontinence*" ScienceDirect; Urology vol. 70, Issue 3; Sep. 2007, pp. 443-447.
Deffieux et al. "*Sacral reflexes and Urinary Incontinence in Women: New Concepts*" ScienceDirect; Annals of Physical and Rehabilitation Medicine; vol. 52, Issue 3. Apr. 2009, pp. 256-268.
Freestone et al."*Assessment of the Antitussive Efficacy of Codeine in Cough Associated with Common Cold*" PubMed: J. Pharm. Pharmacol. Oct. 1997; 49(10) 1045-1049. (Abstract Only).
Hammond et al. "*Assessment of aspiration risk in stroke patients with quantification of voluntary cough*" American Academy of Neurology. www.neurology.org 2001;56;502-506.

(56) References Cited

OTHER PUBLICATIONS

Hundley et al. "*A Multicentered Comparison of Measurements Obtained with Microtip and External Water Pressure Transducers*" PubMed: Int. Urogynecol. J. Pelvic Floor Dystfunct. Nov. 12, 2005: 1-7. (Abstract Only).

Kim et al. "*The Vesico-Urethral Pressuregram Analysis of Urethral Function Under Stress*" ScienceDirect; Journal of Biomechanics, vol. 30. Issue 1, Jan. 1997, pp. 19-25. (Abstract Only).

Kocjancic et al. "*Evaluation of Minimally Invasive Analysis System for Cough Leak Point Pressure Measurement*" PubMed: J. Uro. Sep. 2004; 172(3): 994-7. (Abstract Only).

Langdon et al. "*High Incidence of Respiratory Infections in 'Nil by Mouth' Tube-Fed Acute Ischemic Stroke Patients*" Neuroepidemiiology 2009; 32: 107-113.

Lasserson et al. "*Differences in Motor Activation of Voluntary and Reflex Cough in Humans*" PubMed: Thorax. Aug. 2006; 61(8): 699-705. (Abstract Only).

Lin et al. "*comparisons of Urodynamic Characteristics Between Female Patients with Overactive Bladder and Overactive Bladder Plus Stress Urinary Incontinence*" ScienceDirect: Urology vol. 64, Issue 5, Nov. 2004, pp. 945-949.

Lovegrove-Jones et al. "Mechanisms of Pelvic Floor Muscle Function and the Effect on the Urethra During a Cough" ScienceDirect; European Association of Urology Sep. 11, 2009.

Majoros et al. "*Value of Testing the Abdominal Leak Point Pressure in the Differential Diagnosis of Urinary Stress Incontinence*" PubMed: Orv. Hetil. Nov. 23, 2003; 144(47): 2321-5. (Abstract Only).

Man et al., "Cough Gastric Pressure and Maximum Expiratory Mouth Pressure in Humans", Am. J. Respir. Crit. Care Med. Sep. 15. 2003;168(6):714-7. Epub Jul. 11, 2003.

Martin, et al. "Systematic review and evaluation of methods of assessing urinary incontinence" Health Technology Assessment, Feb. 2006. vol. 10, No. 6.

Matthys et al. "*Objectivation of the Effect of Antitussive Agents Using Tussometry in Patients with Chronic Cough*" PubMed: Schweiz Med Wochenschr. Mar. 2, 1985; 115(9): 307-11. (Abstract Only).

McEwan, Jr. et al. "*Change in Cough Reflex after Treatment with Enalapril and Ramipril*" PubMed: BMJ. Jul. 1, 1989; 299(6690): 13-6. (Abstract Only).

Miklos, Jr. et al. "*A Critical Appraisal of the Methods of Measureing Leak-Point Pressures in Women with Stress Incontinence*" PubMed: Obstet. Gynecol. 1995 Setp; 86(3): 349-52. (Abstract Only).

Phua, et al. "*Patients with Gastro-Oesophageal Reflux Disease and Cough have Impaired Laryngopharyngeal Mechanosensitivity*" PubMed: Thorax. Jun. 2005; 60(6): 488-91. (Abstract Only).

Quek, et al. "*Morbidity and Significant Bacteriuria after Urodynamic Studies*" Annals Academy of Medicine; Singapore 2004; 33:754-7.

Richter, et al. "*Lower Urinary Tract Symptoms, Quality of Life and Pelvic Organ Prolapse: Irritative Bladder an Obstructive Voiding Symptoms in Women Planning to Undergo Abdominal Sacrocolpopexy for Advanced Pelvic Organ Prolapse*" ScienceDirect: Journal of Urology vol. 178, issue 3, Sep. 1997, pp. 965-969.

Shaker, et al. "*Vocal Cord Closure Pressure During Volitional Swallow and other Voluntary Tasks*" PubMed: Dysphagia. 2002 Winter; 17(1)L 13-8. (Abstract Only).

Shishido, et al. "*Influence of Pelvic Floor Muscle Contraction on the Profile of Vaginal Closure Pressure in Continent and Stress Urinary Incontinent Women*" ScienceDirect: Journal of Urology; vol. 179. Issue 5, May 2008, pp. 1917-1922.

Steffen, et al. "*Measurement of Pressure and Force as a Basis of the Postoperative Evaluation of Abdominal Wall Function*" PubMed: Z. Exp. Chir. Transplant. Kunstliche Organe. 1987; 20(1): 44-9. (Abstract Only).

Steier et al. "The Value of Multiple Tests of Respiratory Muscle Strength," Thorax, Jun. 8, 2007, Epub. (Abstract Only).

Swift et al. "*Test-retest Reliability of the Cough Stress Test in the Evaluation of Urinary Incontinence*" Obstetrics and Gynecology; vol. 94, No. 1, Jul. 1999; pp. 99-102.

Trabucco, et al. "Role of Proteoglycans in the Organization of Periurethral Connective Tissue in Women with Stress urinary Incontinence" ScienceDirect: Maturital; vol. 58, Issue 4, Dec. 20, 2007, pp. 395-405.

Turker, et al. "*The Presence of Transurethral Cystometry Catheter and Type of Stress Test Affect the measurement of Abdominal Leak Point Pressure (ALPP) in Women with Stress Urinary Incontinence (SUI)*" PubMed: Neurourol. Urodyn. Aug. 19, 2009. (Abstract Only).

Upadya et al., "Predictors and Consequences of Pneumonia in Critically Ill Patients With Stroke,"Journal of Critical Care, vol. 19, No. 1, Mar. 2004, pp. 16-22.

Van Hengstum, et al. "*Effect of Positive Expiratory Pressure Mask Physiotherapy (PEP) Versus Forced Expiration Technique 9FET/ PD) on Regional Lung Clearance in Chronic Bronchitics*" PubMed: Eur. Erspir. J. 1991; 4(6): 651-4. (Abstract Only).

Vernon et al. "*Measuring Cough Severity: Perspective form the Literature and From Patients with Chronic Cough*" http://www.coughjournal, 2009.

Vovk et al., "Capsaicin Exposure Elicits Complex Airway Defensive Motor Patterns in Normal Humans in a Concentration-Dependent Manner," Pulm Pharmacol Ther. 2007; 20(4):423-32, Epub, Dec. 12, 2006. (Abstract Only).

Wall, et al. "*Are Vaginal and Rectal Pressures Equivalent Approximations of One Another for the Purpose of Performing Subtracted Cystometry?*" PubMed: Obstet. Gynecol. Apr. 1995; 85(4):488-93. (Abstract Only).

Yuan, et al. "*Vibratory Perception and Female Stress urinary Incontinence*"ScienceDirect: Journal of urology Apr. 2, 2009.

Xie, et al. "*Alterations of Estrogen Receptor-a and—b in the Anterior Vaginal Wall of Women with Urinary Incontinence*"ScienceDirect: European Journal of Obstetrics & Gynecology and Reproductive Biology, vol. 134, Issue 2, Oct. 2007, pp. 254-258.

Zalm, et al. "*Diagnostic Investigation of the Pelvic Floor: a helpful Tool in the Approach in Patients with Complains of Micturition, Defecation, and/or Sexual Dysfunction*" J. Sex. Med. Apr. 2008; 5(4): 864-71. Epub Jan. 21, 2008. (Abstract Only).

Bolster et al. "*Neurogenesis of cough, other airway defensive behaviors and breathing: A holarchical system?*" Jan. 16, 2006 www.sciencedirect.com.

DeBacker"*Abdominal compartment syndrome*" http://ccforum.com. Sep. 30, 1999.

Dziewas et al. *Pneumonia in acute stroke patients fed by nasogastric tube* www.jnnp.com Sep. 10, 2003.

Irwin, Richard "*Chronic Cough Due to Gastroesophageal Reflux Disease: ACCP Evidence-Based Clinical Practice Guidelines*" http://chestjournal.chestpubs.org/content/129/1_supll/80S.full.html, 2006.

Irwin et al. "*The Cough Reflex and Its Relation to Gastroesophageal Reflux*" Am J Med. 2000;108(4A):73S-78S.

Handa et al. "*Federal Guidelines for the Management of Urinary Incontinence in the United States: Which Patients Should Undergo Urodynamic Testing?*" Int. Urogynecol J (1995) 6:198-203.

Jakus et al. "*Brainstem Areas Involved in the Aspiration Reflex: c-Fos Study in Anesthetized Cats*" Physiol. Res. 53: 703-717, 2004.

Poliacek et al. "*Cough, Expiration and Aspiration Reflexes following Kainic Acid Lesions to the Pontine Respiratory Group in Anesthetized Cats*" Physiol. Res. 53: 155-163, 2004.

Widdicombe et al. "*Supramedullary influences on cough*" Respiratory Physiology Neurobiology 152 (2006) 320-328.

Lasserson et al., "Differences in Motor Activation of Voluntary and Reflex Cough in Humans,"Thorax, Aug. 2006; 61(8):699-705. Epub, Apr. 6, 2006, Abstract Only, 2 pages.

WD. Man et al., "Cough Gastric Pressure and Maximum Expiratory Mouth Pressure in Humans", American Journal of Respiratory and Critical Care Medicine, vol. 168, 2003, 4 pages.

F. Lavorini et al., "Fog-Induced Cough with Impaired Respiratory Sensation in Cogenital Central Hypoventilation Syndrome", Am J Respir Crit Care Med., Oct. 15, 2007; 176(8):825-32. Epub Aug. 2007.

Cadiere et al. "*Antireflux Transoral Incisionless Fundoplication Using EsophyX: 12-Month Results of a Prospective Multicenter Study*" World J Surg (2008) 32:1676-1688.

(56) References Cited

OTHER PUBLICATIONS

Marino et al. "*Induction of Lower Esophageal Sphincter (LES) Dysfunction during Use of the Negative Pressure Body Ventilator*" The American Journal of Gastroenterology vol. 83, No. 12, 1988.

Jones et al. "*Mechanisms of Pelvic Floor Muscle Funciton and the Effect on the Urethra during a Cough*" www.sciencedirect.com, 2009.

Chang et al. "*An objective study of acid reflux and cough in children using an ambulatory pHmetry-cough logger*" http://adc.bmj.com/cgi/reprintform, 2010.

Mutolo et al. "*Depression of the cough reflex by microinjections of antitussive agents into the caudal ventral respiratory group of the rabbit*" J Appl Physiol (Jul. 22, 2010). Doi:10.1152/japplphysiol.00406.2010.

Yapici et al. "*The role of coughing as a gastroesophageal-reflux provoking maneuver: the scintigraphical evaluation*" DOI: 10.1097/MNM.Ob013e3283298f90, 2009.

Vizel et al. "*Validation of an ambulatory cough detection and counting application using voluntary cough under different conditions*" Http://www.coughjournal.com/content/6/1/3, 2010.

Ryan et al. "*Cough reflex sensitivity improves with speech language pathology management of refractory chronic cough*", http://www.coughhournal.com/content/6/1/5, 2010.

Smith et al. "*Spatial and Functional Architecture of the a mammalian Brain Stem Respiratory Network: A Hierarchy of Three Oscillatory Mechanisms*" J Neurophysiol 98: 3370-3387, 2007.

Rybak et al. "*Spatial organization and state-dependent mechanisms for respiratory rhythm and pattern generation*" Prog Brain Res. 2007: 165: 201-220.

Hernadez et al "*Anatomic-manometric correlation of the upper esophageal sphincter: a concurrent US and manometry study*" www.giejournal.org, 2010.

Kocjancic et al. "*Adjustable Continence Therapy for Severe Intrinsic Sphincter Deficiency and Recurrent Female Stress Urinary Incontinence: Long-Term Experience*" wwwljurology.com vol. 184, 1017-1021. Sep. 2010.

Canning et al. "*An essential component to brainstem cough gating identified in anesthetized guinea pigs*" The FASEB Journal article fj.09-151068, 2010.

Abdala et al. "*Multiple Pontomedullary mechanisms of respiratory rhythmogenesis*" Respiratory Physiology & Neurobiology 168 (2009) 19-25.

Vizel et al. "*Validation of an ambulatory cough detection and counting application using voluntary cough under different conditions*" http://www.coughjornal.com/content/6/1/3, 2010.

Satou et al. "*Gastroesophageal Reflux during Enteral Feeding in Stroke Patients: A 14-hour Esophageal pH-monitoring Study*" Journal of Stroke andCerebrovascular Diseases, 2011.

DeLancey, John *Why Do Women have Stress Urinary Incontinence?* Neurourology and Urodynamics 29:S13-S17 (2010).

Douzinal et al. "*Reasons of PEG failure to eliminate gastroesophageal reflux in mechanically ventilated patients*" wjg.whgnet.com doi:10.3748/wjg.15.5455, 2009.

Kuribayashi et al. "*Terminating motor events for TLESR are influenced by the presence and distribution of reluxate*"AM J Physiol Gastrointeres Liver Physiol 297: G71-G75 2009.

Marik, PE "*Aspiration syndromes: aspiration pneumonia and pneumonitis*" Hop PRact (minneap) Feb. 2010; 38(1): 35-42. Abstract only.

Hurt et al. *Gastric residual volumes in critical illness: what do they really mean?* Crit Care Clin. Jul. 2010; 26 (3): 481-90, viii-ix. Abstract only.

Voorham-van der et al. "*Diganotic investigation of the pelvic floor*": J Sex Med. 2008 Apri; 5 (4): 864-71. Epub Jan. 21, 2008. Abstract only.

Nicolau et al. "*Endoluminal fundoplication (ELF) with EsophyX2 for gastroesophageal reflux disease (GERD)*" Chirurgia (Bucur). Jul.-Aug. 2009; 104(4):381-7. Abstract only.

Turker et al. "*The presence of transurethral cystometry catheter and type of stress test affect the measurement of abdominal leak point pressure (ALPP) in women with stress urinary incontinence*" Neurourol Urodyn. 2010 Apri; 29(4): 536-9. Abstract only.

Lavorini et al., "Fog-Induced Cough With Impaired Respiratory Sensation in Congenital Central Hypoventilation Syndrome," American Journal of Respiratory and Critical Care Medicine, vol. 176, Aug. 2, 2007, pp. 825-832.

"GERD: For Surgeons, Gastroesophageal Reflux Disease, or Chronic Acid Reflux," http://www.endogastricsolutions.com/aboutGERD_for-surgeons.htm, Nov. 19, 2011, pp. 1-8.

\* cited by examiner

VOLUNTARY COUGH

| SUBJECT | TEST ORDER | AUC | PEAK PRESSURE (CM OF WATER) | DURATION (SEC) | NO. OF SPIKES | LEAK |
|---|---|---|---|---|---|---|
| SUBJECT #1 | VC 1ST | 92 | 87 | 3 | 2 | NO |
| SUBJECT #2 | VC 1ST | 290 | 167 | 6 | 2 | NO |
| SUBJECT #3 | RCT 1ST | 326 | 100 | 11 | 7 | NO |
| SUBJECT #4 | VC 1ST | 430 | 165 | 10 | 2 | NO |
| SUBJECT #5 | RCT 1ST | 612 | 211 | 7 | 5 | YES |
| SUBJECT #6 | RCT 1ST | 518 | 180 | 8 | 5 | YES |

FIG. 7A

INVOLUNTARY COUGH (REFLEX COUGH TEST)

| SUBJECT | TEST ORDER | AUC | PEAK PRESSURE (CM OF WATER) | DURATION (SEC) | NO. OF SPIKES | LEAK |
|---|---|---|---|---|---|---|
| SUBJECT #1 | VC 1ST | 125 | 100 | 3 | 2 | YES |
| SUBJECT #2 | VC 1ST | 963 | 175 | 23 | 10 | NO |
| SUBJECT #3 | RCT 1ST | 1276 | 170 | 27 | 11 | NO |
| SUBJECT #4 | VC 1ST | 1575 | 139 | 41 | 9 | NO |
| SUBJECT #5 | RCT 1ST | 1428 | 174 | 26 | 16 | YES |
| SUBJECT #6 | RCT 1ST | 1148 | 194 | 16 | 14 | YES |

FIG. 7B

PAIRED SAMPLES STATISTICS

|  |  | MEAN | N | STD. DEVIATION | STD. ERROR MEAN |
|---|---|---|---|---|---|
| PAIR 1 | RCTAIAP | 50.739 | 168 | 19.662 | 1.517 |
|  | VCTAIAP | 44.907 | 168 | 13.910 | 1.073 |

PAIRED SAMPLES CORRELATIONS

|  |  | N | CORRELATION | Sig. |
|---|---|---|---|---|
| PAIR 1 | RCTAIAP & VCTAIAP | 168 | .514 | .000 |

PAIRED SAMPLES TEST

|  |  | PAIRED DIFFERENCES | | | | | |
|---|---|---|---|---|---|---|---|
|  |  | | | | 95% CONFIDENCE INTERVAL OF THE DIFFERENCE | | |
|  |  | MEAN | STD. DEVIATION | STD. ERROR MEAN | LOWER | UPPER | t |
| PAIR 1 | RCTAIAP - VCTAIAP | 5.832 | 17.282 | 1.333 | 3.199 | 8.464 | 4.374 |

PAIRED SAMPLES TEST

|  |  | df | SIG. (2-TAILED) |
|---|---|---|---|
| PAIR 1 | RCTAIAP - VCTAIAP | 167 | .000 |

FIG. 11

PAIRED SAMPLES STATISTICS

| | | MEAN | N | STD. DEVIATION | STD. ERROR MEAN |
|---|---|---|---|---|---|
| PAIR 1 | RCTPIAP | 151.733 | 168 | 45.629 | 3.520 |
| | VCTPIAP | 128.937 | 168 | 37.856 | 2.921 |

PAIRED SAMPLES CORRELATIONS

| | | N | CORRELATION | Sig. |
|---|---|---|---|---|
| PAIR 1 | RCTPIAP & VCTPIAP | 168 | .630 | .000 |

PAIRED SAMPLES TEST

| | | PAIRED DIFFERENCES | | | | | |
|---|---|---|---|---|---|---|---|
| | | MEAN | STD. DEVIATION | STD. ERROR MEAN | 95% CONFIDENCE INTERVAL OF THE DIFFERENCE | | t |
| | | | | | LOWER | UPPER | |
| PAIR 1 | RCTPIAP - VCTPIAP | 22.796 | 36.603 | 2.824 | 17.221 | 28.371 | 8.072 |

PAIRED SAMPLES TEST

| | | df | SIG. (2-TAILED) |
|---|---|---|---|
| PAIR 1 | RCTPIAP - VCTPIAP | 167 | .000 |

FIG. 12

PAIRED SAMPLES STATISTICS

|  |  | MEAN | N | STD. DEVIATION | STD. ERROR MEAN |
|---|---|---|---|---|---|
| PAIR 1 | RCTAUC | 753.089 | 168 | 457.718 | 35.314 |
|  | VCTAUC | 512.101 | 168 | 298.110 | 23.000 |

PAIRED SAMPLES CORRELATIONS

|  |  | N | CORRELATION | Sig. |
|---|---|---|---|---|
| PAIR 1 | RCTAUC & VCTAUC | 168 | .289 | .000 |

PAIRED SAMPLES TEST

|  | PAIRED DIFFERENCES | | | | | t |
|---|---|---|---|---|---|---|
|  | MEAN | STD. DEVIATION | STD. ERROR MEAN | 95% CONFIDENCE INTERVAL OF THE DIFFERENCE | | |
|  |  |  |  | LOWER | UPPER |  |
| PAIR 1 RCTAUC-VCTAUC | 240.988 | 468.567 | 36.151 | 169.617 | 312.359 | 6.666 |

PAIRED SAMPLES TEST

|  | df | SIG. (2-TAILED) |
|---|---|---|
| PAIR 1 RCTAUC-VCTAUC | 167 | .000 |

FIG. 13

SUMMARY OF SENSITIVITY, SPECIFICITY, PPV, NPV (PRIMARY ANALYSES)
EFFICACY POPULATION

| STATUS | VOLUNTARY COUGH (N=180) | REFLEX COUGH (N=179) | P-VALUE |
|---|---|---|---|
| SENSITIVITY [1] | | | |
| MILD SUI | 74/140 (53) | 110/139 (79) | <.0001 |
| MODERATE/SEVERE SUI | 35/65 (54) | 51/65 (78) | 0.0145 |
|  | 39/75 (52) | 59/74 (80) | <.0001 |
| SPECIFICITY [2] | 38/40 (95) | 34/40 (85) | 0.0352 |
| 95% CI (VCT-IRCT): (-1.6, 21.6) | | | |
| POSITIVE PREDICTIVE VALUE [3] | 74/76 (97) | 110/116 (95) | |
| MILD SUI | 35/37 (95) | 51/57 (89) | |
| MODERATE/SEVERE SUI | 39/41 (95) | 59/65 (91) | |
| NEGATIVE PREDICTIVE VALUE [4] | 38/104 (37) | 34/63 (54) | |

[1] SENSITIVITY = TP/(TP+FN)
[2] SPECIFICITY = TN/(TN+FP)
[3] POSITIVE PREDICTIVE VALUE = TP/(TP+FP)
[4] NEGATIVE PREDICTIVE VALUE = TN/(TN+FN)
TN = TRUE NEGATIVE, TP = TRUE POSITIVE, FN = FALSE NEGATIVE, FP = FALSE POSITIVE,
FOR THE PRIMARY ANALYSES, LEAKAGE IS DEFINED AS A LEAK DURING A TEST WHILE IN THE SEMI-RECUMBENT POSITION.
NOTE: THE EFFICACY POPULATION IS DEFINED AS ALL SUBJECTS WHO ARE RANDOMIZED AND EXPOSED TO STUDY DRUG.
TO DETERMINE WHETHER OR NOT THERE IS A PROVOCATION EFFECT, GENERALIZED ESTIMATING EQUATIONS ASSUMING AN EXCHANGEABLE CORRELATION
MATRIX, LOGIT LINK AND BINOMIAL DISTRIBUTION WITH FIXED EFFECTS FOR TEST (VCT VS. IRCT) AND PERIOD (1 VS. 2) WERE USED.

FIG. 17A

SUMMARY OF SENSITIVITY, SPECIFICITY, PPV, NPV (PRIMARY ANALYSES)
EFFICACY POPULATION - ADJUDICATED STRATA

| STATUS | VOLUNTARY COUGH (N=180) | REFLEX COUGH (N=179) | P-VALUE |
|---|---|---|---|
| SENSITIVITY [1] | | | |
| MILD SUI | 74/148 (51) | 115/147 (78) | <.0001 |
| | 36/73 (49) | 56/73 (77) | 0.0037 |
| MODERATE/SEVERE SUI | 39/75 (52) | 59/74 (80) | <.0001 |
| SPECIFICITY [2] | 31/32 (97) | 31/32 (97) | 1.0000 |
| 95% CI (VCT-RCT): (0.0, 0.0) | | | |
| POSITIVE PREDICTIVE VALUE [3] | | | |
| MILD SUI | 75/76 (99) | 115/116 (99) | |
| | 36/37 (97) | 56/57 (98) | |
| MODERATE/SEVERE SUI | 39/40 (98) | 59/60 (98) | |
| NEGATIVE PREDICTIVE VALUE [4] | 31/104 (30) | 31/63 (49) | |

[1] SENSITIVITY = TP/(TP+FN)
[2] SPECIFICITY = TN/(TN+FP)
[3] POSITIVE PREDICTIVE VALUE = TP/(TP+FP)
[4] NEGATIVE PREDICTIVE VALUE = TN/(TN+FN)
TN = TRUE NEGATIVE, TP = TRUE POSITIVE, FN = FALSE NEGATIVE, FP = FALSE POSITIVE.
FOR THE PRIMARY ANALYSES, LEAKAGE IS DEFINED AS A LEAK DURING A TEST WHILE IN THE SEMI-RECUMBENT POSITION.
NOTE: THE EFFICACY POPULATION IS DEFINED AS ALL SUBJECTS WHO ARE RANDOMIZED AND EXPOSED TO STUDY DRUG.
TO DETERMINE WHETHER OR NOT THERE IS A PROVOCATION EFFECT, GENERALIZED ESTIMATING EQUATIONS ASSUMING AN EXCHANGEABLE CORRELATION MATRIX, LOGIT LINK AND BINOMIAL DISTRIBUTION WITH FIXED EFFECTS FOR TEST (VCT VS. RCT) AND PERIOD (1 VS. 2) WERE USED.

FIG. 17B

SUMMARY OF SENSITIVITY, SPECIFICITY, PPV, NPV (PRIMARY ANALYSES)
PER-PROTOCOL POPULATION

| STATUS | VOLUNTARY COUGH (N=172) | REFLEX COUGH (N=171) | P-VALUE |
|---|---|---|---|
| SENSITIVITY [1] | | | |
| MILD SUI | 74/140 (53) | 110/139 (79) | <.0001 |
| MODERATE/SEVERE SUI | 35/65 (54) | 51/65 (78) | 0.0145 |
|  | 39/75 (52) | 59/74 (80) | <.0001 |
| SPECIFICITY [2] | 31/32 (97) | 31/32 (97) | 1.0000 |
| 95% CI (VCT-IRCT): (0.0, 0.0) | | | |
| POSITIVE PREDICTIVE VALUE [3] | | | |
| MILD SUI | 74/75 (99) | 110/111 (99) | |
| MODERATE/SEVERE SUI | 35/36 (97) | 51/52 (98) | |
|  | 39/40 (98) | 59/60 (98) | |
| NEGATIVE PREDICTIVE VALUE [4] | 31/97 (32) | 31/60 (52) | |

[1] SENSITIVITY = TP/(TP+FN)
[2] SPECIFICITY = TN/(TN+FP)
[3] POSITIVE PREDICTIVE VALUE = TP/(TP+FP)
[4] NEGATIVE PREDICTIVE VALUE = TN/(TN+FN)
TN = TRUE NEGATIVE, TP = TRUE POSITIVE, FN = FALSE NEGATIVE, FP = FALSE POSITIVE.
FOR THE PRIMARY ANALYSES, LEAKAGE IS DEFINED AS A LEAK DURING A TEST WHILE IN THE SEMI-RECUMBENT POSITION.
NOTE: THE PER-PROTOCOL POPULATION IS DEFINED AS ALL SUBJECTS WHO ARE RANDOMIZED, EXPOSED TO STUDY DRUG AND HAVE NO MAJOR PROTOCOL VIOLATIONS
TO DETERMINE WHETHER OR NOT THERE IS A PROVOCATION EFFECT, GENERALIZED ESTIMATING EQUATIONS ASSUMING AN EXCHANGEABLE CORRELATION MATRIX, LOGIT LINK AND BINOMIAL DISTRIBUTION WITH FIXED EFFECTS FOR TEST (VCT VS. IRCT) AND PERIOD (1 VS. 2) WERE USED.

FIG. 17C

CHI-SQUARED (2x2)

| OBSERVED FREQUENCIES | | | |
|---|---|---|---|
| | COLUMN VARIABLE | | |
| ROW VARIABLE | IRCT | VCT | TOTAL |
| EARLY LEAK | 42 | 13 | 55 |
| LATE LEAK | 76 | 58 | 134 |
| TOTAL | 118 | 71 | 189 |

CALCULATIONS
fo-fe 7.661376  -7.66138
-7.66138   7.661376

| EXPECTED FREQUENCIES | | | |
|---|---|---|---|
| | COLUMN VARIABLE | | |
| ROW VARIABLE | IRCT | VCT | TOTAL |
| EARLY LEAK | 34.33862 | 20.66138 | 55 |
| LATE LEAK | 83.66138 | 50.33862 | 134 |
| TOTAL | 118 | 71 | 189 |

(fo-fe)^2/fe 1.709349  2.840889
0.701598  1.166037

| DATA | |
|---|---|
| LEVEL OF SIGNIFICANCE | 0.05 |
| NUMBER OF ROWS | 2 |
| NUMBER OF COLUMNS | 2 |
| DEGREES OF FREEDOM | 1 |

| RESULTS | |
|---|---|
| CRITICAL VALUE | 3.8415 |
| CHI-SQUARE TEST STASTISTIC | 6.4179 |
| p-VALUE | 0.0113 |
| REJECT THE NULL HYPOTHESIS | |

EXPECTED FREQUENCY ASSUMPTION IS MET.

FISHER'S EXACT TEST

| | IRCT | VCT | TOTAL |
|---|---|---|---|
| EARLY LEAK | 42 | 13 | 55 |
| LATE LEAK | 76 | 58 | 134 |
| TOTAL | 118 | 71 | 189 | p-VALUE= 0.01307        REJECT THE NULL HYPOTHESIS

FIG. 20

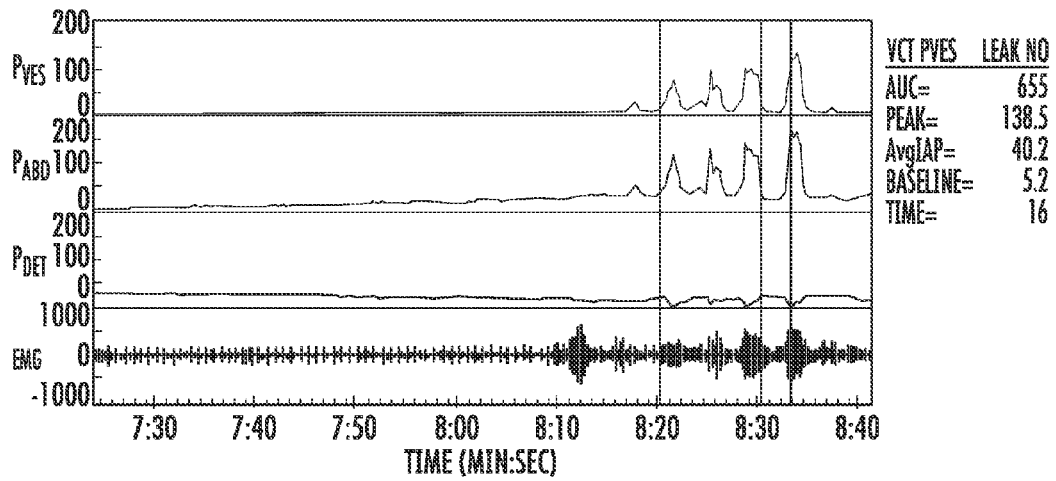
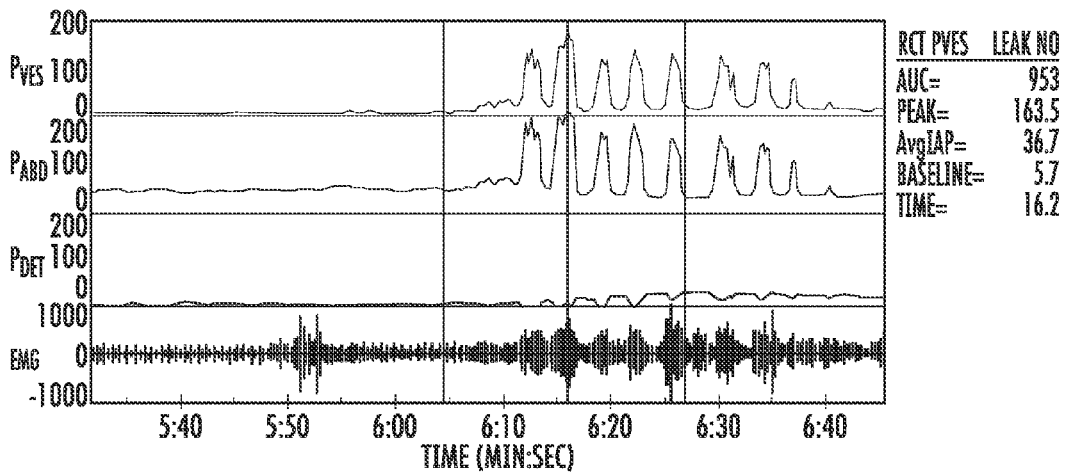
AN URODYNAMIC TRACING OF A SERIES OF FORCEFUL VC IN A FEMALE SUBJECT WHO DOES NOT HAVE A HISTORY OF SUI. THE URINARY BLADDER WAS FILLED WITH 200 ml OF SALINE AND INTRAVESICAL AND RECTAL PRESSURE CATHETERS WERE USED.
FIG. 21

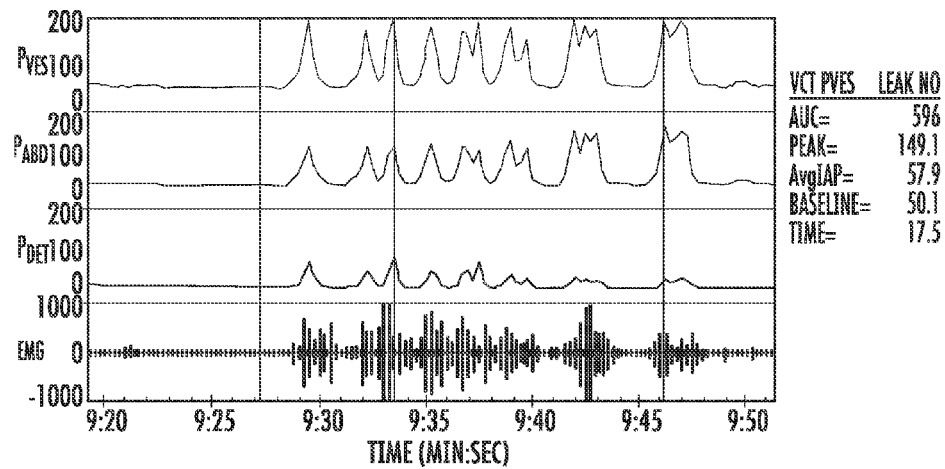
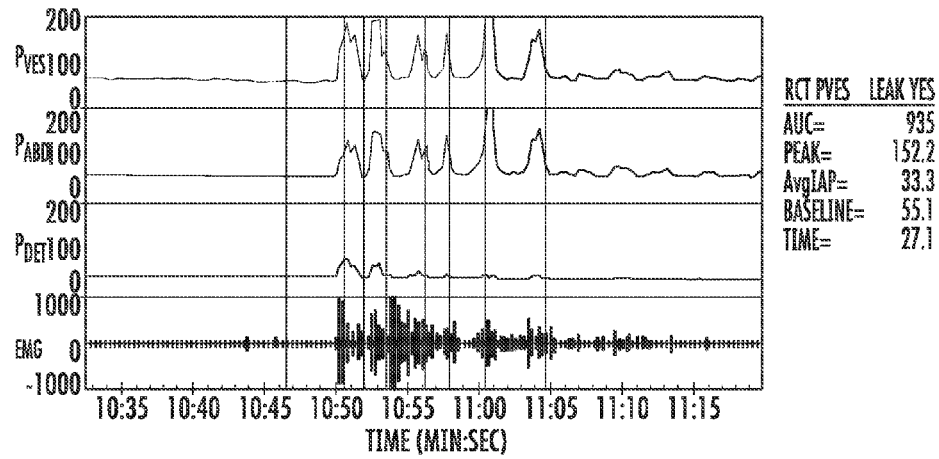
AN URODYNAMIC TRACING OF A SERIES OF FORCEFUL VC IN A FEMALE SUBJECT, WHO HAS MODERATE/SEVERE SUI. THE URINARY BLADDER WAS FILLED WITH 200 ml OF SALINE AND INTRAVESICAL AND RECTAL PRESSURE CATHETERS WERE USED. VC DID NOT ELICIT SUI DESPITE THE SERIES OF VIGOROUS INDIVIDUAL CONSECUTIVE INHALATION VC EFFORTS.
FIG. 22

TECHNIQUES FOR EVALUATING STRESS URINARY INCONTINENCE (SUI) USING INVOLUNTARY REFLEX COUGH TEST

RELATED APPLICATION(S)

This application is a continuation-in-part application of prior filed U.S. application Ser. No. 11/550,125 filed Oct. 17, 2006, which claims prior to U.S. provisional application Ser. No. 60/727,740 filed Oct. 18, 2005, U.S. provisional application Ser. No. 60/752,351 filed Dec. 21, 2005, which are all incorporated herein by reference in their entirety. This application also claims priority to prior filed U.S. provisional application Ser. No. 61/139,649 filed Dec. 22, 2008, and prior filed U.S. provisional application Ser. No. 61/244,167 filed Sep. 21, 2009, which are both incorporated herein by reference in their entirety.

FIELD OF THE INVENTION

This invention is directed to the field of medical devices and testing and, more particularly, to apparatus and techniques for evaluating urinary stress incontinence.

BACKGROUND OF THE INVENTION

According to the American Academy of Family Physicians, urinary incontinence (UI) affects approximately twelve million persons in the United States alone. Although urinary incontinence can occur in both men and women, it is most common in women over the age of 50. There are many causes of UI, including age related atrophic changes in the genitourinary anatomy in women after menopause, enlargement of the prostate in men as well as generalized weakening of the pelvic floor muscles, medication side effects, immobility, infection of the urinary tract and various underlying medical co-morbidities including diabetes and hypercalcemia.

There are four basic types of urinary incontinence; functional, overflow, urge and stress. Stress incontinence occurs when there is a sudden pressure on the lower abdominal musculature, such as with a cough, sneeze, laugh or lifting. Stress incontinence is often secondary in part to weakening of the pelvic floor musculature, and is common after childbirth or abdominal surgery. It has been estimated that stress urinary incontinence occurs at least weekly in one third of adult women.

Additional reports indicate that more than 65% of female incontinence patients in the United States or 8.3 million women experience stress urinary incontinence. Of these women, approximately 85% or 7 million have incontinence primarily due to hypermobility of the bladder outlet, and approximately 15% or 1.3 million have incontinence primarily due to an intrinsic sphincter deficiency. Regardless of the etiology of UI, for the affected person it maybe a source of significant embarrassment and social isolation. As a result of this social stigma, many patients are reluctant to address this issue with their physician. Most primary care physicians "screen" for urinary incontinence by verbal or written questioning of the patient only. Additional basic evaluation may include a voluntary cough stress test, voiding diary, post void residual urinary volume, and urinalysis.

A patient experiencing urinary incontinence must be properly diagnosed to identify the specific type of incontinence from which the patient suffers. The treatments may be different, depending on the type of incontinence. Therefore, proper diagnosis becomes important at least for that reason.

Stress incontinence may result primarily in older women due to loss of extrinsic support for the pelvic organs and for the neck of the bladder. The tissues of the pelvis and of the distal urethra contain estrogen and progesterone receptors. Following menopause-and decrease of the hormones, the tissues of the urethra may lose resiliency and become somewhat flaccid. Under those conditions, any increase in intra-abdominal pressure causes urine in the bladder to be pushed outwardly as resistance in the urethra is overcome, resulting in leakage of urine. This condition is known as stress incontinence and occurs in the absence of contractions by the detrusor muscle of the bladder. Stress incontinence may be responsive to treatment with exogenous estrogens, although this is not an effective treatment for all patients, particularly depending on age. Alternative treatments may include pelvic muscle exercises, α-adrenergic agents, such as phenylpropanolamine, that act on the α-adrenergic receptors along the urethra and increase urethral tone.

The most common cause of urinary incontinence, however, is detrusor hyperreflexia, or hyperactivity of the detrusor muscle. This type of incontinence is believed to result from lack of inhibition of the detrusor muscle due to a decreased detrusor reflex in the brain stem. Nevertheless, in most affected elderly there appears to be no underlying neurological defect. In this condition, treatment may include antispasmodic agents which tend to relax the wall of the bladder.

A typical test employed to distinguish these two types of urinary incontinence is one which increases intra-abdominal pressure so as to, in turn, put pressure on the bladder. The Valsalva maneuver is one such test. In this technique, the patient generates a muscular contraction of the chest, abdomen and diaphragm in a forced expiration against a closed glottis. This increases pressure within the thoracic cavity and also in the abdominal cavity. The Valsalva maneuver also refers to raising the pressure in the nasopharynx by a forced expiration with the mouth closed and the nostrils pinched, for example, to clear the patency of the Eustachian tubes. Other testing techniques involve having the patient jump up and down to jostle the bladder, or bend down so as to compress the abdomen. Yet another method involves having the patient generate one or more strong voluntary coughs.

It is known, however, that some patients are unable to perform these physical acts. For example, a patient may not be able to jump, or to bend, or to generate a strong voluntary cough. Additionally, there are some patients who will not be correctly diagnosed on the basis of the cough test, perhaps because their coughs are insufficiently strong. Accordingly, there is a need for alternative or supplementary tests that will aid in diagnosing urinary stress incontinence.

A rather complete discussion of methods of evaluating urinary incontinence is found in a February 2006 article by IL Martin et al. entitled, "Systematic Review and Evaluation of Methods of Assessing Urinary Incontinence (hereinafter referred to as Systematic review)."

One of the problems associated with the prior art techniques is that some patient's are unable or are unwilling to perform the physical acts to the extent needed. For example, a patient may not be able to jump, or to bend, or to generate a strong voluntary cough. For some patient's they maybe able to perform these acts, but be unwilling to do so because an involuntary release of urine maybe embarrassing or contrary to what is considered proper in society.

SUMMARY OF THE INVENTION

Various aspects of the invention are directed toward apparatus and techniques for evaluating urinary stress incontinence. Particularly, the invention is directed toward evaluating urinary stress incontinence using a reflexive cough test (RCT), which triggers an involuntary cough on the part of the patient. Such an involuntary cough overcomes problems of prior art techniques and produces a more reliable test for urinary stress incontinence.

A system and method evaluates a patient for stress urinary incontinence. An involuntary reflex cough event is induced within the patient that activates the nucleus ambiguous and medial motor cell column of the patient and stimulates involuntary cough activated paraspinal muscles in the pelvis of the patient. And elecromyogram (EMG) is obtained from the involuntary cough activated paraspinal muscles and its duration determined. Any urine leakage time that occurs during the involuntary reflex cough event is identified and correlated within a processor together with the urine leakage time and EMG and duration of cough event to determine stress urinary incontinence.

In one aspect the EMG is taken from the L5/S1 paraspinal muscles. The patient produces a voluntary cough before inducing and involuntary cough. Any urine leakage time is correlated with the urine leakage time obtained during the involuntary reflex cough event in a non-limiting aspect. The intra-abdominal pressure (IAP) is determined during the involuntary reflex cough event and correlated with the duration of the involuntary reflex cough event and urine leakage time. A peak IAP is determined in one non-limiting aspect. The average IAP is also determined in a non-limiting aspect. The area under the curve corresponding to IAP samples obtained during the involuntary reflex cough event is determined in another aspect. These are correlated with the IAP and duration of the involuntary reflex cough event.

A method, system and device are set forth. A device includes a housing configured for handheld use and at least one interface carried by the housing and configured to receive an electromyogram (EMG) from paraspinal muscles in the pelvis of the patient that have been activated by an involuntary reflex cough event that activates the nucleus ambiguous and medial motor cell column of the patient and data relating to any urine leakage at the time during the involuntary reflex cough test. The processor is carried by the housing and configured to receive and process the EMG and urine leakage time and correlate data regarding the duration of the involuntary reflex cough event to determine stress urinary incontinence in a non-limiting example.

BRIEF DESCRIPTION OF THE DRAWINGS

Other objects, features and advantages of the present invention will become apparent from the detailed description of the invention which follows, when considered in light of the accompanying drawings in which:

FIGS. 7A and 7B illustrate test results comparing a voluntary cough test and involuntary cough reflex test for assessing stress urinary incontinence.

FIGS. 11-13 are tables of results and showing statistics, correlation and samples for the average intraabdominal pressure (AIAP) (FIG. 11), the peak intraabdominal pressure (PIAP) (FIG. 12), and the Area under Curve (AUC) (FIG. 13) and comparing the involuntary reflex cough test (RCT) and the voluntary cough test (VCT).

FIGS. 17A-17C are tables showing a summary of the sensitivity, specificity, PPV and NPV in a study of urodynamic testing for SUI with comparisons for the voluntary cough test and the involuntary reflex cough test.

FIG. 20 is a table of results showing a (2×2) chi-squared statistical analysis for a series of tests and comparing the involuntary reflex cough test and voluntary cough test.

FIG. 21 are graphs showing urodynamic tracings for a voluntary cough test and the involuntary reflex cough test in a female patient who does not have a history of SUI and showing a summary of results.

FIG. 22 are graphs showing urodynamic tracings for a voluntary cough test and the involuntary reflex cough test in a female patient who has a moderate/severe history of SUI and showing a summary of results.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
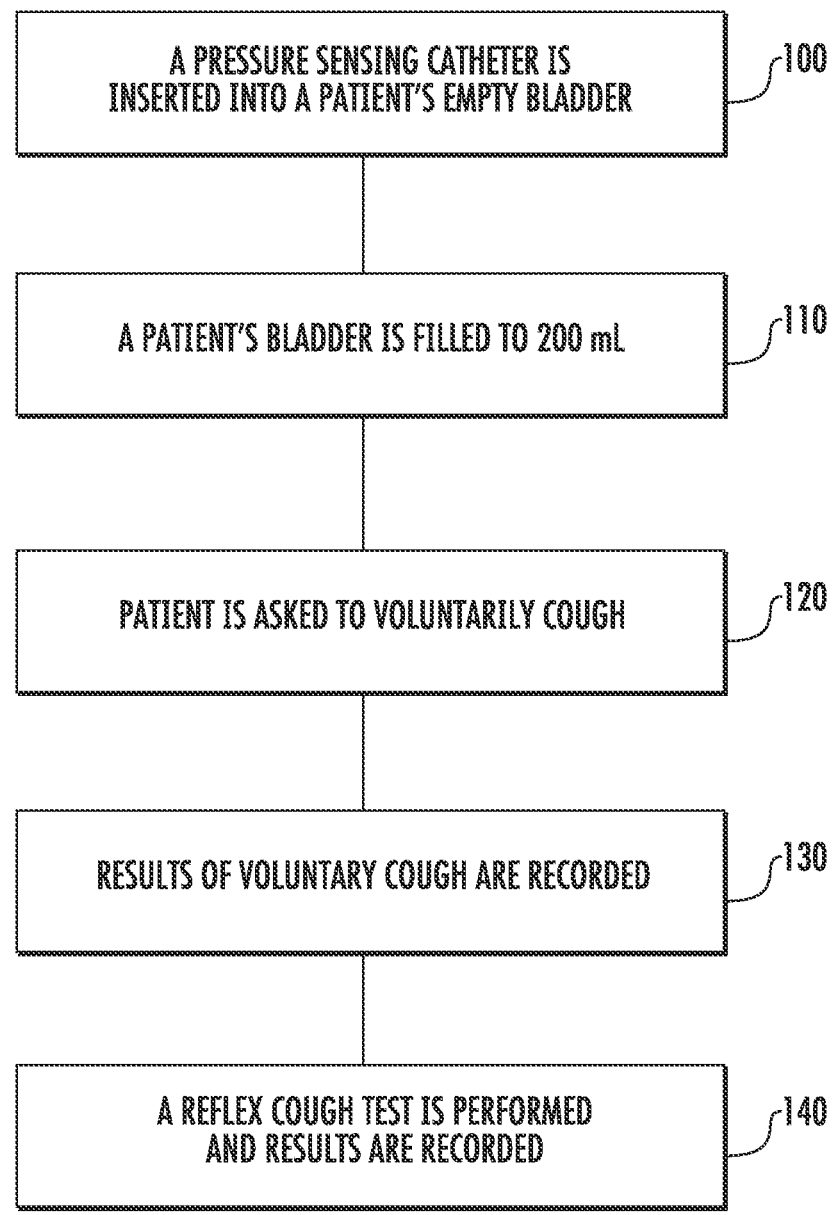
FIG. 1 shows a flowchart of a technique for evaluating a patient for urinary stress incontinence in accordance with one aspect of the invention.

FIG. 1 shows a flowchart of a technique for evaluating a patient for urinary stress incontinence in accordance with one aspect of the invention. As an initial step, pressure sensing catheter is inserted into a patient's empty bladder (100). The patient's bladder is then filled slowly with sterile water until 200 ml have been delivered (110).

The patient is then asked to voluntarily cough (120) and the results of the voluntary cough are recorded (130) by recording the variations in pressure as a function of time and by recording whether or not the cough induced involuntary expulsion of urine. See item 130.

Then, a reflex cough test is performed (140) and the results are recorded in a manner substantially similar to step 130. Details of the reflex cough tests are discussed more in conjunction with FIG. 2.

Figure 2:
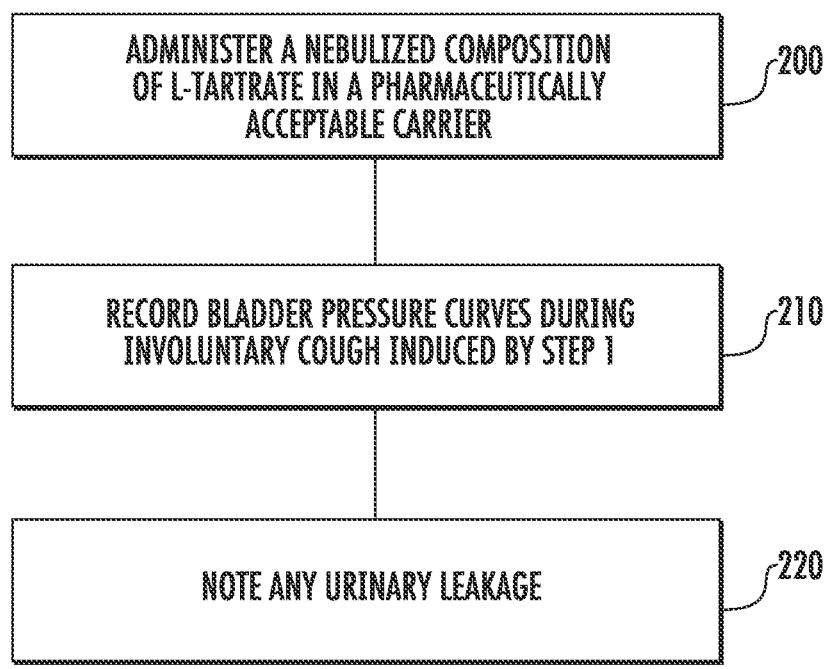
FIG. 2 shows a flowchart of a technique for conducting a reflexive cough test (ROT).

FIG. 2 shows a flowchart of a technique for conducting a reflex cough test. With the test arrangement in place as described in conjunction with items 100 and 110 of FIG. 1, instead of asking a patient to voluntarily cough, the patient is administered a nebulized composition of L-tartrate in a pharmaceutically acceptable carrier (200). The variations in bladder pressure that occur during the involuntary coughs induced by step 200 are then recorded and plotted for display (210). The patient is checked for any urinary leakage that occurs during the involuntary coughs (220).

Figure 3:
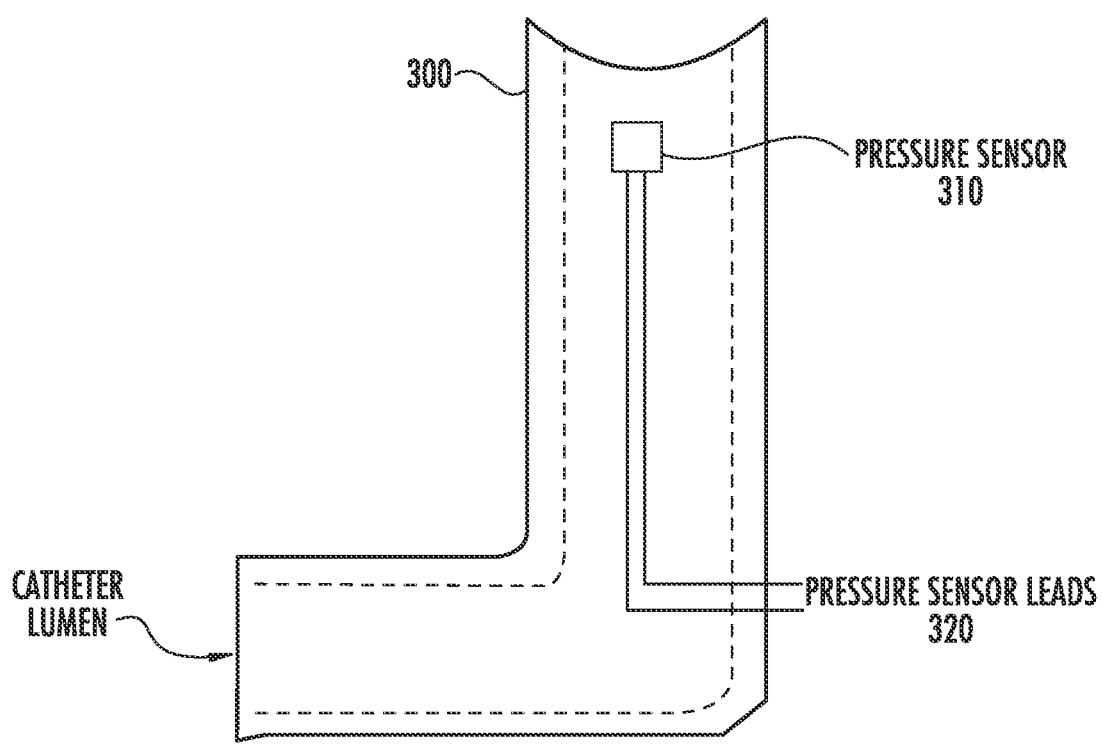
FIG. 3 shows a catheter that can be used for carrying out various aspects of the invention.

FIG. 3 shows a catheter that can be used for carrying out various aspects of the invention. A catheter, 300, includes a pressure sensor 310 and conductive wires or paths which conduct the electrical output of the pressure sensor 310 to external circuitry. The wires or paths are hereinafter called pressure sensor leads 320. The catheter lumen can be utilized to fill or drain the patient's bladder as appropriate. Examples of a catheter usable in accordance with the invention may include a Foley catheter equipped with a pressure sensor.

Figure 4:
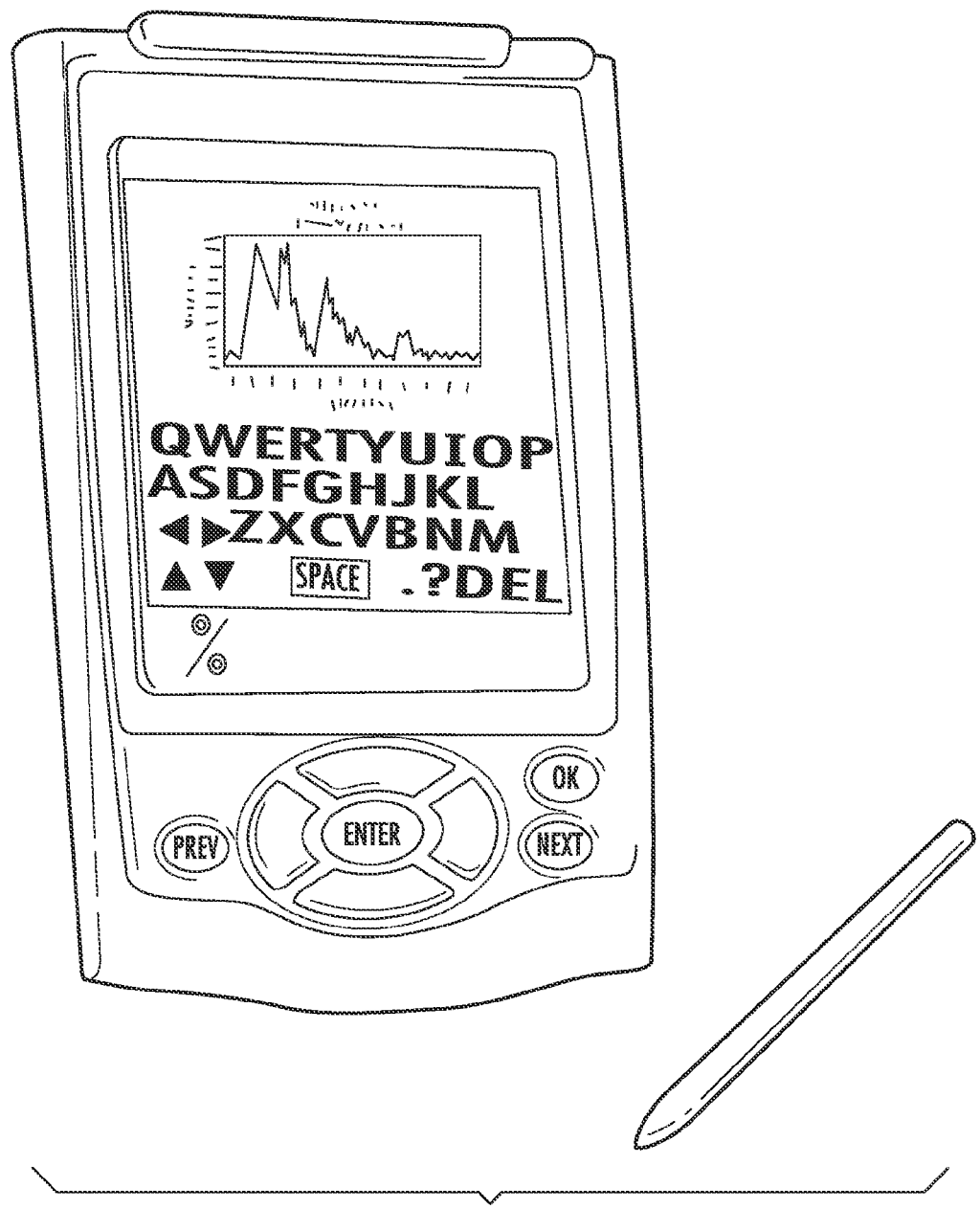
FIG. 4 is an illustration of a handheld device that can be used to carry out the invention.

FIG. 4 is an illustration of a handheld processing device that can be used to carry out the invention. As shown on the device display screen, the variation in pressure that occurs as a function of time during a voluntary or involuntary cough is displayed.

Figure 5:
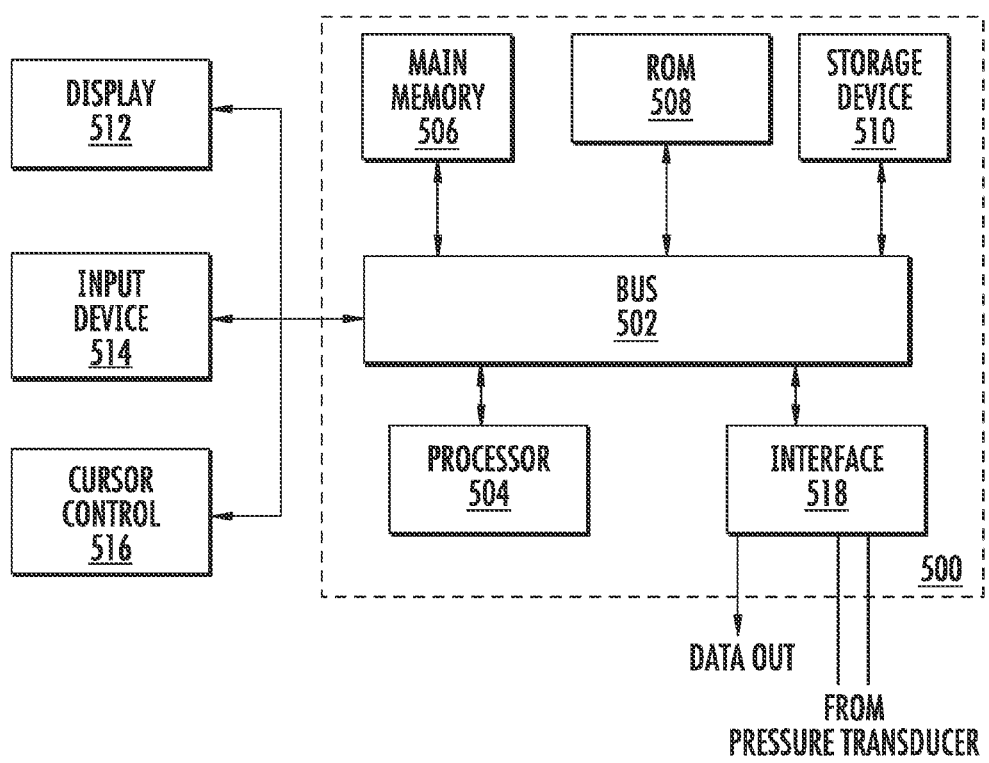
FIG. 5 is a block diagram of an exemplary processing device, such as used in the handheld device, which can be used to carry out aspects of the invention.

FIG. 5 is a block diagram of an exemplary processing device as part of the handheld device that can be utilized to carry out aspects of the invention. FIG. 5 is a block diagram that illustrates a computer system 500 upon which an embodiment of the invention may be implemented. Computer system 500 includes a bus 502 or other communication mechanism for communicating information, and a processor 504 coupled with bus 502 for processing information. Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504. A storage device 510, such as a magnetic disk or optical disk, is provided and coupled to bus 502 for storing information and instructions.

The interface 518 receives signals from pressure transducers connected to catheters inserted through the urethra and/or rectum and other signals, for example, EMG (electromyogram) signals such as taken from the paraspinal muscles as explained in greater detail below. EMG signals can be processed alone without catheter processor signals.

Computer system 500 may be coupled via bus 502 to a display 512, such as a cathode ray tube (CRT), for displaying information to a computer user. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 104 and for controlling cursor movement on display 512. This input device typically has two degrees of freedom in two axes, a first axis (e.g., x) and a second axis (e.g., y), that allows the device to specify positions in a plane.

Computer system 500 operates in response to processor 504 executing one or more sequences of one or more instructions contained in main memory 506. Such instructions may be read into main memory 506 from another computer-readable medium, such as storage device 510. Execution of the sequences of instructions contained in main memory 506 causes processor 504 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 504 for execution. Such a medium may take many forms, including but not limited to, non-volatile media, volatile media, and transmission media. Non-volatile media includes, for example, optical or magnetic disks, such as storage device 510. Volatile media includes dynamic memory, such as main memory 506. Transmission media includes coaxial cables, copper wire and fiber optics, including the wires that comprise bus 502. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on a magnetic disk of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector can receive the data carried in the infra-red signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

Figure 6:
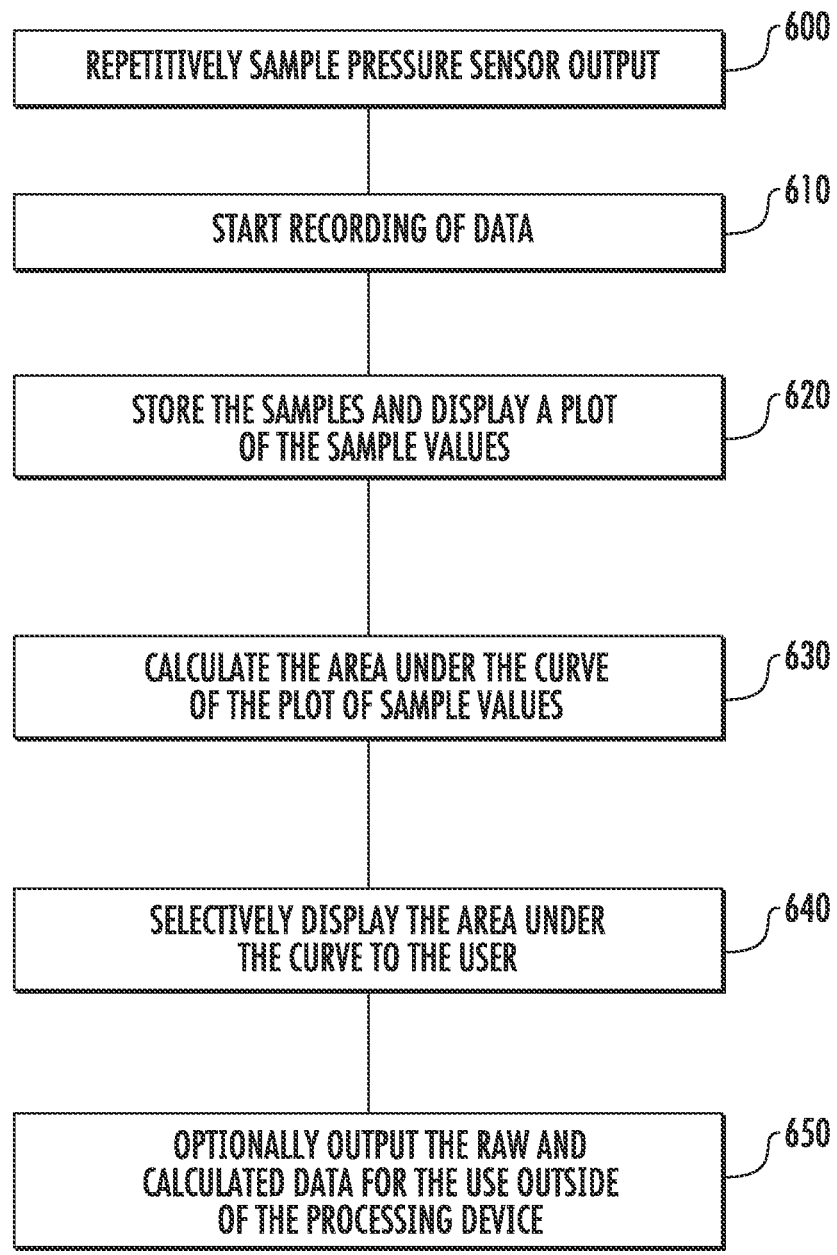
FIG. 6 is a flowchart of software used to program a processing device in accordance with one aspect of the invention.

FIG. 6 is a flowchart of software used to program a processing device in accordance with one aspect of the invention. The processing device is programmed to repetitively sample pressure output from the sensor (600). Upon receipt of an initiation or start signal, the processor can start recording data from the pressure sensor (610). The start signal can be generated by utilizing either a rapid increase in pressure, by detecting a pressure threshold being exceeded, or by receiving a trigger signal initiated by a user. Such a signal was discussed in conjunction with U.S. patent application Ser. No. 10/783,442, filed Feb. 20, 2004, entitled Apparatus For Evaluating A Patient's Laryngeal Cough Reflex And Associated Methods, by W. Robert Addington, Stuart Miller and Robert Stephens, referred to above.

After receipt of the starts signal, the processing unit stores the samples and displays the plot of the pressure sample values (620).

Upon completion of the cough sequence, software is programmed to calculate the area under the curve of a plot of the sample values (630). The areas under the curve (AUC) values are calculated by the numerical integration of intravesical pressure over time with either Simpson's ⅜-rule or Bode (or Boole's) rule. Both Simpson's ⅜-rule and Bode (or Boole's) rule are methods of numerical integration that yield more accurate results for AUC than the trapezoidal method.

Simpson's ⅜ rule:

$$\int_\alpha^\beta f(x)dx \approx \frac{3h}{8}\{f_0 + f_n + 3(f_1 + f_4 + \ldots + f_{n-2}) +$$
$$3(f_2 + f_5 + \ldots + f_{n-1}) + 2(f_3 + f_6 + \ldots + f_{n-3})\}$$
$$= \frac{3h}{8}\left\{f(\alpha) + f(\beta) + 3\sum_{i=1,4,7,\ldots}^{n-2} f(\alpha + ih) + 3\sum_{i=2,5,8,\ldots}^{n-1} f(\alpha + ih) + 2\sum_{i=3,6,9,\ldots}^{n-3} f(\alpha + ih)\right\}$$

Bode's (Boole's) rule:

$$\int_{x_1}^{x_5} f(x)dx = \frac{2}{45}h(7f_1 + 32f_2 + 12f_3 + 32f_4 + 7f_5) - \frac{8}{945}h^7 f^{(6)}(\xi).$$

All AUC values were calculated using Bode's (Boole's) rule, except for that of Patient #1, which was calculated with Simpson's ⅜-rule. Bode's (Boole's) method was not very adept at handling as few data points (3).

The process may selectively display the calculated area under the curve to the user either with or separately from display of the plot of the sample values (640).

Optionally, one may output the raw and calculated data for use outside of the processing device (650). This can be done utilizing interface 518.

FIGS. 7A and 7B illustrate test results comparing voluntary cough and involuntary cough techniques for assessing stress urinary incontinence.

The testing that produced the results shown in FIGS. 7A and 7B are described as follows.

Objective: The objective of this study were to:

1) Evaluate the effectiveness of the reflex cough test (RCT) versus voluntary cough in confirming stress urinary incontinence in female subjects with a history of mild urinary incontinence as determined by the Incontinence Quality of Life Instrument (I-QOL); and 2) Correlate, if indicated, intravesicular pressure measurements with urinary leakage after RCT.

Materials and Methods: Voluntary and involuntary (RCT) cough provocation maneuvers were performed during urodynamic testing in 6 women. Four women had a history of mild stress urinary incontinence and two were normal controls. The order of the cough provocation procedures was randomized.

Prior to urodynamic assessment, subjects were instructed to empty the bladder (confirmed via ultrasound). Using sterile technique, calibrated bladder and rectal catheters were placed and continuous dual-channel pressure recording was performed and the subject's bladder was filled slowly with sterile water until 200 mL had been delivered.

Cough Leak Point Pressure (CLPP) was assessed with a bladder volume of 200 mL. Leakage was determined by visual inspection of the perineum by the Investigator during the coughs, and electronically marked on the print-out. If the subject did not leak with either cough maneuver in the semi-recumbent position, the standing position was used. Urodynamic testing was completed with filling to capacity to observe for detrusor instability.

After instruction, subjects performed a maximal forceful voluntary cough (VC) and an involuntary cough. The involuntary cough was elicited by stimulating the laryngeal cough reflex by performing the RCT with the patient's nose held closed. The RCT involves inhaling a concentration of 20% L-(+)-tartaric acid dissolved in normal, sterile saline (Nephron Pharmaceuticals, Orlando, Fla.) delivered via jet nebulizer.

An independent reviewer used the continuous pressure recording of each subject to determine peak pressures, measure duration of the cough events, count the number of pressure spikes, and derive area under the curve (AUC) numbers.

Results: Peak pressures were similar when comparing voluntary cough with the RCT (FIGS. 7A and 7B). Duration of cough events, AUC, and number of spikes were all increased with RCT relative to voluntary cough. Neither of the 2 normal subjects leaked with either cough maneuver. Of the 4 subjects with mild stress urinary incontinence (diagnosed by I-QOL), 3 leaked with RCT and 2 leaked with VC. A possible carry-over effect was identified when assessing subjects that were randomized to undergo RCT testing prior to VC. There appear to be a relative increase in AUC, peak pressure, duration, and in the number of spikes with VC testing when voluntary cough testing was performed after, rather then prior art to, the RCT (FIGS. 7A and 7B). It is notable that both subjects that leaked with voluntary cough were randomized to have the RCT performed first.

RCT provides considerable "stress" in subjects with stress urinary incontinence and appears to be a useful involuntary maneuver in eliciting leakage in subjects with this condition. No other involuntary maneuver has been studied in evaluating this condition. The data suggests that RCT may be more efficient in provoking leakage in subjects with stress urinary incontinence than voluntary cough.

Figure 8:
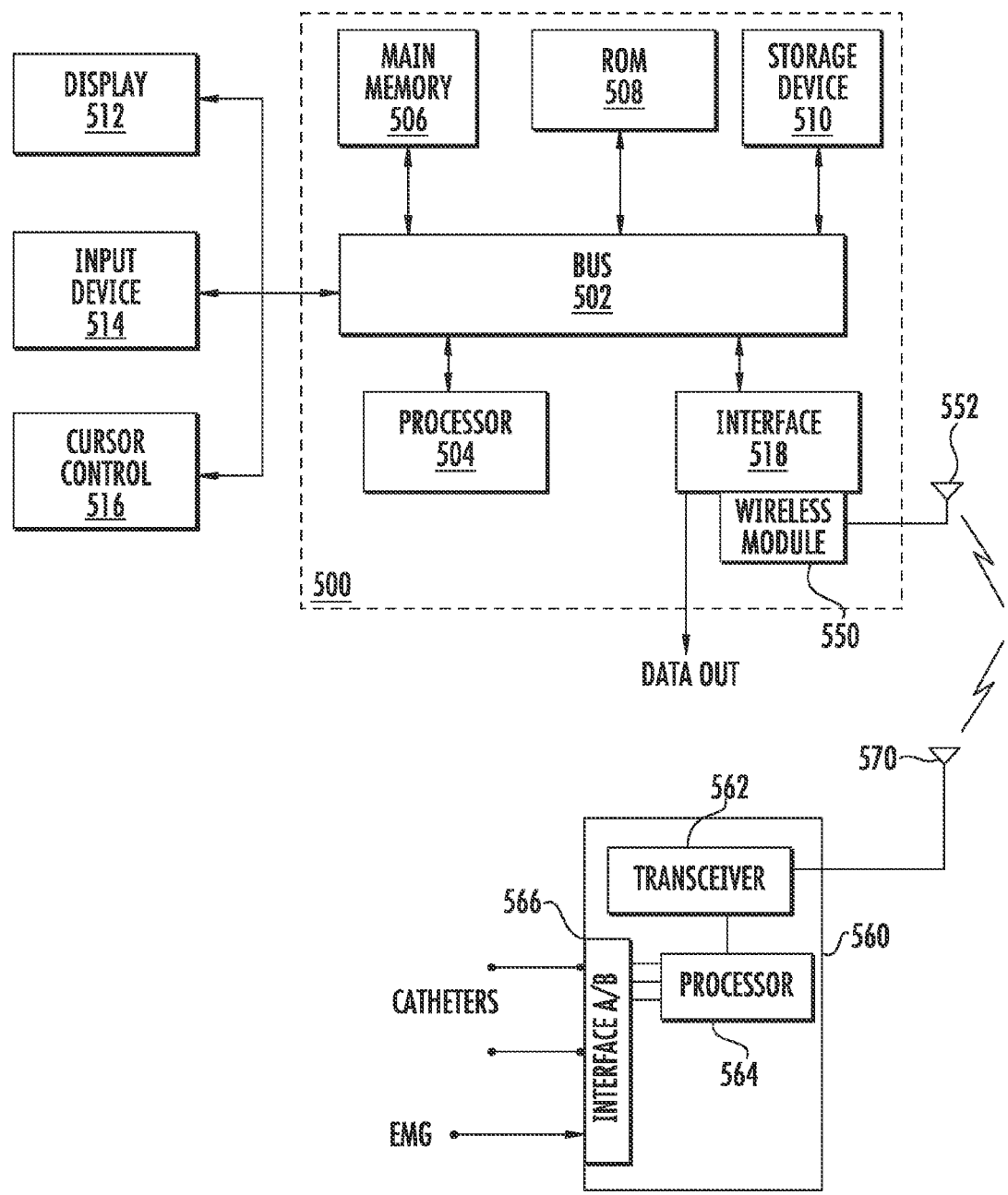
FIG. 8 is a block diagram similar to the block diagram shown in FIG. 5 and showing a wireless interface and a wireless module in the handheld device that communicates wirelessly to a wireless sensing device, which connects to catheters or other inputs, including an EMG signal input in accordance with a non-limiting example.

FIG. 8 is a block diagram of a processing device 500 as part of the handheld device similar to that shown in FIG. 4, but showing a wireless module 550 and antenna 552, which communicate wirelessly to a wireless sensing device 560. The wireless sensing device includes a wireless transceiver 562, processor 564 and interface 566 that connects to catheters or other input devices such as an EMG signal input obtained through EMG pads and associated components located at the paraspinal, for example, in a preferred embodiment. Data is transmitted using wireless communications signals via the transceiver 562 and antenna 570 to the handheld device that incorporates the processing device 500. Data processing is accomplished in the handheld device using appropriate circuitry as described before.

There now follows greater details of the involuntary reflex cough used not only for accessing stress urinary incontinence, but also for use as a medical diagnostic tool in accordance with non-limiting examples.

There now follows a general description of physiology for the involuntary reflex cough test (iRCT), which activates the Nucleus Ambiguus. The iRCT selectively activates the Medial Motor Cell Column (MMCC) of the spinal cord rather than the (Lateral) LMCC to fire muscles embryologically predetermined to be involuntary cough activated muscles in the pelvis. In the past, urologists did not selectively activate MMCC without overtly activating the LMCC. Magnetic stimulation or electrical spinal cord stimulation activate both cell columns and thus it is not possible to sort out pathology with these. Magnetic stimulation or other approaches from CNS activation set off both columns.

The pelvic muscles that typically are activated with MMCC cough activation include the lumbar-sacral L5/S1 paraspinal axial musculature, which facilitates inpatient continence screening. An example is through MMCC iRCT muscle activation, obtaining L5/S1 paraspinal firing but not L5/S1 lateral gastrocnemius activation because the gastroc muscles are limb muscles activated primarily through the LMCC.

The L-S paraspinals are easier to access with a large pad placed above the sacrum on the midline that contains active, reference and ground combined. It is not important to determine lateralization of the activity like needle EMG for radiculopathy, but only if activation occurs reflexively where the onset latency is under the pressure activation of the abdomen such as the Levator Ani. This is a poor muscle for these purposes because people train it to activate and set their pelvis if the person senses any intra-abdominal pressure elevation. Also, it is difficult to get pads to stick to that area with hair, perspiration, fungal infections or bowel/bladder incontinence present, and other factors.

Some examples have been developed and studied, including a normal CNS patient with Lumax bladder and bowel catheters and pads at L5/S1 paraspinals and a separate EMG machine and electrodes at the pelvic floor in a standard 3:00 and 9:00 o'clock set-up to demonstrate simultaneous involuntary activation with iRCT. This sets off the pelvic floor muscles. Thus, normal airway protection data is obtained and normal CNS data to L1 (where spinal cord ends). The set-up includes a complete T12 that cannot void and needs intermittent catheterization with the same set up, thus demonstrating data for normal airway but no L5/S1 EMG activation by MMCC with all the other data necessary to prove an unsafe bladder by the algorithm. A quadriplegic can demonstrate abnormal airway protection and abnormal EMG activation at both paraspinal and pelvic floor muscles with unsafe bladder measurements that follow the algorithm.

It should be understood that iRCT is an involuntary maneuver that activates embryologically predetermined muscles for airway protection and continence that travel primarily through the MMCC in the spinal cord. Different varieties of lesions are captured and determined with summated interval data approach for general screening purposes.

There now follows an initial study of the iRCT test results relative to SUI and followed by detailed examples showing support for iRCT to determine SUI and for neurophysiological analysis and showing progressive understanding of the advantageous use of the iRCT.

It is known that the laryngeal cough reflex (LCR) is a strong brainstem-mediated reflex that protects the upper airway by preventing aspiration, or the entrance of secretions, food, and/or fluid into the airway below the level of the true vocal cords (rima glottidis), through elicitation of an involuntary cough. The LCR is activated through the stimulation of cough receptors in the vestibule of the larynx. One way this is achieved is through the inhalation of chemostimulants, such as tartaric acid. Studies have shown that if the LCR is intact, the subject will involuntarily cough (normal LCR) upon inhaling a solution containing TA.

In one non-limiting example, the iRCT involves the inhalation of a nebulized 20% normal saline solution of L-TA (Tartaric Acid). Subjects are asked to perform 1 to 3 effective, full inhalations (about 15-20 second exposure by mouth for tidal breathing wearing a nose clip) from a standard jet nebulizer with at least 50 psi from an oxygen wall unit or tank that produces an average droplet diameter of 1 to 2 microns or less. The nebulizer output is 0.58 mL/min. The initiation of an involuntary cough reflex after any one of the inhalations is the end point of the procedure.

Nebulized TA is a chemical tussive that stimulates irritant receptors in the mucosa of the laryngeal aditus. Mild irritation of these receptors results in nerve impulses being conveyed by the internal branch of the superior laryngeal nerve (ibSLN) to bulbar centers of the brainstem. This nerve constitutes the afferent sensory component of the LCR arc. The efferent component of the LCR is mediated through the vagus, phrenic, intercostals and thoracoabdominal nerves.

Inhaled TA is selective in stimulating rapidly adapting ("irritant") receptors (RARs), in the supraglottic region. In humans, bilateral anesthesia of the ibSLN abolishes TA-induced cough and permits tidal breathing of the nebulized vapor without coughing, supporting the idea that the RARs are responsible for TA-induced cough.

The physiological response from inhalation of TA in a normal subject is abrupt, forceful coughing of short duration. Using a 20% solution of inhaled nebulized TA is a safe, reliable way to assess the sensation in the supraglottic laryngeal region and subsequently the neurologic circuitry of the LCR. In addition, the ability of the iRCT to predict the integrity of the protective LCR in subjects with stroke has been studied.

A 20% solution of TA as an aerosol causes cough by stimulating sensory nerves in and under the laryngeal epithelium. These nerves have been identified histologically, and the reflexes they cause have been identified. The sensory nerves can be stimulated by both non-isosmolar and acid solutions. Tartaric acid may act in both ways, but the balance between them is uncertain.

The nerves are stimulated by the opening of membrane channels in the nerve terminals. More than 20 categories of channels have now been identified, the opening of which will allow calcium flow into the nerve (and also sodium, with exit of potassium), with the result that an action potential is set up, which travels to the brainstem in the central nervous system (CNS), and reflexively induces cough.

Several different types of sensory nerve ending in the larynx have been identified that may mediate cough and other defensive reflexes. They have been extensively studied, mainly in experimental animals by recording the action potentials in their nerve fibers. The probable candidates for cough are the RARs or 'irritant' receptors. These are highly sensitive to mechanical stimuli, to hyperosmolar solutions, and to acids.

Once stimulated, the sensory nerves will induce a variety of defensive reflexes which protect the lungs from invasion of harmful material. These include cough (an inspiration, followed by a forced expiration against a closed glottis, followed by opening of the glottis with an expiratory blast); the laryngeal cough expiratory reflex (LCER, a powerful expiratory effort with the glottis open); and the glottal closure reflex. In some instances a reflex apnea can be produced. The balance of these reflexes may depend on the nature and the strength of the stimulus. In the case of TA, the LCER seems to be dominant, possibly followed by glottal closure, and the pathophysiological advantage of this response in preventing aspiration is obvious.

There is clinical experience in subjects with stress urinary incontinence. A pilot study was initially designed as a single-center, single-blind study to evaluate the effectiveness of the iRCT in inducing an involuntary cough that would confirm urinary leakage in female subjects with a history of mild SUI. Up to 3 inhalations of a 20% sterile, aqueous solution of TA delivered via an ultrasonic jet nebulizer with oxygen at 50 psi to deliver droplets of ≤1 μm were administered to yield a reflex cough. The primary endpoint was the observation of urinary incontinence in subjects with a history of mild SUI during iRCT and a lack of urinary incontinence in normal subjects. Secondary endpoints were documentation of bladder and abdominal pressures and tolerability of iRCT.

The initial enrollment was 6 women (18-75 years of age), including 4 women with a history of mild SUI as determined by the Incontinence Quality of Life Instrument (IQOL) and 2 healthy controls with no history of SUI. However, the protocol was amended to increase total enrollment from 6 to 9 subjects (7 with SUI and 2 healthy controls).

The study protocol assessed the two cough provocation maneuvers (voluntary cough test and iRCT) for each subject. The order of the cough provocation was randomized but each subject completed both tests. The protocol was subsequently amended to remove blinding and randomization from the study and all subsequently enrolled subjects underwent VCT followed by iRCT followed by a second VCT. Subjects underwent the provocation maneuvers within 30 days of screening and then had two follow-up visits: the first 1 to 5 days after treatment; the second 5 to 7 days after treatment.

Urodynamic evaluation was done during each cough maneuver. The parameters determined during this evaluation included maximal urethral pressure (MUP), maximal abdominal pressure (MAPF), maximal detrussor pressure (MDPP), maximal abdominal leak point pressure (MALPP), maximal detrussor leak point pressure (MALPP), and CLPP.

A total of 9 subjects were evaluated, 2 without SUI and 7 with a history of mild SUI. All subjects enrolled in this study were white and not of Hispanic or Latino background. Subject age ranged from 31 to 71 years. The mean subject age was 48.4 years: 51.0 years for healthy controls and 47.7 years for subjects with SUI. Two (22%) subjects were smokers: 1 (50%) healthy control and 1 (14%) subject with SUI. The remaining 7 (78%) subjects were non-smokers.

Individual subject responses to the cough provocation tests are summarized in Table 1. The two control subjects (#2 and #3) did not leak with either VCT or iRCT. Of the remaining 7 subjects with mild SUI, only 2 subjects (#8 and #4) did not produce leak with either VCT or iRCT. Two other subjects (#5 and #6) produced leak with both VCT and iRCT. The remaining 3 subjects (#1, #7, and #9) did not produce leakage with VCT but did with the iRCT.

TABLE 1

Individual Subject Responses to iRCT and VCT: Protocol PNEU-01-002

| | | Urine Leakage? | | |
|---|---|---|---|---|
| Subject | Status | VCT | iRCT | VCT |
| 2 | Normal | No | No | — |
| 3 | Normal | No | No | — |
| 1 | SUI | No | Yes | — |
| 4 | SUI | No | No | — |
| 5 | SUI | Yes | Yes | — |
| 6 | SUI | Yes | Yes | — |
| 7 | SUI | No | Yes | No |
| 8 | SUI | No | No | No |
| 9 | SUI | No | Yes | No |

VCT, voluntary cough test;
iRCT, induced cough reflex test;
SUI, stress urinary incontinence.

The performance of the cough provocation procedures is presented in Table 2. Sensitivity of the cough provocation maneuvers was 71.4% during iRCT and 28.6% during VCT. Specificity was 100% during iRCT and VCT. The positive predictive value (PPV) was 100% for iRCT and VCT; the negative predictive value (NPV) was 50% for iRCT and 28.6% for voluntary cough.

TABLE 2

Performance Statistics of the Cough Procedures: Evaluable Population

| | Voluntary Cough N = 9 | Reflex Cough N = 9 |
|---|---|---|
| Sensitivity[1], n/N (%) | 28.6 | 71.4 |
| Specificity[2], n/N (%) | 100 | 100 |
| PPV[3], n/N (%) | 100 | 100 |
| NPV[4], n/N (%) | 28.6 | 50 |

PPV, positive predictive value;
NPV, negative predictive value;
TP, true positive;
FN, false negative;
TN, true negative;
FP, false positive.
[1]Sensitivity = TP/(TP + FN)
[2]Specificity = TN/(TN + FP)
[3]PPV = TP/(TP + FP)
[4]NPV = TN/(TN + FN)
The evaluable population was defined as all subjects who met study entry criteria and completed all cough maneuvers.
For subjects enrolled after Protocol Amendment 1, data from the first voluntary cough was used.

The urodynamic parameters were summarized and there was a trend for increased mean abdominal pressure (cm $H_2O$) and mean detrussor pressure when the subjects were administered the iRCT compared with the VCT. The CLPP was not consistently higher after iRCT compared with after VCT.

The trend for an increase in abdominal and intravesicular pressures after the iRCT compared with the VCT in those subjects who experienced leakage suggests that the iRCT causes significant stress on the sphincter, resulting in urinary leakage.

Analysis compared a digitized area under the pressure curve (AOC) after the iRCT, and after VCT was also conducted. Digitization of the pressure-time curve from the recordings allowed quantification of the stress generated during the cough procedures. Using the average intravesicular pressure ($P_{ves}$) values, AUC values were calculated by the numerical integration of $P_{ves}$ over time with either Simpson's ⅜-rule or Bode (or Boole's) rule. There was a trend for higher peak $P_{ves}$ and greater AUCs in subjects after iRCT compared with VCT. The results show that the iRCT provides a larger and more robust stress than VCT. The relatively increased value of AUC measurements with iRCT are a good numerical representation of the magnitude of stress placed on the urethral sphincter and offers an explanation for the increased number of subjects with mild SUI that leaked with iRCT when compared to VCT.

These results, combined with the urinary leakage observed after the iRCT, show that the iRCT has clinical utility in producing a standardized cough that allows for a definitive diagnosis of SUI as later explained in greater detail with further results.

No AE's occurred during this study and no clinically significant laboratory abnormalities were noted. No subjects discontinued from the study for any reason. The iRCT procedure was safe and tolerable to the subjects in this study.

In summary, three out of five women (60%) with SUI experienced urinary leakage only after the iRCT while two of the SUI subjects (40%) experienced urinary leakage after both the iRCT and VCT. Neither of the two healthy control subjects experienced urinary leakage after either the iRCT or VCT. Based on these initial results, the iRCT is more specific and sensitive than the VCT, indicating that iRCT is advantageous in the diagnosis of SUI.

There now follows an analysis and test results in greater detail that explain the advantageous use of the involuntary reflex cough test (iRCT) for investigating and diagnosing not only SUI but also physiological abnormalities such as neurologic deficiencies. It should be understood that there are differences between normal and neurological patients.

As noted before, there are ranges and boundaries with parameters that are now used to establish a normal neurological range. Some of the graphs representative of urodynamic testing as explained below show a delay between the EMG muscle activity and actual occurrence of a leak. In one non-limiting example, it is no more than a few milliseconds (six) in some examples between when the patient coughs and the leak occurs. The EMG corresponds to the electromyogram test and detects muscle electrical activity. It can be displayed visually on an oscilloscope and detected with signal peaks in a non-limiting example.

It is possible to conduct a Nerve Conduction Velocity (NCV) test as verification, and if there is a large delay, for example, six milliseconds, in one aspect, it could correspond to a neuropathological problem. In accordance with a non-limiting example, the involuntary reflex cough test (iRCT) is useful as a medical diagnostic tool and permits analysis of neuropathological problems. The involuntary reflex cough test also is used for analyzing stress urinary incontinence. A data processing methodology based on urodynamic testing and useful with the handheld device as described above is later set forth. A methodology for stress urinary incontinence analysis using the handheld device for example, is explained relative to the flowcharts of FIGS. 23-26. The involuntary reflex cough test as explained can be used as a standardized test in conjunction with the data processing as described. This is distinctive from an analysis using a voluntary cough in which a patient has time to set their pelvis. Processing EMG data also is accomplished in some examples in which the EMG is taken from the paraspinal instead of the perineal.

The EMG from the parineal muscles respond almost simultaneously to the onset of the voluntary cough because the patient does not want to leak. With the involuntary reflex cough test, on the other hand, the fast fibers that are set off reach the abdominal muscles quickly, such as in 17 milliseconds as an example. The patient is not able to set their pelvis. In some of the graphs reflecting urodynamic testing as will be described, it is evident that the onset of the EMG activity does not happen at the same time the pressure rises. Some people that have neuropathy, for example, spinal stenosis or nerve injury (even if it is mild), have a situation that prevents the reflexes from closing before the pressure has changed to push on the bladder. It is not possible to obtain this diagnostic tool methodology unless the involuntary cough reflex test is accomplished. When the involuntary reflex cough test is accomplished, it is possible to demonstrate a latency delay and show that the pathophysiology is a neuropathic problem rather than a structural problem. It is possible to separate the pathophysiology using the involuntary reflex cough test and methodology as described.

In one example, a female patient could have a weak spinal cord and her physiology is normal. This patient may not leak during the test, but the patient cannot protect her airway. Thus, using the methodology apparatus and system associated with the involuntary reflex cough test, in accordance with non-limiting examples, it is possible not only to diagnose an unprotected airway, but also to diagnose normal bladder physiology, including the neurophysiology to the patient's sphincter closure process. This is advantageous because it is then possible to determine when someone cannot protect their airway, even though they may have a normal bladder. Conversely, there are patients with a normal airway, but cannot control their bladder. This process and system as described is able to make that diagnosis and thus the involuntary reflex cough test is an advantageous medical diagnostic tool. For example, it is possible to have a patient with a poorly functioning bladder and normal airway and use of the test allows a doctor to find lower urinary tract symptoms and neuropathology. It becomes possible to diagnose a level of lesion in a patient with a full comprehensive neurologic examination using the involuntary reflex cough test, methodology and apparatus as described.

As will be described in detail later, the various components such as the nebulizer, one or more catheters, any pads for the paraspinal muscles when EMG is used, and drug as part of the nebulizer are inserted in a kit for use at the clinic, hospital or setting. Those components can be discarded after use. The handheld device, of course, will be used again. Use of the kit provides a clinician, doctor or other medical professional the readily available diagnostic tool to determine if a patient has a questionable airway and determine bladder physiology at the same time, all with the use of the one kit.

The EMG component of the waveform is typically important for analysis as explained. Two catheters are used in some analysis, one for the rectum and one for bladder. In another example one catheter is used. In yet another example no catheter is used. EMG is taken from the paraspinals. In examples, the intravesicular pressure is important in combination with EMG taken at paraspinals. The EMG is correlated with pressure (e.g., intravesicular pressure) and a delay component. In the preferred method, the EMG is taken from the paraspinal muscles to obtain a clean signal where EMG sensors are placed on the back at the spine. In conjunction with the clean EMG signal obtained from the paraspinal muscles, it is possible to obtain the representation of where the involuntary cough event "take-off" starts and where it ends. The handheld device includes a processing device such as a microprocessor and appropriate software that correlates the data. It is possible to obtain a diagnosis for the level of lesion in a patient, while also obtaining a full comprehensive neurophysiological examination as noted before. Data is obtained from the involuntary reflex cough test and from the EMG. In one aspect depending on the type of desired analysis, a catheter is used in a non-limiting example to obtain the intravesicular pressure ($P_{VES}$).

Figure 9:
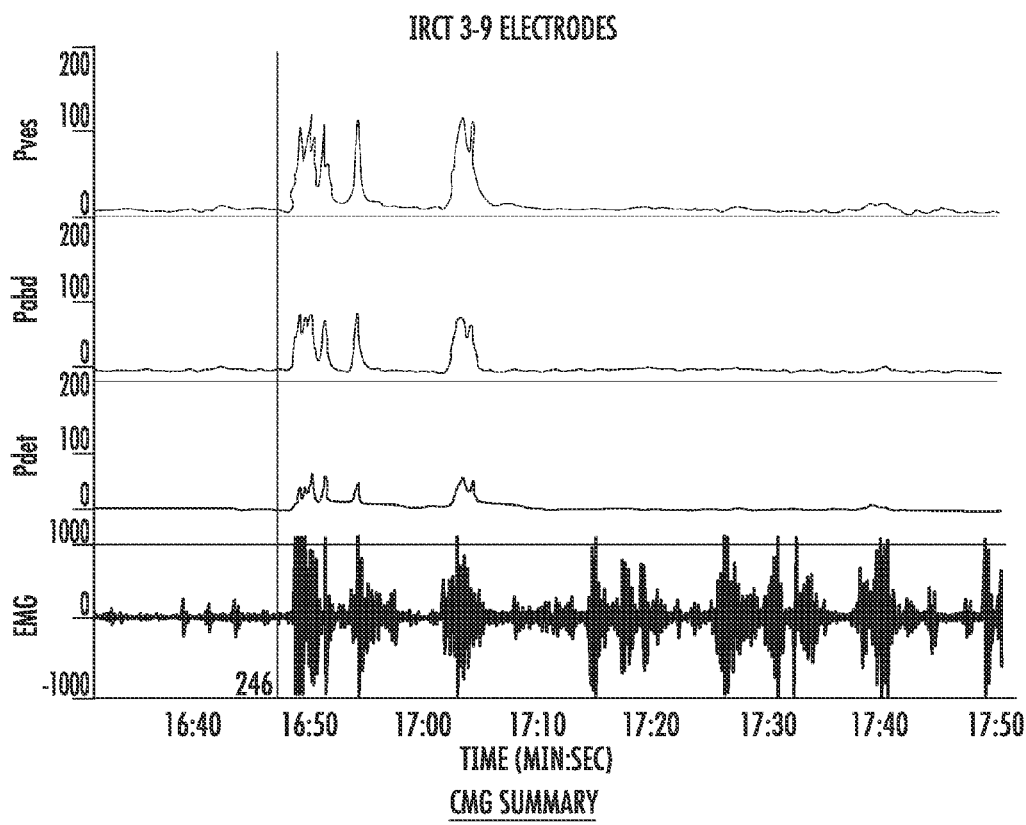
FIGS. 9 and 10 are graphs of urodynamic tracings showing results for the EMG, detrusor, abdominal and vesicular pressures for the involuntary cough reflex test (iRct) when the EMG is taken from the perineal (FIG. 9) and when the EMG is taken from the L5/S1 (FIG. 10) in accordance with a non-limiting example.
Figure 10:
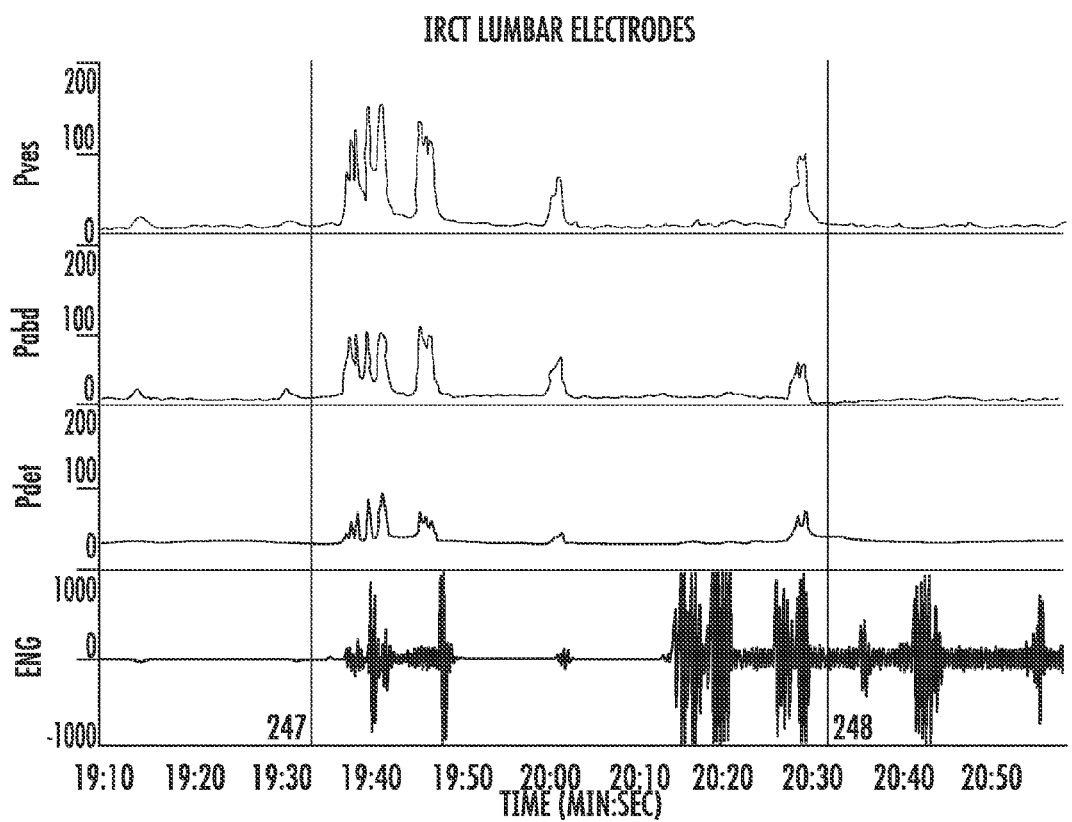

Referring now to the graphs for the urodynamic testing shown in FIGS. 9 and 10, there is illustrated time in seconds (horizontal axis) for the involuntary cough reflex test event and the various components corresponding to the vesicular pressure, abdominal pressure ($P_{VES}$) detrusor pressure, and the EMG on the vertical axis. FIG. 9 shows results for involuntary reflex cough tests when the EMG signal is taken from the perineal. Electrodes were placed at the 3:00 and 9:00 o'clock positions near the vagina for the EMG taken from the perineal. FIG. 10 shows the involuntary reflex cough test using lumbar electrodes at the L5/S1 for EMG. In these examples, the EMG's were taken from a patient that cannot void following an L-S laminectomy infusion. This patient tolerated filling the 200 millimeters and had a stress urinary incontinence history and stress urinary incontinence on the involuntary reflex cough test. The patient could not void despite the stress urinary incontinence and had low voiding pressures after filling to 350 ml, hypotonic bladder. This was a unique mix of hypotonic bladder and SUI, but otherwise no overflow incontinence. These graphs show that a better determination is made for the iRCT (involuntary reflex cough test) and EMG signal results from the L5/S1 paraspinal with a current Lumax EMG baseline. L5 corresponds to the last vertebrae in the lumbar spine and S1 corresponds to the first vertebrae in the sacral spine.

It should be understood that a Foley catheter could block the urethra. A smaller catheter is preferred to measure such as described relative to the catheter of FIGS. 31 and 32 in one non-limiting example. Some studies indicate that a poorly sized catheter could otherwise block those patients that would leak using the involuntary reflex cough test, but otherwise would not leak because of the larger catheter placement and its concomitant blocking. A smaller catheter as will be discussed later is desirable in these instances to measure pressure and serve other functions. In one example, a catheter is used for bladder screen and airway protection diagnosis, while for stress incontinence determination, a catheter may not always be necessary and a pad for determining when leakage occurs is used.

A kit that is marketed for the iRCT diagnostic tool could include the nebulizer and its drug as TA in one example and one or more pads for the electrodes at the paraspinal and use with EMG. The pad may only be necessary for stress incontinence determinations. A catheter is included in another kit example for use in measuring airway and intra-abdominal pressure. In one non-limiting example, a pad can be placed on a catheter to determine urine leakage and aid in determining stress incontinence. Pressure data is sent to the handheld device in some examples. Obtaining any EMG values from the paraspinal in conjunction with the urology analysis is advantageous. It is possible in one example to measure pressure from a bladder catheter and determine at the same time EMG signals using the EMG electrodes at the L5/S1 in conjunction with the measured involuntary reflex cough test and urology catheter sensing. This is advantageous compared to placing electrodes at the perineal muscles on each side of the sphincter. The graphs in FIGS. 9 and 10 show the disadvantage of the perineal EMG where interference is obtained as shown in FIG. 9 for the perineal as compared to FIG. 10 for the L5/S1 as described above.

It has been found that EMG signals obtained from the perineal muscles have EMG activity from the non-involuntary muscles, i.e., the voluntary muscles blacking out and making analysis difficult because of the signal interference. When the electrodes are placed at the back at the L5/S1 junction, on the other hand, there is nothing else but the paraspinal muscles. It is bone below on each side at the L5/S1 junction. The electrical impulses can be obtained that determine the number of cough impulses coming down through the patient. This is accomplished even if a person has much adipose. The electrode pad used at the L5/S1 junction, in one non-limiting example, typically has an active reference and ground. A pad holds this active reference and ground and the leads as the active reference and ground are plugged into the handheld device (or wireless sensing device in another example) and transmit data to the processor. At least one catheter is also plugged into the handheld device (or wireless sensing device) and measures bladder pressures. A rectal catheter can also be used in some examples. The processor receives EMG signals and determines when the cough event is over.

The involuntary coughs are not hidden by interference when measured from the lower back at the paraspinals as described. This allows a clinician to determine coughs from the bladder when the EMG located at the L5/S1. In one aspect, the area under curve and the average pressure is determined for the cough event corresponding to the involuntary reflex cough test. When this involuntary component of the cough ends, in one example, it becomes silent EMG activity for a period of time. The pressures are at baseline for a period of time, which corresponds in one example to an inhalation. The involuntary component is over.

Sometimes with the involuntary reflex cough test, the cough occurs six times without breathing, but when the patient stops to breathe, the event is over. Using the programming applied with the processor in the handheld device, it is possible to calculate the variables inside the wave as to the involuntary cough and determine airway protection capability. Thus, it is possible to determine and measure cough by defining through appropriate data processing the involuntary cough event compared to the whole cough epoch. For example, a patient could cough ten times, but only the first four are part of the involuntary cough event. The coughs after that event are not part of the epoch.

The graphs for urologic testing in FIGS. 9 and 10 show the EMG signal component (ENG), detrusor pressure ($P_{DET}$), abdominal pressure ($P_{ABD}$) and vesicular pressure ($P_{VES}$). Obtaining the detrusor pressure is not always necessary, thus the set up may not require the rectal and urethral catheters. The analysis can be accomplished with the EMG signal component and vesicular pressure component such that apparatus used for obtaining the vesicular pressure are used. The intravesicular is often used to determine the intra-abdominal since both track closely. Data from the pressure measurements and EMG in conjunction with the involuntary cough reflex test are capable together with appropriate processing to assess for an unsafe bladder. There could be more continuous EMG activity in an unsafe bladder because that corresponds to an uninhibited muscle from a spinal cord injury or upper motor neuron injury.

As will be explained, the programming includes algorithm branches resulting in a conclusion of unsafe bladder based on the data analysis. It is possible to calculate from the waveforms information necessary for assessing airway protection ability. It should be understood that taking the EMG from the L5/S1 is also a better situation for the doctor or clinician, and the patient, since it is more acceptable in a hospital, outpatient or inpatient setting. The doctor or clinician does not have to bend down or stoop and look near the crotch area and place pads since the EMG can now be taken from the paraspinals. Also, the placement of pads and electrodes at the paraspinals is advantageous when patients are standing. If pads are placed at the perineal area, sweat and other problems could cause those pads to become loose and good signals may not be obtained. Also, it should be understood that the perineal muscles do not fire involuntarily. The sphincter may fire involuntarily, but that would create more noise as noted before. Electrodes are not placed at the vagina, but are placed at the paraspinal area instead.

This information obtained from iRct and the EMG taken at the paraspinals allows the doctor or clinician to obtain data leading directly to a diagnosis. For example, some patients that have urinary stress incontinence may have a normal airway in this analysis. It has been found by experimentation that the normal airway is about 50 centimeters water average intra-abdominal pressure. It should be understood that the vesicular pressure (bladder pressure) can track intra-abdominal pressure and terms are often similar and used together. "Bladder" or intravesicular pressure is often used to determine and equate with intra-abdominal pressure. The two are sometimes used interchangeably. Stress urinary incontinence and/or bladder physiology can be diagnosed. The system and method as described leads directly to diagnosis. Fifty centimeters average intra-abdominal pressure over time has been found to correspond to an involuntary reflex cough test normal airway. Thus, the standard deviations or other percentages from that value are used in one non-limiting example to determine an abnormal airway. In a conducted study, the actual value is determined to be about 50.6 centimeters water as compared to voluntary cough values of about 48 centimeters of water. In an outpatient setting, it is possible to have the nebulizer (and drug) and only a pad and test SUI. In hospitalized patients or inpatient settings, this combination is used to measure airway and bladder physiology and the test combination includes a catheter.

It should be understood that the involuntary cough reflex test (iRCT) gives a higher pressure average than obtained using a voluntary cough test. The involuntary cough reflex test is thus a valuable medical diagnostic tool. In one example, four variables are significant in this analysis. These variables include: (1) duration of the event; (2) average intra-abdominal pressure of the event; (3) peak intra-abdominal pressure (max) of the event; and (4) area under the curve. Using these four variables, it is possible to process the received data and obtain a specific diagnosis that could not otherwise be obtained without the use of the involuntary reflex cough test. Individual deficits in a specific variable or combination of variables are used to characterize specific diseases and problems and useful as a medical diagnostic tool.

Some specific examples obtained through experimentation follow. For example, FIG. 11 shows paired sample statistics, paired sample correlations, and paired sample tests for a neurologically normal group of 168 patients and showing the average intra-abdominal pressure (AIAP) for the voluntary cough versus the involuntary reflex cough test. FIG. 12 shows the results for the peak intra-abdominal pressure (PIAP) and FIG. 13 shows the results for the area under the curve (AUC).

Figure 14:
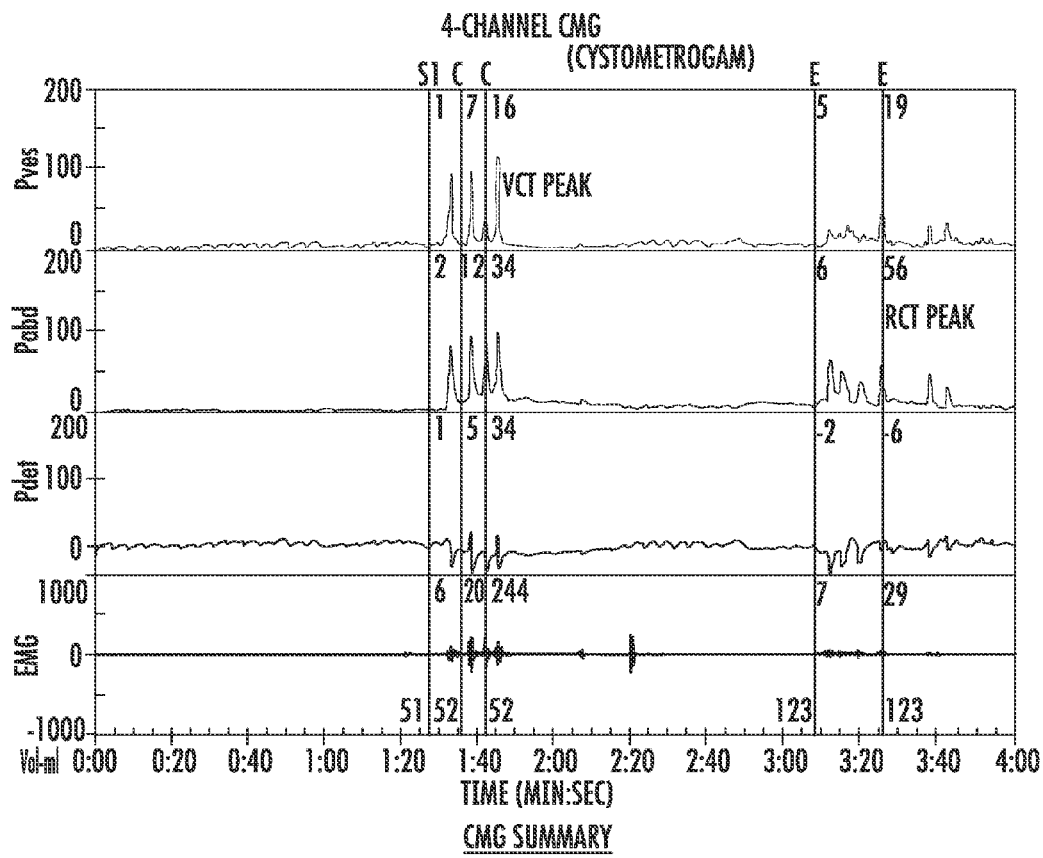
FIGS. 14-16 are graphs showing urodynamic tracings similar to those shown in FIGS. 9 and 10, for a patient with a tracheal tube removed and showing the results for the voluntary cough test (FIGS. 14 and 15) and the involuntary reflex cough test (FIG. 16).
Figure 15:
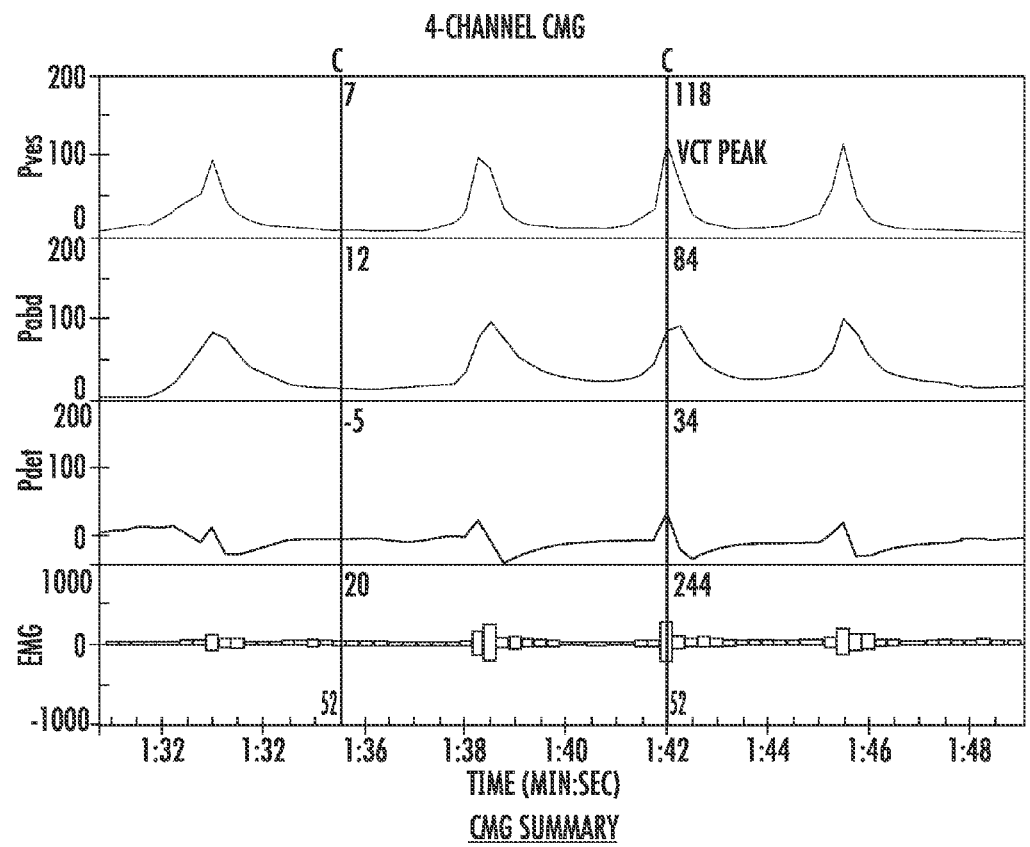
Figure 16:
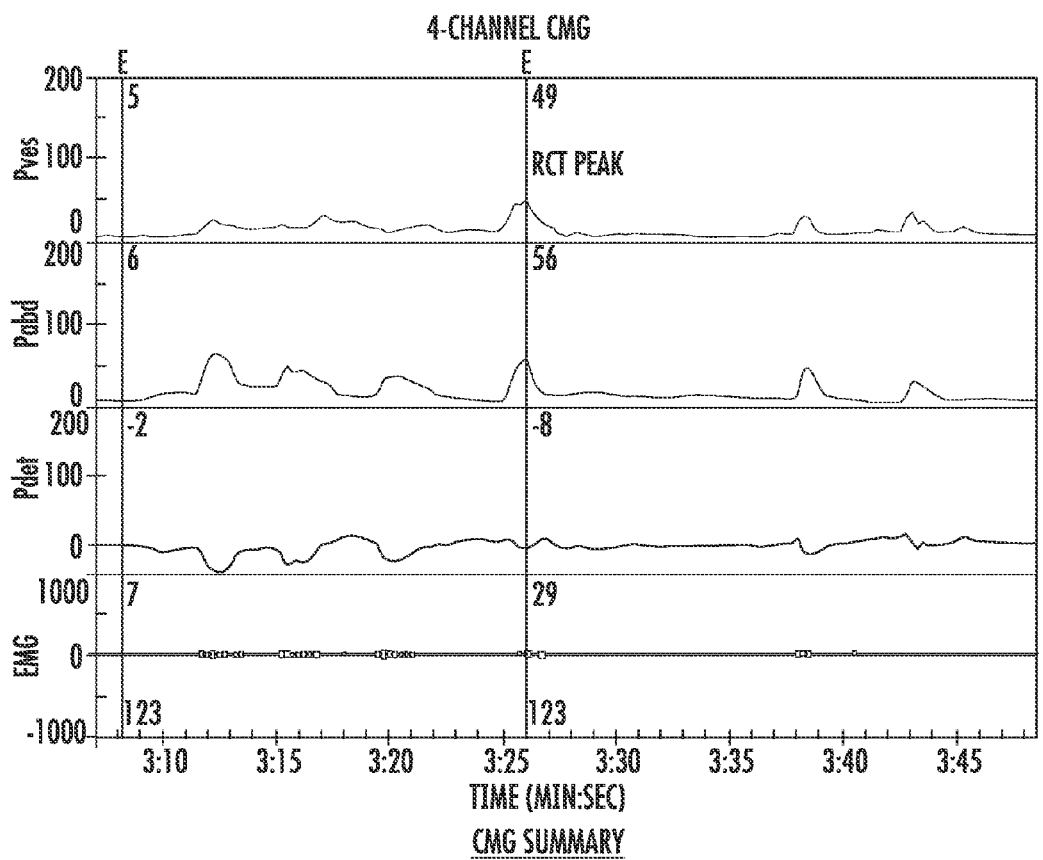

FIGS. 14-16 are graphs showing a four-channel CMG with the voluntary cough test (VCT) and the involuntary reflex cough test (iRCT) and showing the signal peaks and showing the EMG signal clarity better with the RCT than with the VCT. In the voluntary cough test, the NIF was −40, indicating the difficulty with the voluntary cough test and the advantageous use of the involuntary reflex cough test. This patient initially had a tracheal tube, which is later removed. The tracheal tube was out for the testing that was accomplished when the values shown in FIGS. 14-16 were obtained. The NIF as a negative inspiratory force of −40 (VCT) indicates a typical normal pulmonary parameter. This patient's motor reflexes, however, do not work adequately and functions shut down. During testing, this patient could be sitting for 12 seconds and have difficulty breathing and could in some cases develop acute respiratory stress syndrome or aspiration syndrome. This may require reintubation in a possible emergency situation. Otherwise, the patient could end up anoxic. It is evident that this process using the involuntary reflex cough test will help determine neurological processes (or deficits).

An analysis of the results in the tables of FIGS. 17A-17C allows a better understanding of the differences between the voluntary cough test and the involuntary reflex cough test. This provocation of cough using the involuntary reflex cough test causes urinary incontinence in subjects with SUI who do not experience urinary incontinence with voluntary cough. Alternatively, the involuntary reflex cough test does not produce urinary incontinence in healthy women without SUI. The incremental portion of subjects with a history of SUI identified in this matter are clinically useful in the diagnosis and management of SUI. This allows a determination of the Positive Predictive Value (PPV) and Negative Predictive Value (NPV) of the involuntary reflex cough test administered with urodynamic testing (some data shown in FIGS. 17A-17C). Thus, it is possible to compare urodynamic parameters obtained during a voluntary cough and during the involuntary reflex cough test.

Figure 18:
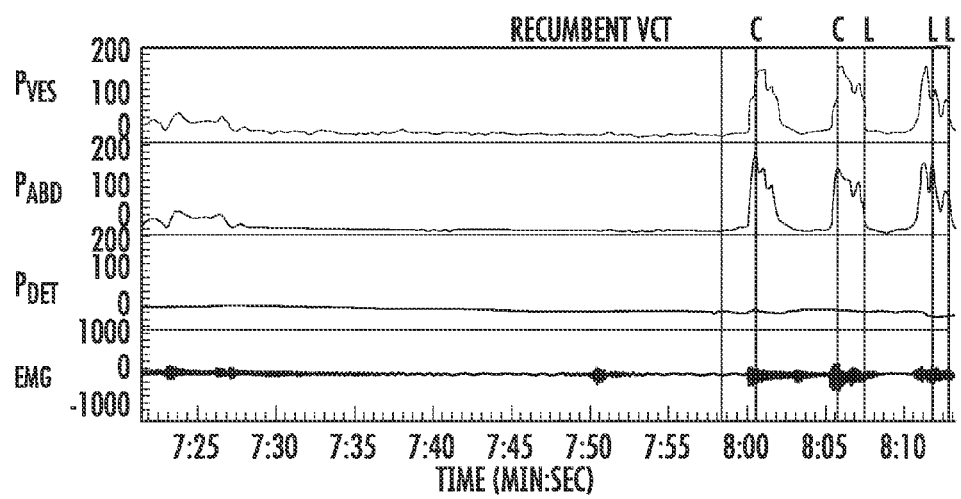
FIGS. 18 and 19 are graphs for urodynamic tests similar to those shown in FIGS. 9 and 10 and 14-16 and showing results for a recumbent patient and a voluntary cough test (FIG. 18) and an involuntary reflex cough test (FIG. 19).
Figure 19:
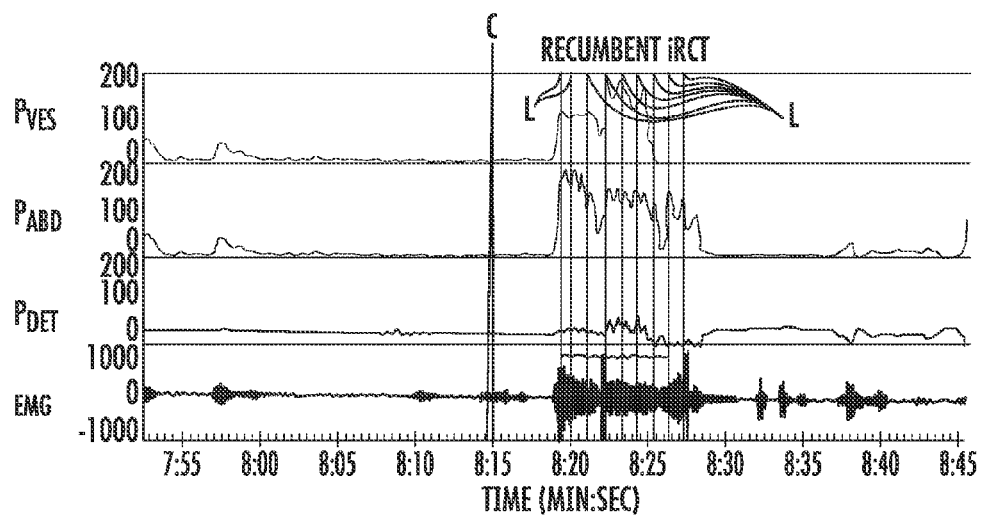

FIGS. 18 and 19 are graphs for urodynamic testing results showing data for the involuntary reflex cough as a diagnostic tool in which the involuntary reflex cough test (iRCT) visualizes or quantifies sphincter deficiencies with contrast of other quantification means. FIG. 18 shows the test results when a voluntary cough test is administered for a recumbent patient and FIG. 19 shows the test results when the involuntary reflex cough test is administered for the recumbent patient. Various lines are indicated and described below.

FIGS. 18 and 19 are graphs that show a urodynamics event in this study. The Onset to Leak (OtL) in the graph is real time (Marks under L lines below L marks). The lines with a C at the top are retrospectively placed to identify peak pressure. The subject below was classified as mild SUI (M) by the investigator after exam and entry. The OtL is recorded as seconds from pressure take-off until the observer manually pushes a button to indicate a leak is seen. The observer was blinded from the machine with a screen waist high, and the type of cough test being administered, VC vs iRCT, with noise cancelling headphones on. The observer was positioned below the waist and screen with headphones on to watch the urethral outlet and pushed the indicator line button when an observed leak was seen, which marked the timeline.

The study did not have complete uniformity among sites. One site did not mark the leaks live during the event only if there was any leak at all with one mark at the end outside the event. This site was not included in the OtL Data Tables. Another nine sites marked the events the same, during the event when leakage was seen. These are relatively accurate and come only from pushing the button and cannot be marked as a leak (L) retrospectively by the sites. The number of times the button is pushed represents the individual urine leaks seen by the observer and may vary among sites, but gives added information separating voluntary cough test and involuntary reflex cough test regarding the severity of SUI. The line and pressure take off are live and if the marks are during the event they are reasonably accurate with time lapse error from manually pushing the button. This can be repeated in a small group with automatic sensors that would mark leakage more precisely. Regardless, the evidence on the graphs shows significant differences in SUI between the voluntary cough test and involuntary reflex cough test (iRCT) for severity and mechanisms of action (MOA).

In FIG. 19, for example, iRCT, the test made the subject void, except the Detrusor Line (Pdet) is not significantly elevating during the event, which would be seen with voiding if the detrusor muscle is contracting. It appears to be stress from outside the bladder and reflects the bowel catheter symmetrically for most of the event. If the number of leaks marked and the OtL represents pathophysiology, this patient typically has at least Intrinsic Sphincter Deficiency (ISD), and thus, cannot be concluded from the leak marked on the VC event above where the OtL is 7 seconds. Inhalation probably increases resting tonic closure of the sphincters. This raises an issue whether the voluntary cough demonstrates that this inhalation activated tonic closure system works, by delaying the leak 7 seconds, while the iRCT points immediately to severe ISD (Intrinsic Sphincter Deficiency).

This is an example of why regardless if a person leaks on both voluntary cough and iRCT, it is not possible always to determine MOA or severity of SUI with voluntary cough. It is evidence of one reason overall improvement in patient outcomes and quality of life have not significantly improved despite incontinence care, especially at the general practice (GP) level. Thus, iRCT is a screening health tool useful by the GP for early identification when conservative treatment could proactively help. IRCT is also a diagnostic tool useful by the urologists to assess severity, MOA and possibly intra-operatively and assist with sling or TVT tensioning.

This same approach may work in other sphincter deficiency situations such as Lower Esophageal Sphincter (LES) and reflux. It is possible reflux laryngitis is initiated by an involuntary event, which combined with insufficiency of the closure system, leads to acid reflux which with laryngeal acid receptor activation continue the involuntary event activation and further unopposed reflux of acid. Visualization with contrast may show significant reflux differences between voluntary cough, with inhalation tonic closure reinforcement, and iRCT activated intra-abdominal pressure onset to reflux differences.

Further description concerning the involuntary reflex cough test as a diagnostic tool is now set forth. This is important not only for lower esophageal sphincter, but also for the urinary sphincter function analysis. The analysis as the chi-squared test can be accomplished by a statistician. This OtL data outcome for the voluntary cough test versus the involuntary reflex cough test is in conjunction with lunch inflation with tonic urethral and lower esophageal sphincters closure principle. This is an advantageous finding and is conclusive of why the involuntary reflex cough test is an appropriate involuntary diagnostic maneuver as a health screen tool to improve outcomes, quality of life and decrease neurological, urological and gastroenterological pathophysiology disease by improved diagnostic and measurable capabilities.

FIG. 20 shows tables for the statistical analysis (chi-squared) of the data and information. This evidence shows that leak with iRCT occurs earlier than with voluntary cough. There is some evidence that inflation of the lungs increases bladder sphincter closure and therefore might inhibit leak. Lung inflation increases abdominal pressure that tends towards leaks, which might be prevented by the additional bladder sphincter tone. Voluntary cough, unlike the iRCT, starts with an inspiration, and therefore there might be inhibition of leak in the first phase of voluntary cough. If this is so, leak should occur more frequently in the first phase (initial expiratory effort) of iRCT than in the first phase (inspiration) of voluntary cough.

Records of patients were checked in this process. Patients were located who had a leak with either voluntary cough or iRCT or both, and who had a clear indication of the timing of the leak. Each leak was labeled either as 'early' when it occurred during or immediately after the first expiratory phase of voluntary cough or iRCT, and as 'late' when it occurred during or after the second expiratory phase of voluntary cough or iRCT.

The hypothesis was that if early leak occurred more frequently with iRCT than with voluntary cough, this might be due to the leak-inhibiting mechanism in the inspiratory phase of voluntary cough, and could be a factor in explaining why time to leak (OtL) was greater with voluntary cough than with iRCT.

Records from 123 patients were analyzed. All leaked with voluntary cough or iRCT or both. Records were rejected when the leak time was not clearly identified. The distinction between early and late leak was occasionally difficult, and a 'balanced judgment' was made. Elimination of these rather uncertain timings do not change the general pattern of the analysis.

Summary Analysis:
1) 8 pts leaked early with both VC and iRCT;
2) 20 pts leaked early with iRCT and late with VC;
3) 5 pts leaked early with VC and late with iRCT;
4) 14 pts leaked early with iRCT and not at all with VC.
5) 0 pts leaked early with VC and not at all with iRCT 123 pts leaked. 42 pts leaked early with iRCT. 13 leaked early with VC.

Detailed analysis: Patients who leaked with both VC and iRCT and had late leak times for both:
612-2, 567-1, 605-1, 701-1, 519-1, 520-1, 522-1, 518-1, 539-1, 543-1, 551-1, 553-1, 562-1, 208-1, 303-1, 311-1, 315-1, 509-1, 511-1, 513-1, 1202-2, 1207-1, 1112-1, 823-1, 927-1, 812-1, 917-1, 1202-1, 716-1, 711-2, 1045-1, 1027-1
N=33

Patients who leaked with both VC and iRCT and had early leak times for both:
569-1, 616-1, 1114-1, 802-1, 1035-1, 554-1, 1014-1, 1038-1
N=8

Patients who leaked with both VC and iRCT and had late leak times for VC and early leak times for iRCT:
568-1, 516-1, 544-1, 548-1, 555-1, 556-1, 560,1, 565-1, 313-1, 1017.1, 1011-1, 1025-1, 314-1, 1204-1, 1205-1, 1117-1, 1108-1, 805-1, 809-1, 1038-1
N=20

Patients who leaked with both VC and iRCT and had early leak times for VC and late leak times for iRCT:
1104-1, 1206-1, 934-1, 1001-2, 707-2
N=5

Patients who did not leak with VC and had early leak times with iRCT:
540-1, 564-1, 567-1, 1203-2. 1102-1, 1106-1, 926-1, 921-1, 1021-1, 1043-1, 1029-1, 1019-1, 1012-1, 313-1
N=14

Patients who did not leak with VC and had late leak times with iRCT:
549-1, 559-1, 517-2, 606-1, 531-1, 535-1, 536-1, 537-1, 547-1, 550-1, 552-1, 561-1, 510-1, 1208-1, 1119-1, 1120-1, 1107-1, 1111-1, 930-1, 823-1, 804-1, 702-1, 1003-1, 712-

1, 717-1, 718-1, 719-1, 708-1, 701-1, 1040-1, 1041-1, 1046-1, 1036-1, 1015-1, 1008-1, 1009-1, 1006-1, 1048-2
N=38
Patients who did not leak with iRCT but who had late leak times with VC:
611-2, 530-1, 310-1, 505-1, 820-1
N=5
Patients who did not leak with iRCT but who had early leak times with VC:
N=0
Summary:
1) 123 pts were assessed. They all leaked with either VC or iRCT or both. Thus potentially there could be 246 leaks. In fact there were 189 since some pts did not leak on both tests.
2) 118 pts leaked with iRCT (96%); 71 leaked with VC (58%); 66 (54%) leaked with both.
3) 66 pts leaked with both VC and iRCT. 28 of them (42%) had early leak times for iRCT. 13 (20%) had early leak times for VC. (8, 12%, had both.) 33 pts (50%) had only late leak times.
4) 52 pts leaked only with iRCT; 14 (27%) had early leak times.
5) 5 pts leaked only with VC; none (0%) had an early leak.

FIGS. 21 and 22 are graphs showing urodynamic tracings of a test series with a forceful voluntary cough in a female subject. FIG. 21 shows the results with the female subject who does not have a history of SUI. FIG. 22 shows the results with the female subject who has moderate/severe SUI. The voluntary cough and involuntary cough reflex test are shown. The urinary bladder is filled with 200 milliliters of saline and intravesicle and rectal pressure catheters are used in this example. In FIG. 22, it shows that the voluntary cough did not elicit SUI despite a series of vigorous individual consecutive inhalation voluntary cough efforts.

As noted before, voluntary cough (VC) and the laryngeal expiratory reflex (LER) as elicited by an involuntary reflex cough test (iRCT), using a nebulized 20% tartaric acid solution, have distinctly different neurophysiological mechanisms. Voluntary cough is classically defined as an event that starts with an inspiration that leads to lung inflation. As the lungs inflate during inspiration, there is a corresponding increase in the tonicity of both the urethral sphincter (US) and lower esophageal sphincter (LES) (as shown in FIG. 21).

There is increased tonicity of the US and LES with lung inflation. Increased sphincter tonicity is a patterned motor event, which facilitates US and LES closure during increases in intra-abdominal pressure (IAP) that commonly occurs following lung inflation, i.e., the inspiratory phase of voluntary cough. The LER does not have a significant lung inflation phase prior to the series of expiratory coughs. As such, increased IAP can cause stress urinary incontinence (SUI) or gastroesophageal reflux (GER) to occur due to inadequate closure of these sphincters in subjects who have Intrinsic Sphincter Deficiency (ISD) (as shown in FIG. 22).

There now follows a description of what occurs as part of as part of normal lung inflation with inhalation as it relates to sphincter increased tonicity and closure for both urethral (US) and lower esophageal sphincter (LES) before Voluntary Cough. The Hering-Breuer inflation reflex (H-B Reflex) cannot be activated with iRCT because lung inflation does not occur. Airway protection from a perceived stimulus that could be perceived as life threatening by the body short circuits all the reflexes that are connected to the H-B Reflex system by causing vocal cord closure in 14 msecs, and in about 20 msecs IAP elevation occurs without the additional sphincter tonicity closure that would occur reflexively with inhalation lung inflation.

The involuntary reflex cough test causes significant diaphragm elevation with iRCT that does not occur with voluntary cough because the H-B Reflex, in part, holds the diaphragm down with the closed LES, despite quite highly elevated intra-abdominal pressure. The diaphragm is not held down with the iRCT, the diaphragm elevation actually pulls the LES up with it causing partial gastric content reflux. The reflux causes a vicious cough/reflux cycle to occur that leads to insidious diseases like GERD, COPD, laryngitis, Barret's Esophagitis, heartburn and similar problems. The same involuntary maneuver using the involuntary reflex cough test will diagnose SUI by blocking the inhalation tonicity that would possibly come from lung inflation via H-B Reflex.

The Hering-Breuer inflation reflex is a reflex triggered to prevent overinflation of the lungs. Pulmonary stretch receptors present in the smooth muscle of the airways respond to excessive stretching of the lung during large inspirations. Once activated, they send action potentials through large myelinated fibers of the paired vagus nerves to the inspiratory area in the medulla and apneustic area of the pons. In response, the inspiratory area is inhibited directly and the apneustic area is inhibited from activating the inspiratory area. This inhibits inspiration, allowing expiration to occur.

Josef Breuer and Ewald Hering reported in 1868 that a maintained distention of the lungs of anesthetized animals decreased the frequency of the inspiratory effort or caused a transient apnea. The stimulus was therefore pulmonary inflation.

The neural circuit that controls the Hering-Breuer inflation reflex involves several regions of the central nervous system, and both sensory and motor components of the vagus nerve. Increased sensory activity of the pulmonary-stretch lung afferents (via the vagus nerve) results in inhibition of the central inspiratory drive and thus inhibition of inspiration and initiation of expiration. The lung afferents also send inhibitory projections to the cardiac vagal motor neurones (CVM) in the nucleus ambiguus (NA) and dorsal motor vagal nucleus (DMVN). The CVMs, which send motor fibers to the heart via the vagus nerve, are responsible for tonic inhibitory control of heart rate. Thus, an increase in pulmonary stretch receptor activity leads to inhibition of the CVMs and an elevation of heart rate (tachycardia). This is a normal occurrence in healthy individuals and is known as sinus arrhythmia.

Early physiologists believed the reflex played a major role in establishing the rate and depth of breathing in humans. While this may be true for most animals, it is not the case for most adult humans at rest. However, the reflex may determine breathing rate and depth in newborns and in adult humans when tidal volume is more than 1 L, as when exercising.

The Hering-Breuer deflation reflex serves to shorten exhalation when the lung is deflated. It is initiated either by stimulation of stretch receptors or stimulation of proprioceptors activated by lung deflation. Like the inflation reflex, impulses from these receptors travel afferently via the vagus. Unlike the inflation reflex, the afferents terminate on inspiratory centers rather than the pontine apneustic center. These reflexes appear to play a more minor role in humans than in non-human mammals.

FIG. 21 shows a graph for an urodynamic tracing of a series of tests and a forceful voluntary cough in a normal female subject with a urinary bladder filled with 200 ml of saline. There is no evidence of SUI, i.e., urine leakage, during the series of voluntary cough or the five-cough (C5) iRCT stimulus. With the iRCT the episode can have an average duration of 14.8 seconds and consists of an average of 5 expiratory coughs, during which there is no significant inhalation or lung inflation to activate US and LES tonicity. This subject is continent without the facilitatory effect of increased tonicity associated with lung inflation.

FIG. 22 is a graph for an urodynamic tracing of a series of tests and a forceful voluntary cough in a female subject, who has moderate/severe SUI. Voluntary cough did not elicit urinary incontinence despite the series of vigorous individual consecutive inhalation voluntary cough efforts. The iRCT caused immediate SUI with multiple leakages (lines indicated at 22a) during the 26-second involuntary event.

The discrepancy between the voluntary cough and iRCT in demonstrating SUI is due to the facilitatory effect of increased tonicity associated with lung inflation in voluntary cough. The voluntary cough in FIG. 22 had a similar robust peak IAP and much greater average IAP than the iRCT in this subject. The SUI was not a result from any differences in IAP or cough duration, but was secondary to the absence of the facilitatory effect of increased tonicity associated with lung inflation.

The laryngeal expiratory reflex (LER) is normally triggered when food, fluid or secretions enter the larynx during swallowing or inspiration. Reflex cough can be triggered by aspiration of food or fluid during inspiration acid reflux stimulation of laryngeal receptors or post-nasal drip into the larynx, laryngeal inflammation or infection. Although the studies on gastroesophageal reflux (GER) claim that cough is a result of gastric acid reflux, it is believed that involuntary cough is the direct cause of GER and this may lead to a previously unrecognized cycle where cough causes reflux that produces the cough associated with GER. This infers that instead of treating the cough, steps should be clinically taken to reduce the reflux. SUI is primarily caused by cough. The type of cough that causes SUI is an involuntary cough and not voluntary cough, thus, by decreasing stimuli exposure, i.e., reflux that can trigger involuntary cough, SUI could be reduced. The more comprehensive clinical approach using the involuntary maneuver, i.e., iRCT, will improve the identification of both SUI and GER when they can still be effectively and conservatively treated before the development of significant comorbidities.

Intrinsic sphincter deficiency (ISD) may be clinically present as SUI and GER. The iRCT is clinically useful in improved evaluation of LES function and a more realistic assessment of SUI.

There now follows a description of a method that can be used for processing urodynamic data obtained during the iRCT and processed in the handheld device in accordance with non-limiting examples. FIGS. 23-26 are more detailed flowcharts showing this example of various steps that can be used for obtaining and processing data received from the involuntary reflex cough text (iRTC) for stress urinary incontinence.

Figure 23:
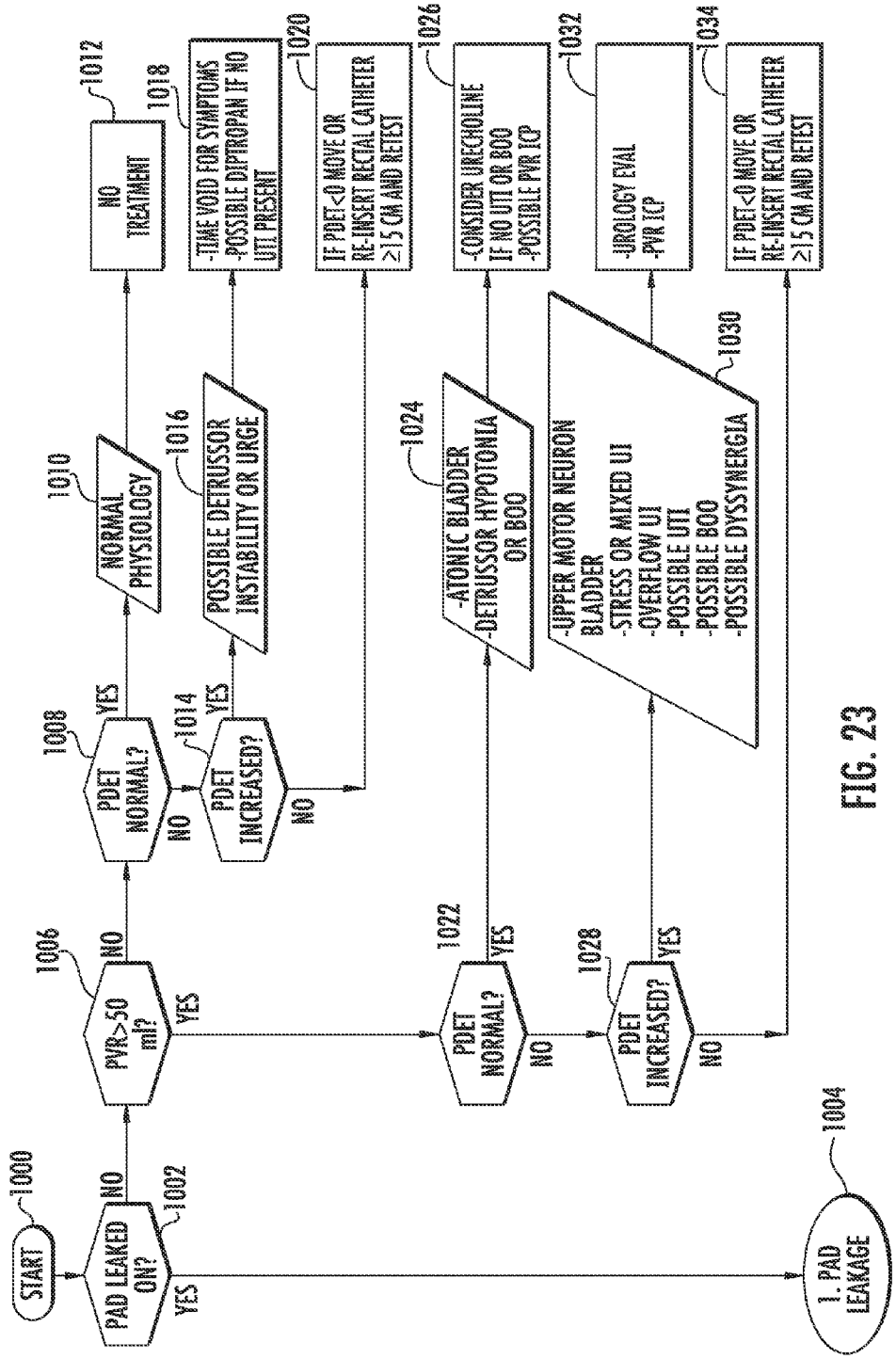
FIGS. 23 and 24 are flowcharts showing an example of a method for processing data obtained during the involuntary reflex cough test for a patient in an outpatient setting.
Figure 24:
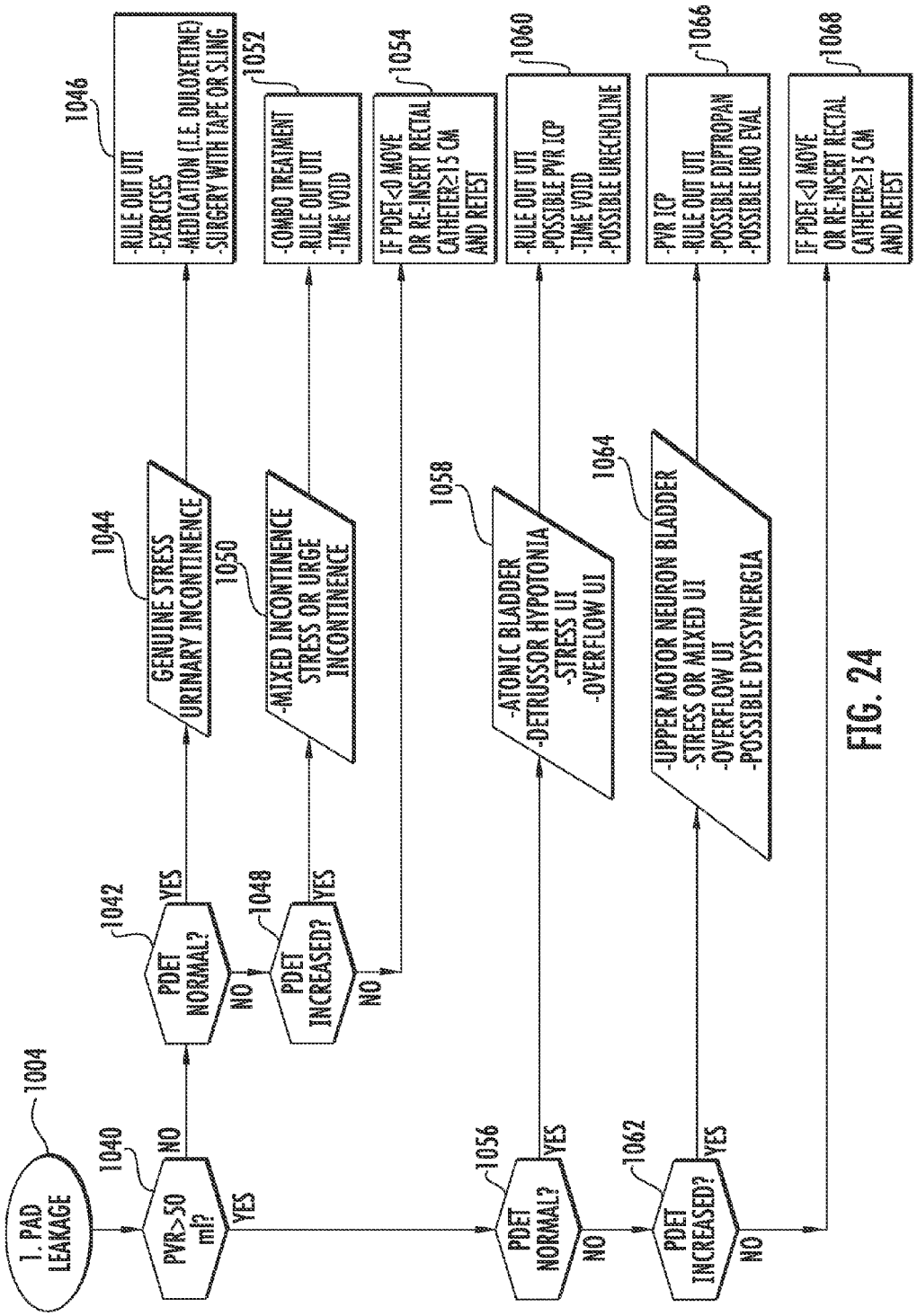

The process starts (1000) with the involuntary reflex cough test and proceeds from this test. One activity that may be pre-involuntary reflex cough test is an ultrasound to determine the starting bladder volume. It should be understood that FIGS. 23 and 24 are representative for an outpatient setting. In this outpatient example shown in FIGS. 23 and 24, it typically is about at least 200 ml starting. With the inpatient example shown in FIGS. 25 and 26, the doctor or technician waits until the patient feels the urge to void and then performs the ultrasound to measure the starting volume. There are some reasons for the differences, but neither requires bladder filling initially.

As shown in FIGS. 23 and 24 for the outpatient example, the process starts (1000) with the involuntary reflex cough test, also termed the induced reflex cough test. A determination is made if the pad is leaked on (1002) and if yes, then the sequence shown in FIG. 24 for pad leakage is followed (1004). If not, a determination is made if the post-void residual is greater than 50 ml (1006). If not, a determination is made if the detrusor pressure is normal (or elevated) (1008). Detrusor pressure is a difference between bladder and abdominal pressure and also uses a catheter in the rectum. If yes, then there is normal physiology (1010) and no treatment (1012). If not, then a determination is made whether the detrusor pressure is increased (1014) and if yes, then there is possible detrusor instability or urge (1016). This could be contractions. A course of action is a time void for symptoms and possible Diptropan if no urinary tract infection (UTI) is present (1018). If the detrusor pressure was not increased, and the detrusor pressure is less than zero, then any rectal catheter as used can be moved or reinserted an amount greater than or equal to 15 centimeters and then retest (1020). For example, the abdominal pressure is reading higher than the bladder pressure, obtaining a negative detrusor value. This could indicate that something is wrong and the catheter is not placed correctly.

If the post-void residual is greater than 50 ml, then a determination is made if the detrusor pressure is normal (1022). If yes, this could signify atonic bladder, detrusor hypotonia, or bladder outlet obstruction (BOO) (1024). Urecholine can be considered and possible post-void residual (PVR) intermittent catheterization procedure (ICP) in which the catheter is placed in the patient to drain the bladder (1026).

If the detrusor pressure was not normal, then a determination is made whether the detrusor pressure was increased (1028). If yes, this could signify an upper motor neuron bladder, stress or mixed urinary incontinence, overflow urinary incontinence, possible urinary tract infection, possible bladder outlet obstruction, and possible dyssynergia (1030). This can be followed by a urology evaluation and PVR/ICP corresponding to a post-void residual and intermittent catheterization procedure (1032). The possible dyssynergia (1030) corresponds to bladder sphincter dyssynergia also termed detrusor sphincter dyssynergia (DSD) in some non-limiting examples as a neurological condition with a contraction of the bladder musculature as not coordinated with the relaxation of the sphincter. In some of these instances, instead of the urethra completely relaxing during voiding, it may dyssynergically contract causing the flow to be interrupted and the detrusor pressure to rise. On cystography, there is typically an irregular appearance of a bladder outline because of musculature contraction against the unrelaxed bladder sphincter. Usually individuals with this type of condition may have daytime and night-time wetting and a history of urinary tract infections (UTI).

If the detrusor pressure is not increased, then recatheterization can occur if the detrusor pressure is less than zero and a rectal catheter can be moved or reinserted greater or equal to about 15 centimeters and retested in this non-limiting example (1034).

In one of these outcomes, the atonic bladder typically corresponds to a large dilated urinary bladder that does not empty, usually because of the disturbance of innervation or chronic obstruction. This could require a primary caregiver or other medical professional to consider urecholine if there is no urinary tract infection (UTI) or BOO (such as in 1026). A possible PVR ICP could be considered. Urecholine, of course, is also termed bethanechol as a parasympathetomimetic choline ester that stimulates the muscarinic receptors with further selectivity for M3 receptors without any effect on nicotinic receptors.

Diptropan as a generic oxybutynin is typically used to reduce muscle spasms of the bladder and urinary tract and treat symptoms of the overactive bladder causing frequent or urgent urination, incontinence as urine leakage and increased night-time urination.

FIG. 24 shows the pad leakage (1004) sequence. A determination is made if the post-void residual is greater than 50 ml if there was pad leakage (1004). If not, a determination is made if the detrusor pressure was normal (1042) and if yes, this indicates genuine stress urinary incontinence (1044). As an outcome, urinary tract infection is ruled out and exercises can be described and medication such as Duloxetine and possible surgery with tape or sling (1046). If the detrusor pressure is not normal, a determination is made if the detrusor pressure was increased (1048) and if yes, this could indicate mixed incontinence and stress or urge incontinence (1050). As an outcome, there could be a combination treatment. Urinary tract infection is ruled-out and possible time void (1052). If the detrusor pressure is not increased and the outcome of testing is such that the detrusor pressure is less than zero, the rectal catheter can be reinserted greater than or equal to about 15 centimeters and retesting occurs (1054).

If in these steps the post-void residual is greater than 50 ml, a determination is made if the detrusor pressure is normal (1056). If yes, this could be a sign of atonic bladder, detrusor hypotonia, stress urinary incontinence or overflow urinary incontinence (1058). Again, urinary tract infection is ruled out and a possible PVR/TCP with a time void and possible urecholine (1060).

If the detrusor pressure was not normal, a determination is made if the detrusor pressure was increased (1062), and if yes, this could signify upper motor neuron bladder, stress or mixed urinary incontinence, overflow urinary incontinence, or possible dyssynergia (1064). The outcome is a PVR/ICP, the rule-out of UTI, possible diptropan, and possible urological evaluation (1066). If the detrusor pressure was not increased and is less than zero, an outcome is to move or reinsert the rectal catheter, greater than or equal to about 15 centimeters and retest in a non-limiting example (1068).

Figure 25:
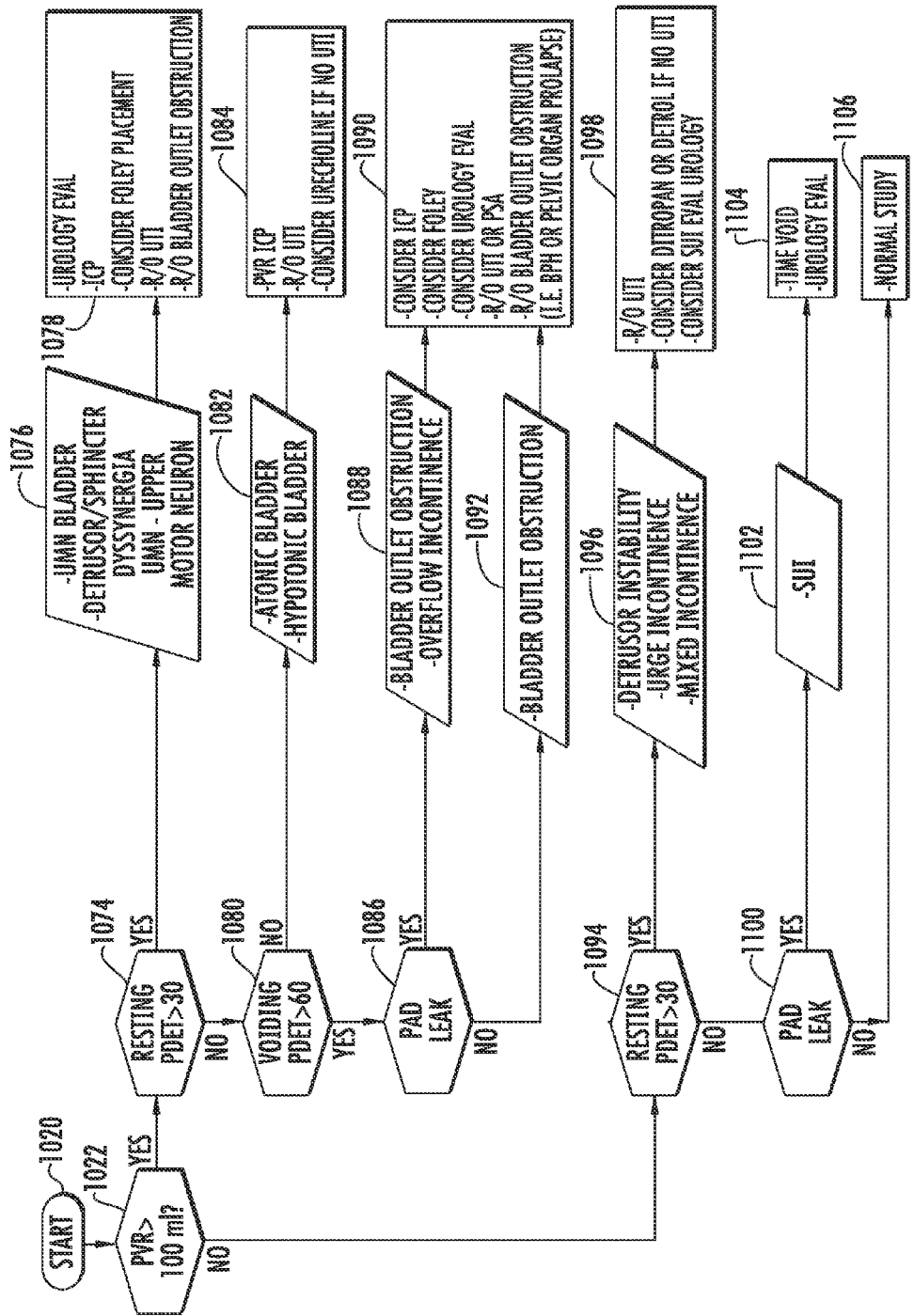
FIGS. 25 and 26 are flowcharts showing examples of a method for processing data obtained during the involuntary reflex cough test for a patient in an inpatient setting.
Figure 26:
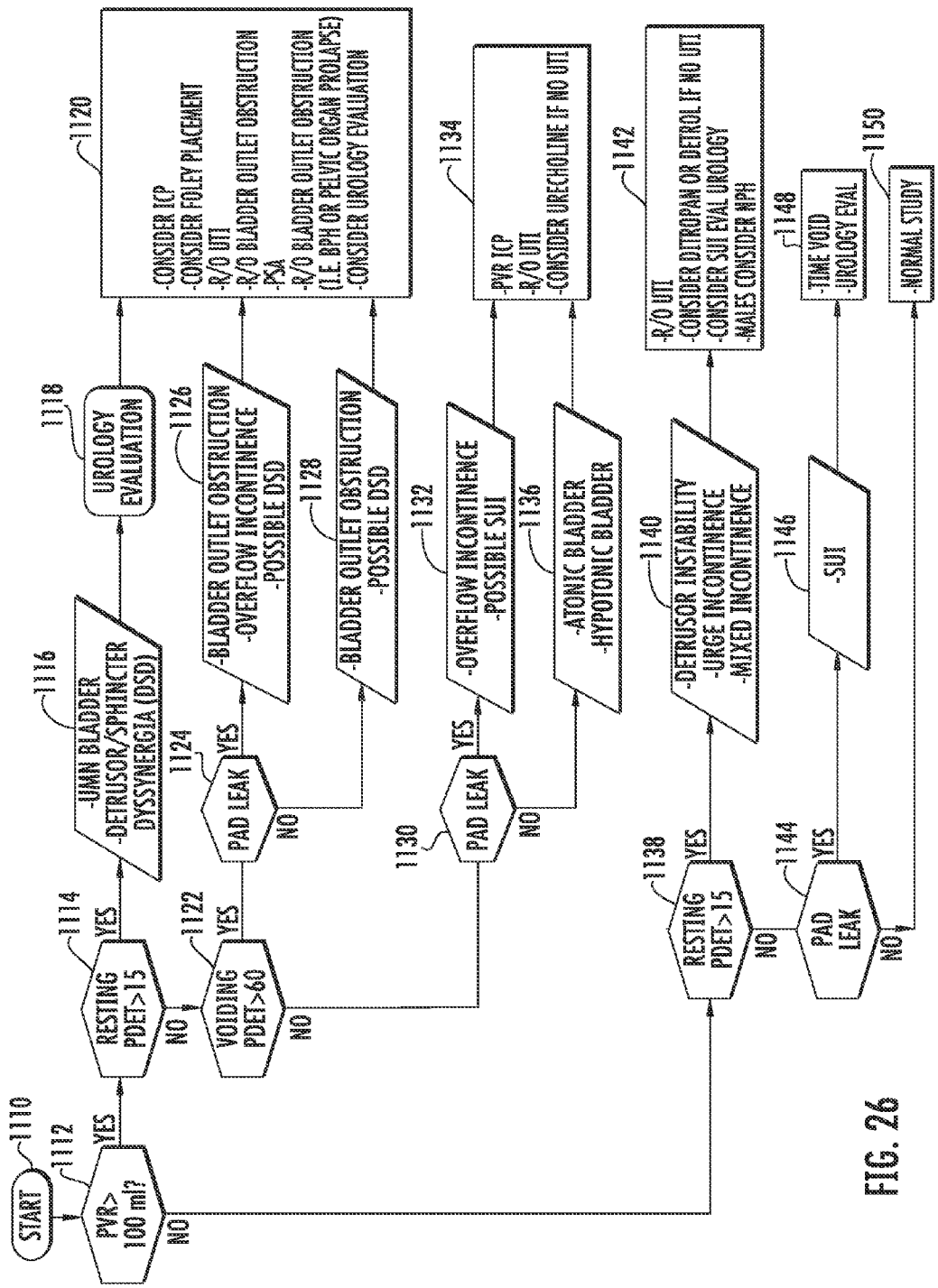

FIGS. 25 and 26 show a flow sequence similar to that shown in FIGS. 24 and 25, but in this example, the sequence is for inpatient testing. The process starts (1070) and a determination is made whether the post-void residual is greater than 100 ml (1072). If yes, then a determination is made whether the resting destrusor pressure is greater than 30 centimeters of water (1074). If yes, this could correspond to the upper motor neuron (UMN) bladder and detrusor/sphincter dyssynergia (1076). At this time, a urology evaluation can occur and ICP (intermittent catheterization procedure). The clinician can consider a Foley catheter placement. Urinary tract infection is ruled out and bladder outlet obstruction (BOO) is ruled out (1078). If the detrusor pressure was not greater than 30 centimeters of water at resting, then a determination is made whether voiding and detrusor pressure was greater than 60 (1080). If not, this can signify the atonic bladder or hypotonic bladder (1082) and the outcome can be PVR/ICP and the UTI ruled out. If there is no UTI, then urecholine is considered (1084).

If the voiding and detrusor pressure is greater than 60, then a determination is made whether the pad leaked (1086). If yes, this can correspond to bladder outlet obstruction and overflow incontinence (1088). Possible considerations can be the ICP, a Foley catheter, a urology evaluation. UTI is ruled out or prostate (PSA). The clinician also rules out bladder outlet obstruction, i.e., BPH or pelvic organ prolapse (10%). If there is no pad leak, this could possibly correspond to bladder outlet obstruction (1092) and the same outcome processing occurs (1090).

If the initial PVR was not greater than 100 ml, a determination is made if the detrusor pressure was greater than 30 centimeters of water at rest (1094). If yes, this can correspond to detrusor instability, urge incontinence and mixed incontinence (1096). UTI is ruled out and possible Ditropan or Detrol is considered if there is no UTI. A stress urinary incontinence evaluation in urology is considered at this time (1098). If the detrusor pressure was not greater than 30 centimeters of water, then a determination is made whether the pad leaked (1100), and if yes, this step corresponds to stress urinary incontinence (1102) and a time void or urology evaluation considered (1104). If there is no pad leakage, then a normal study is considered (1106).

FIG. 26 shows a preferred sequence of steps for inpatient processing as compared to that sequence shown in FIG. 25. Some of the sequence steps are similar as shown in FIG. 25. The process starts (1110) and a determination is made if the post void residual is greater than 100 ml (1112). If yes, a determination is made if the resting detrusor pressure is greater than 15 centimeters of water (1114). In this example, if yes, it could signify UMN Bladder or DSD (1116). A urology evaluation occurs (1118) and an outcome considers ICP, Foley catheter placement, ruling out UTI, ruling out bladder outlet obstruction, possible PSA, ruling out bladder outlet obstruction as BPH or pelvic organ prolapse, and considering urology evaluation as indicated (1120). If the voiding detrusor pressure was greater than 60 (1122), a determination is made if there was a pad leak (1124) and if yes, this could correspond to bladder outlet obstruction, overflow incontinence or possible DSD (1126) and the outcome is similar as before (1120). If there is no pad leakage, this can correspond to bladder outlet obstruction and possible DSD (1128) and the same outcome (1120).

If the detrusor pressure was greater than 60 ml at voiding, a determination is made if there is a pad leak (1130) and if yes, this can correspond to overflow incontinence and possible SUI (1132). The outcome can be PVR/ICP, the rule out of UTI, and urecholine if no UTI (1134). If there is no pad leakage, this can correspond to atonic bladder followed by hypotonic bladder consideration (1136). The outcome is as before (1134).

If the PVR was not greater than 100 ml (1112), a determination is made if the detrusor pressure is greater than 15 centimeters of water at resting (1138) and if yes, this can correspond to detrusor instability, urge incontinence and mixed incontinence (1140). UTI is ruled out. Ditropan or detrol is considered if there is no UTI. An SUI evaluation for urology is considered. Males can consider normal pressure hydrocephalus (MPH) (1142).

If the detrusor pressure was not greater than 15 centimeters of water at resting (1138), a determination is made whether there was a pad leak (1144) and if yes, this can correspond to SUI (1146) and the outcome can be a time void and urology evaluation with the time void indicating how much time it takes to void (1148). If not, then a normal study occurs (1150).

As shown by the different considerations and outcomes in FIGS. 23-26, many different possible tests and diagnoses with potential outcomes are possible and the sequence of steps takes the clinician through what is possible. Typically, the data is input into the handheld device and processed with the different scenarios and outcome and an evaluation displayed on the handheld device.

Figure 27:
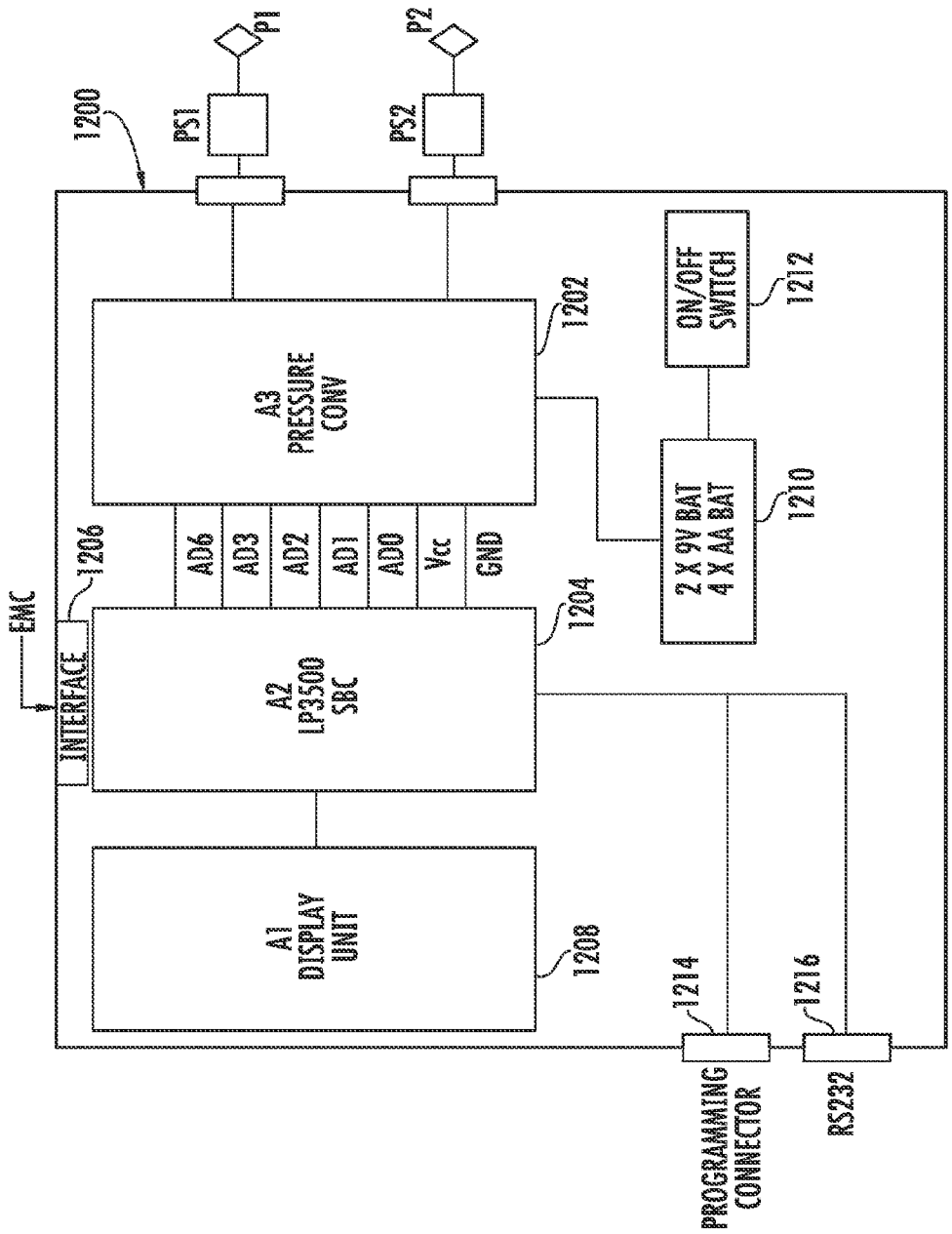
FIG. 27 is a block diagram showing various components that can be used in an embodiment of the handheld device such as described before relative to FIG. 5.

FIG. 27 is a high-level block diagram of basic components for the handheld device illustrated generally in this example at 1200, which in one non-limiting example, uses wireless technology to receive pressure readings such as shown in FIG. 8. This example relative to FIG. 27 shows a wired connection. In this example for the handheld device 1200, the device includes two pressure inputs, for example, to receive Viking connector receptacles and connect to TDOC pressure sensors. As illustrated, the inputs at pressure 1 and pressure 2 correspond to the two respective catheters as inputs through the pressure sensors PS1 and PS2 into a pressure converter circuit 1202, which transmits the pressure signals to the onboard processor 1204 through various AD signal lines as indicated. The pressure converter circuit 1202 includes pressure measurement electronics such as shown in the schematic circuit diagram of FIG. 30 and described in greater detail below. The pressure measurements obtained through the pressure sensors PS1 and PS2 are converted and forwarded to the processor 1204, which in one non-limiting example, is a single board computer such as a Rabbit LP3500. The pressure sensors PS1 and PS2 are in one non-limiting example TDOC-4030 pressure sensors. The catheters used at inputs P1 and P2 correspond in one non-limiting example to TDOC-6F catheters. It should be understood that EMC signals are input through interface circuit 1206 into the processor 1204. Data that is processed is displayed using a display unit 1208 such a display/keyboard/LED, for example a rabbit KDU.

It should be understood that the improved catheter as described below FIG. 31 can be used. In one non-limiting example, the pressure converter circuit 1202 is powered by two nine-volt batteries or in an alternative embodiment by four AA batteries 1210. The batteries are connected to an on/off switch 1212. A programming connector 1214 and RS232 connector 1216 are connected into the processor 1204 to allow programming of the processor with appropriate software and code as described before and for processing data related to the involuntary reflex cough test. Data can be retrieved or input. This device 1200 accomplishes both SUI and neuroanalysis using the appropriate data analysis.

FIGS. 28A-28D are respective plan, front elevation and side elevation views of a housing 1220 that can incorporate the various system components such as shown in FIG. 27 and form the handheld device as described before. The left side elevation view in FIG. 20C shows openings 1222 for receiving Viking connector receptacles that connect to TDOC pressure sensors for the two catheters in this non-limiting example. Of course, during handheld device use, only one catheter has to be used as noted before and is some instances only EMC.

Figure 28:
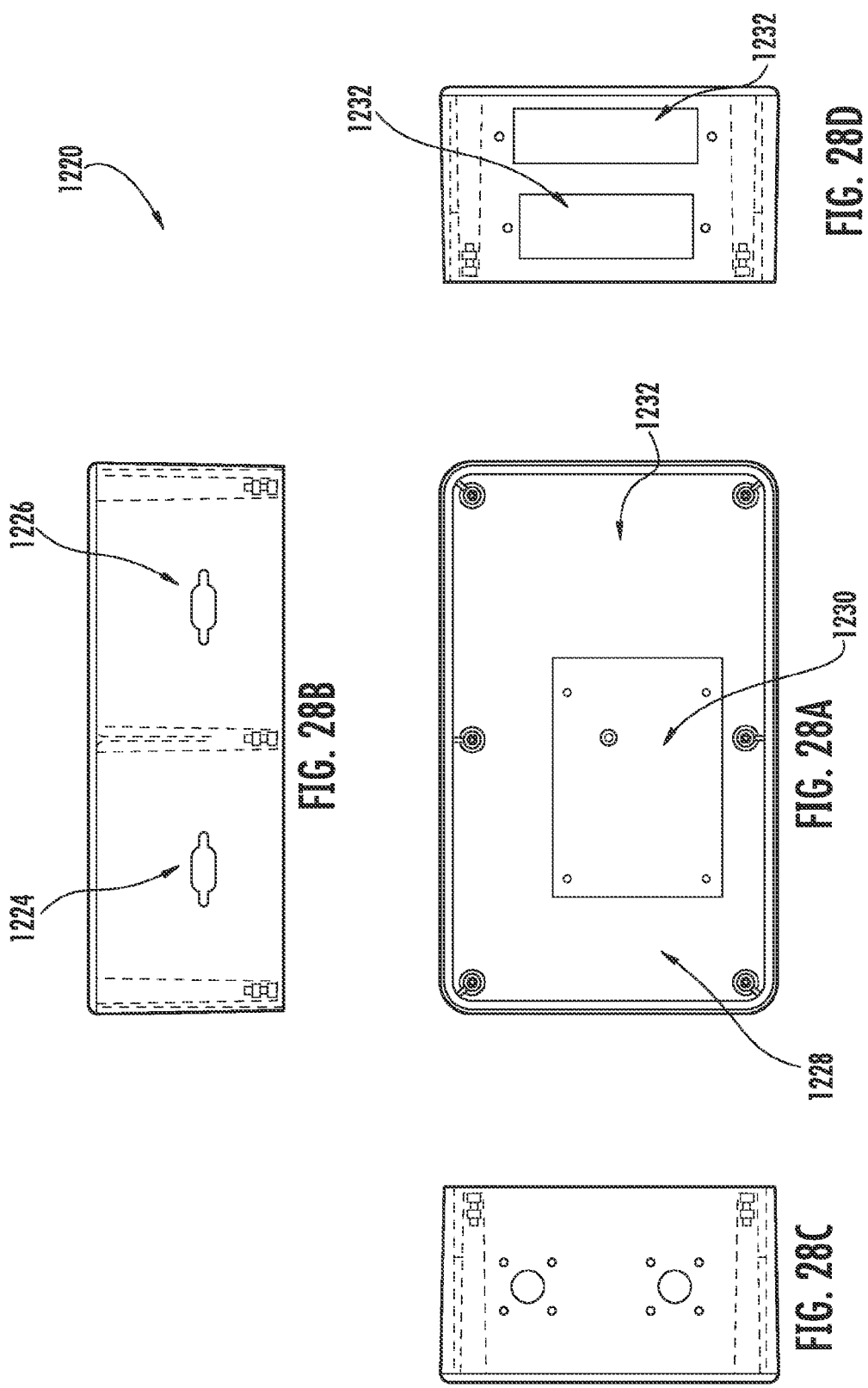
FIGS. 28A-28D are respective top, front elevation and side elevation views for the case or housing that can be used for the handheld device in accordance with a non-limiting example.

FIG. 28B shows the front elevation view with a programming connector opening 1224 for a nine pin D male connection and the RS232 connector opening 1226 for a nine pin D female in one non-limiting example. The plan view shows enough space and volume to include switch and pressure sensor wiring 1228 and a single board computer 1230 and custom pressure sensor card as described below. The side elevation view and plan view show various battery holder areas 1232 for either a 2.9 volt or a four AA battery holder.

Figure 29:
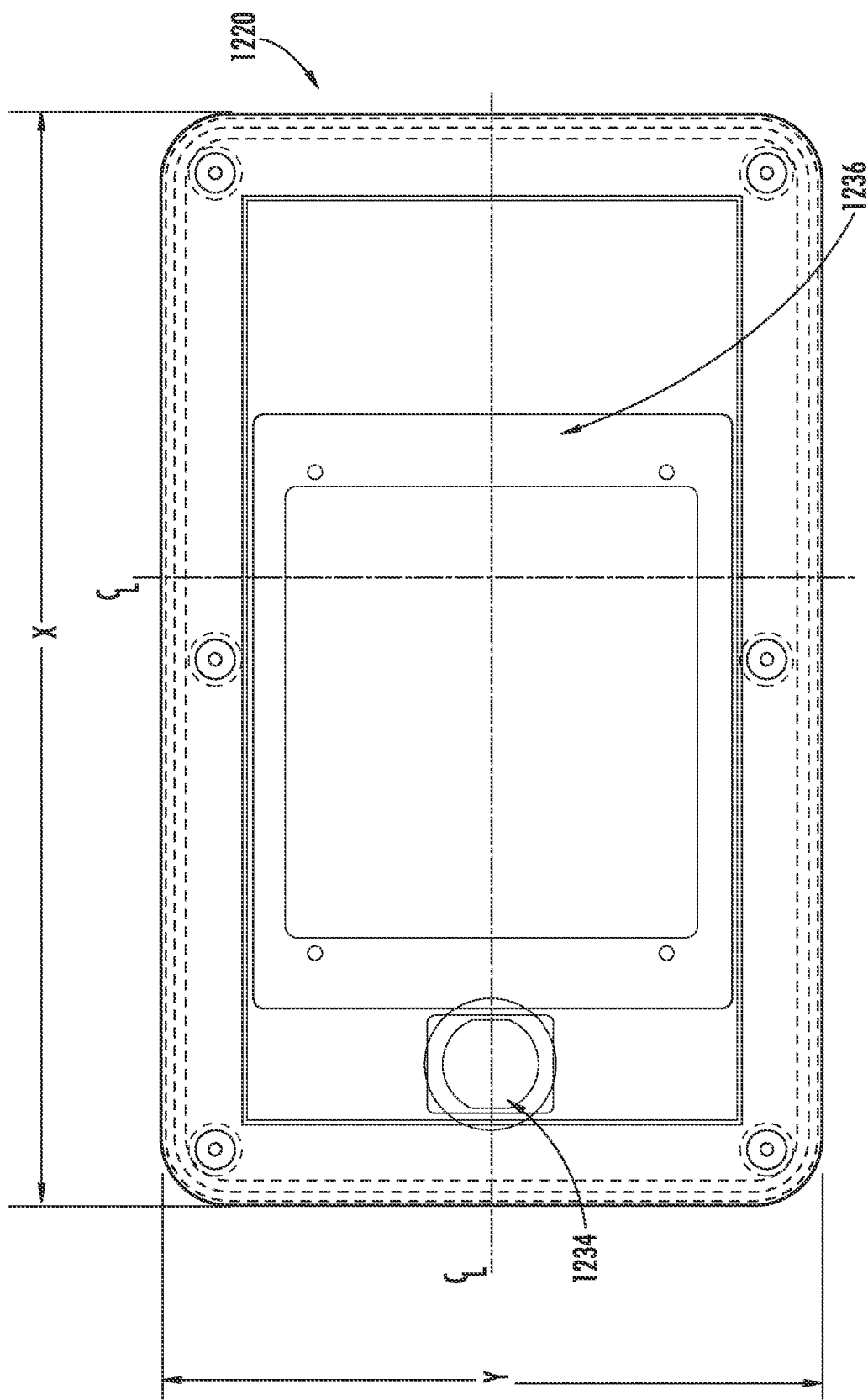
FIG. 29 is a top plan view of a housing cover of the handheld device in accordance with a non-limiting example.

FIG. 29 is a top plan view of the housing 1220 for the handheld device and showing a location for a power on/off toggle switch 1234 and a display with a keyboard and light emitting diodes (LED's) 1236. Non-limiting examples for possible dimensions for the handheld device are about 8 inches (x) and 5 inches (y).

Figure 30:
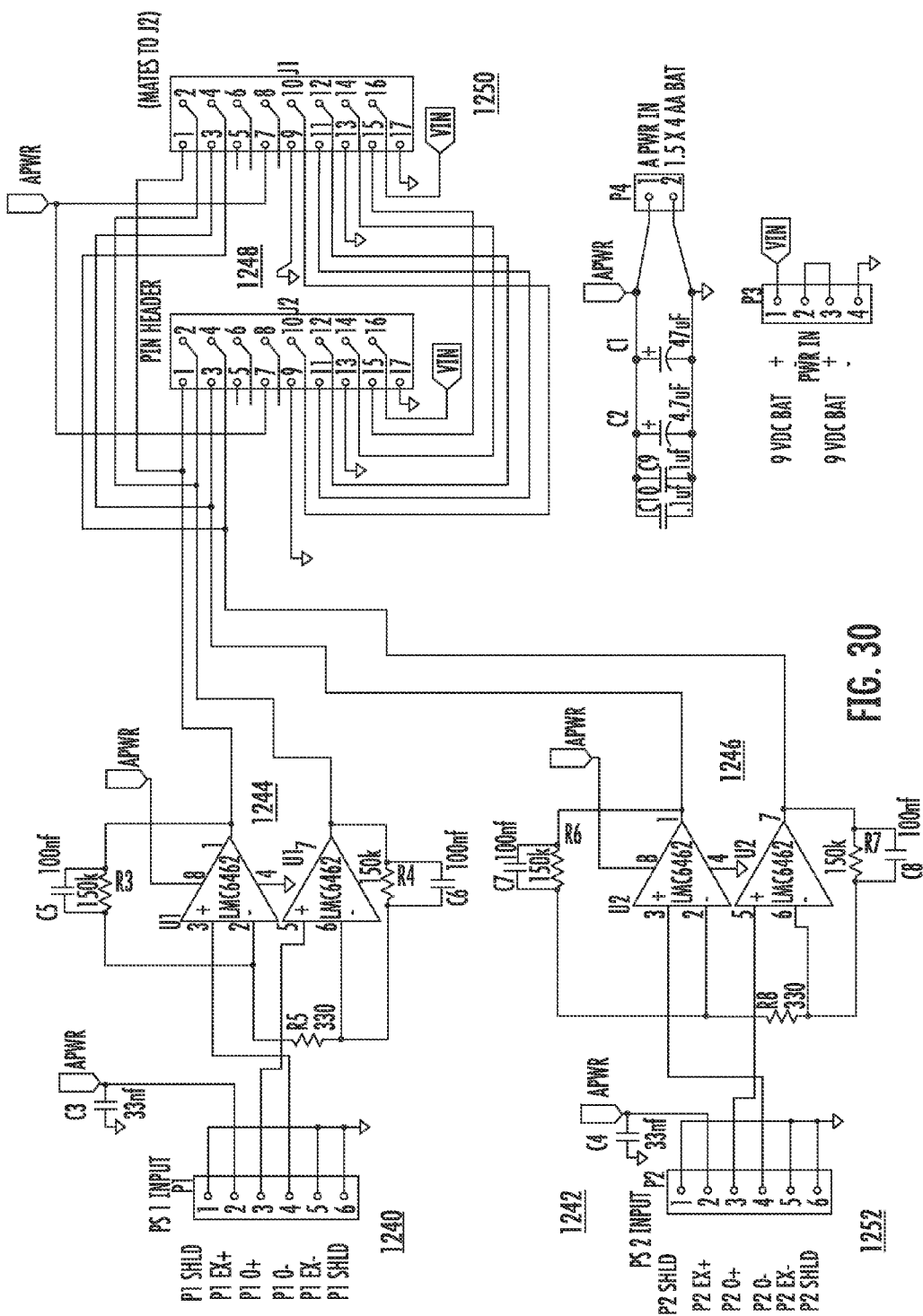
FIG. 30 is a schematic circuit diagram of a representative example of the pressure converter circuit as shown in FIG. 27 that can be used in accordance with a non-limiting example.

FIG. 30 is a schematic circuit diagram of the pressure converter 1252 in accordance with a non-limiting example and showing the various pressure sensor 1 input 1240 and pressure sensor 2 input 1242. These are independent channels each with comparators and operational amplifiers illustrated generally at 1244 and 1246 respectively. These components and circuits connect into appropriate pin headers 1248 and 1250 that output to a single board computer in this non-limiting example.

These examples show use of the pressure sensor as a TDOC-4030 pressure sensor and a catheter as a TDOC-7F (7 French) catheter. The catheter as described below relative to FIG. 31 can be used in a non-limiting example for the measurement.

Different processors 1204 as a single board computer can be used in a non-limiting example. The described Rabbit microprocessor is a low-power, single-board computer and is especially operable with portable handheld, battery-powered, remote monitoring systems. It includes built-in analog and digital input/output and typically consumes less than 20 milliamperes when operational and less than 100 microamps in a power-save mode. In this non-limiting example, it includes flash memory and SRAM and various inputs/outputs and in one non-limiting example eight analog/digital converter inputs with programmable gain and six serial ports. It has pulse width modulation (PWM) outputs. It can be programmed using C software in a non-limiting example.

It should be understood that the display unit 1208 as illustrated in FIG. 27 is a separate display unit that includes the display, keyboard and light emitting diodes and supported on the housing, but could be incorporated integral with the single board computer in a non-limiting example.

Figure 31:
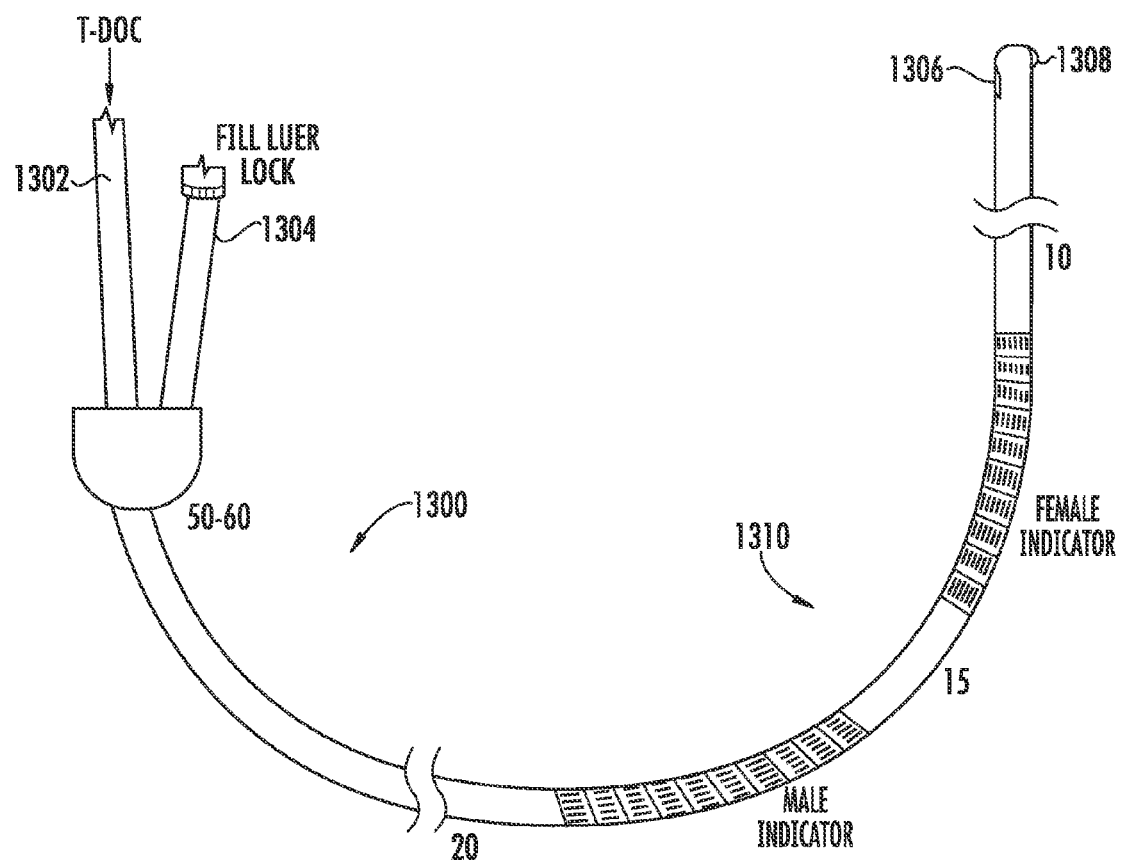
FIG. 31 is a simplified plan view of a catheter that can be used for the urodynamic and medical diagnostic testing in accordance with a non-limiting example.

FIG. 31 is an example catheter 1300 that can be used in accordance with a non-limiting example. It is a urodynamic dual lumen catheter formed from a catheter body as an elongated tube with proximal and distal ends and preferably has a smallest external diameter that can contain two lumens within it. It is typically approximately 50 to about 60 centimeters in length. A first lumen 1302 is used for monitoring bladder activity. In one non-limiting example, it contains a stylet/wire sensor that can be left within the lumen or used alone. A second lumen 1304 permits the filling port to instill fluid into the urinary bladder. The second lumen output is shown at 1306 and a sensor 1308 is positioned at the distal end. This catheter includes a luer lock end for rapid connection to infusion tubing or a syringe, and can accommodate rates of infusion up to 1,200 ml/hr via gravity flow or 15 ml/sec via manual installation. The external surface of the catheter has a surface area that contains areas of indicators along its length shown generally at 1310 that operate as a urine leak detect device. These indicators 1310 change color when exposed to two components in combination in accordance with a non-limiting example. This color change can occur with a temperature about 30 degrees Celsius and the presence of urea in a non-limiting example.

The catheter 1300 is used to evaluate bladder pressures at rest, empty or with urine, filling with fluid during voiding. It is used to evaluate for urinary incontinence by detecting a minimal amount of urine loss during voluntary and involuntary maneuvers of the type as described before. The stylet sensor in one non-limiting example is used alone for pressure monitoring while presenting the least amount of disruption/distortion of the urethra and urinary sphincters. The stylet in another non-limiting example is packaged separately and inserted into an existing Foley catheter to measure pressure and function in one non-limiting example.

In one non-limiting example, the catheter is a dual lumen six French catheter of about 50 centimeters and includes the sensor 1308 and fill port at the second lumen 1304. It is inserted in a non-limiting example about 10 centimeters for a female bladder and 15 centimeters for a male bladder. The location of color change indicators 1310 for a female could be about 11-14 centimeters, and for a male, about 16-19 centimeters. In one non-limiting example, the urine pH range is about 4.6 to about 8.

It should be understood that the catheter is preferably a smaller diameter catheter and includes those down to 3 (three) and 4 (four) French. The smallest catheter possible is used as a urethra catheter and somewhat smaller than a standard ten (10) French catheter. It has been found that some patients have a tendency to leak with the larger catheter in place because of the size of the catheter or they become obstructed with that catheter in place. Smaller urinary bladder catheters are typically about 6 (six) French and used for neonatal infants. There are some PICC catheters (Peripherally Inserted Central Catheters) that are three (3) and four (4) French. These smaller catheters should be double lumen in this example. This system is not limited in size, but the smaller is advantageous.

The double lumen catheter, in accordance with a non-limiting example as described, has the first lumen 1302 for a sensor probe 1308 and a second lumen 1304 for the filling with liquid. The sensor probe is a "T-doc" as used with an air-charged catheter for pressure sensing and air-charged pressure recording in one non-limiting example. It should be understood that this catheter can be used with or without filling the bladder, and advantageously used in urodynamic testing. The doctor, nurse or clinician does not have to personally bend down and view the urethra area to determine if there is leakage, which is an advantage in a clinical test. Different types of indicators 1310 as chemical indicators can be used.

Figure 32:
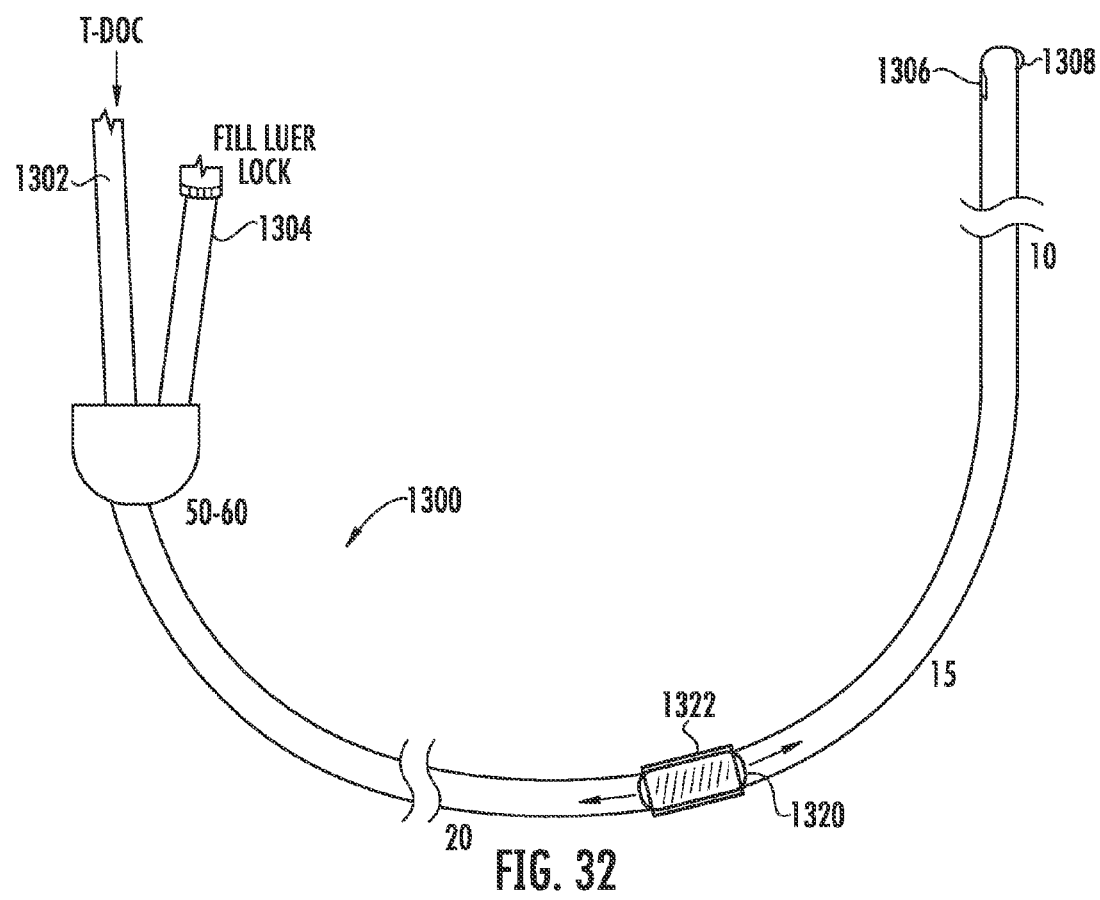
FIG. 32 is another simplified plain view of another example of a catheter similar to that shown in FIG. 31 that can be used for the urodynamic and medical diagnostic testing in accordance with a non-limiting example.

In another non-limiting example such as shown in FIG. 32, the catheter includes a support ring 1320 such as a silastic ring that holds a urine-indicating pad or other enzymatic pad 1322 and is affixed to the catheter as a single unit wherein the catheter that measures the intravesicular pressure. The silastic ring 1320 carries a color changing pad in this example instead of using color indicators 1310 positioned along the catheter surface as in the example of FIG. 31. This also provides for a urinary leakage indicator. The support ring 1320 slides on the catheter in one example. It is permanently affixed to the catheter, but adjustable in this example. A moisture indicating dye is used in an example on the pad 1322 positioned on the ring 1320. An example of a dye is disclosed in U.S. Pat. No. 4,327,731 as a moisture indicator, and in one aspect could be an enzyme catalyst.

Different types of pads or substrates could be used in combination with the support ring 1320 and moveable along the catheter. This combination catheter and the urine indicating sensor, in one example, are specific for use to determine an instance of stress urinary incontinence. It is possible, however, to add a balloon to this catheter similar to a Foley catheter such that the catheter remains in place. Two catheters are thus possible. For example, a specific catheter and urine indicator are used for stress urinary incontinence. It is also possible to add a balloon with the larger 14, 16, 18 or 20 French catheters as a larger size. A sensing system is included in this example. Added to this catheter is a channel for urine drainage, the sensor, and an indwelling balloon to keep it in place. The catheter, in one example, is used to determine whether the patient can protect their airway in conjunction with the involuntary reflex cough test (iRCT).

The cloth or pad 1322 is attached to the support ring 1320 and includes on the pad a regent that is permanently attached. It can be a single use catheter for stress urinary incontinence (SUI) testing. It is included within the test kit to be described in one example and includes the nebulizer (and the drug) for involuntary reflex cough testing as described before.

In one example, it is possible to have a catheter of about three (3), four (4), or five (5) or somewhat larger French that thread inside a regular Foley catheter with pressure measurement capability. The catheter that goes inside the urethra, such as a seven (7) French catheter, can go inside a Foley catheter. In one example, the balloon is part of the smaller catheter and measures or tests for airway protection in the technique as described before.

An enzymatic moisture detector can be used. Initially, any indicators or pad and ring could be covered before catheter use. When needed, the catheter is uncovered and moved into the proper position against the meatus. A first catheter is used with stress urinary incontinence and testing. Another catheter as a second or larger diameter catheter is balloon specific for reflex cough testing to measure intra-abdominal pressure in determination of airway protection.

In an example, temperature is used with the sensor and changes the sensor as an indicator. It is possible to use the presence of urea for sensing urine. One problem is in bladder testing. The bladder is often filled with saline water or other fluid that is not urine. If the indicator is specific to ammonia or urea, then it would not indicate adequately. Temperature is one advantageous solution and a material that is sensitive to temperature change of about 90 degrees is adequate. The fluid is inserted into the bladder and becomes warmer than room temperature. If there is leakage, it changes the color of the catheter even without the presence of urea.

The tip of the catheter can be placed into the urethra and the outside of the catheter includes the indicator. It changes color if there is leakage whether there is urine inside the bladder or just fill. It could change the color of liquid after it leaks. This could be an assurance against false positives such as would occur with perspiration from the doctor's or nurse's hands. If there is a second testing such as in surgery (and the patient hopefully fixed), a different color could be used. In SUI testing, the liquid is placed in the bladder in one example, but would come out a different color when it reacts with the sensor on the bladder near the meatus. This assures that one is viewing a leakage and not a false positive.

There is a possibility for measuring airway using the port in combination. The catheter can be small enough to go into a side port of a Foley catheter similar to a guide wire. Thus it is possible to take the catheter out if it is obstructing in some way and leave a guide wire. It is possible to remove the catheter and still have a guide wire or small catheter that has a sensor probe on the end. Instead of having a dual channel and having a tube inside a tube that you could do a fill around, it is possible to remove the outside tube that is blocking the urethra. It should be understood that the catheter (depending on size and pathophysiology of a patient) can either block the urethra or hold the urethra open, causing additional leakage. Specific catheter designs as described alleviate these problems. With the larger catheters, the larger catheter size is used to fill and is taken out. The inside tube (catheter) stays. A smaller four (4) French catheter has a dual channel, one for the pressure sensor and the other to fill 1200 millimeters an hour and is adequate to cover different possibilities.

Figure 33:
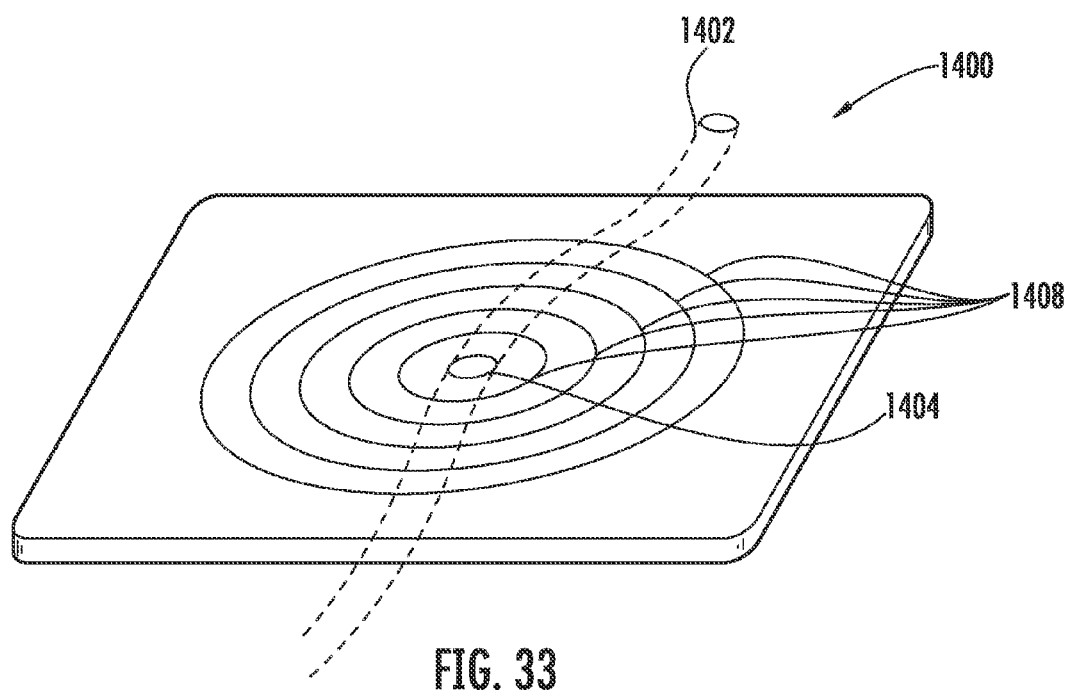
FIG. 33 is an example of a urinary incontinence pad that can be used with a urodynamic catheter and showing pad areas that indicate color change for leakage.

FIG. 33 shows an embodiment of a color changing urinary pad 1204 that can be used with a catheter such as described before. The color changing urinary incontinence pad 1400 is used in conjunction with a catheter 1402 and has a small relief cut-out (hole) 1404 in the middle of the pad where the catheter enters. The pad is placed against the underside near the urethra of a female typically and the catheter enters the urethra and extends through the hole in the center of the urinary incontinence pad for fluid flow and testing purposes. The pad could be taped to the underside in the crotch area. For example, when the involuntary reflex cough test is given and the catheter is inserted through the urethra, the patient is prone to leak urine in some examples. This pad includes concentric rings 1408 around the center catheter cut-out at preferred 10 millimeter intervals for a target area of 50 millimeters. In one non-limiting example, a nitrogen-ammonia (NH3) region is used to identify positively the presence of urine on the pad. The target intervals of 10 millimeters each are used to determine how much leakage and incontinence occurs during, for example, a reflex or involuntary cough test as described before. The different concentric areas have different amounts of reagent in a non-limiting example or different reagents to allow different color changes at the spaced intervals depending on the amount of urine leakage.

Figure 34:
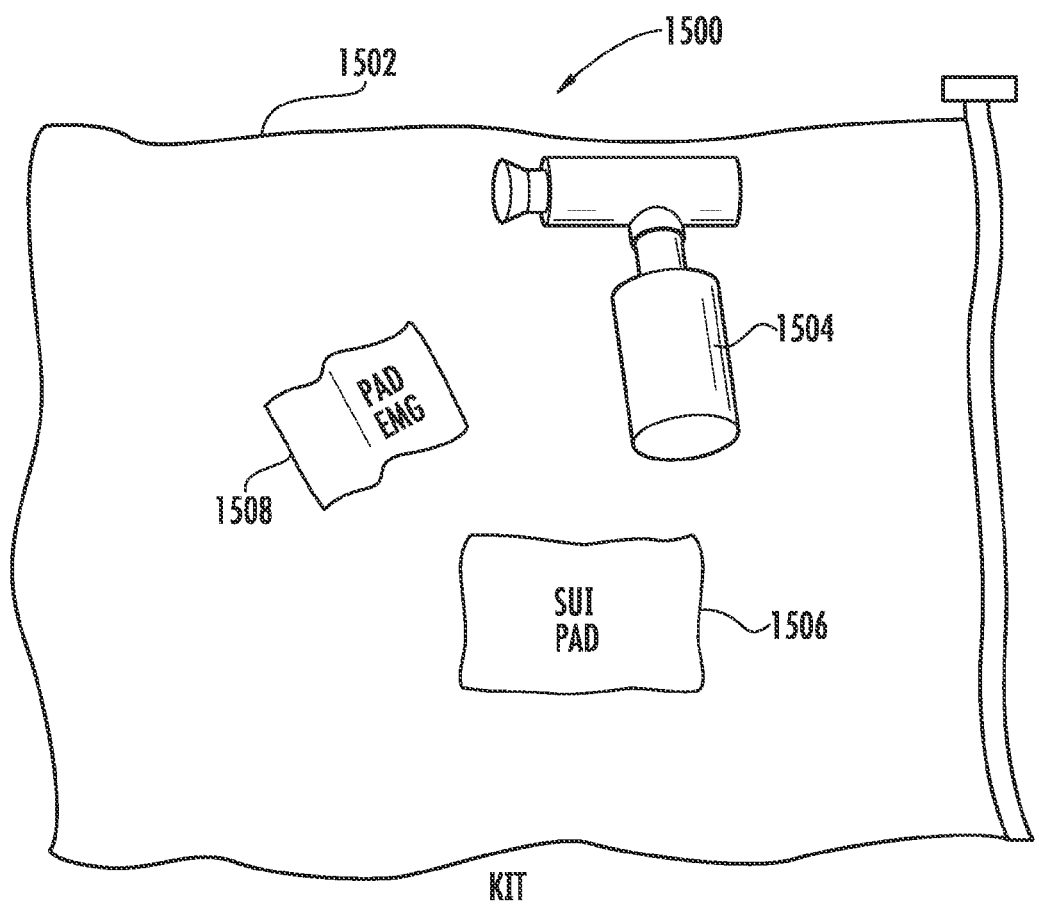
FIGS. 34 and 35 are fragmental drawing views showing examples of kits that can be used in accordance with a non-limiting example.
Figure 35:
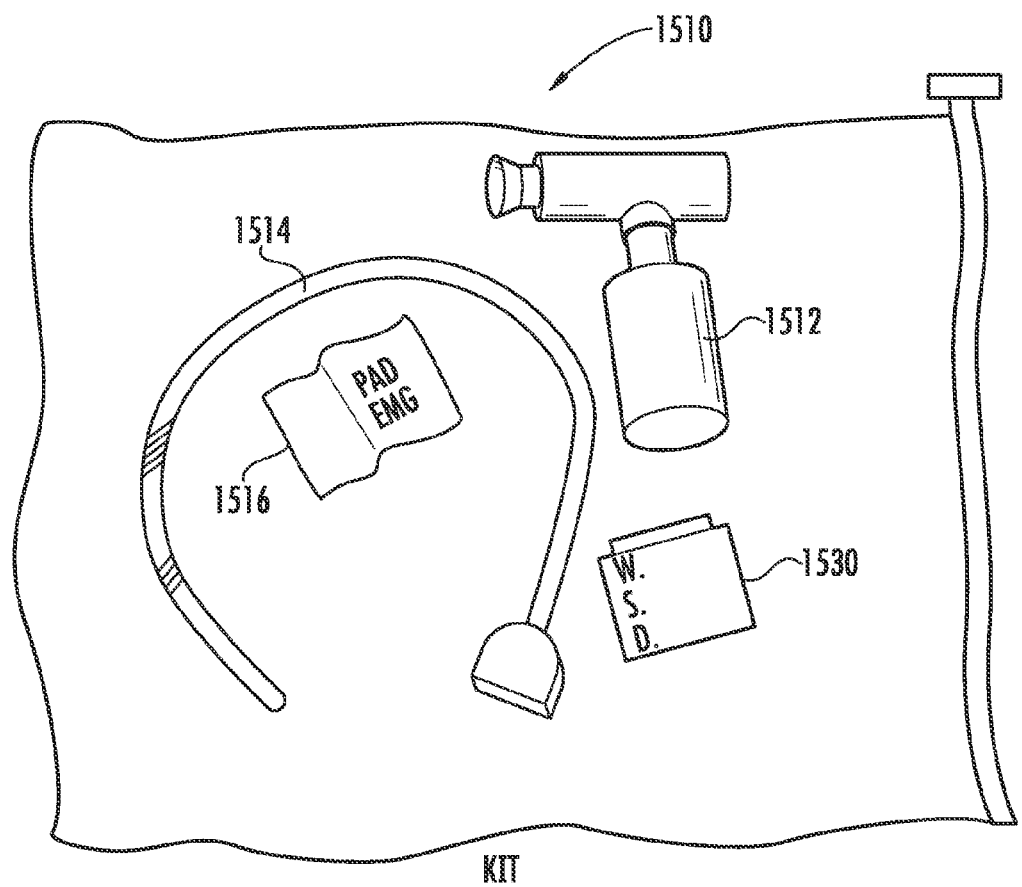

FIGS. 34 and 35 show example kits that can be used in accordance with a non-limiting example. A first kit 1500 shown in FIG. 34 includes a package or housing 1502 or other housing that holds the kit component. A nebulizer 1504 includes the drug for the tartaric acid and a urinary incontinence pad 1506 and an EMG pad 1508 to be placed at paraspinal. A second kit 1510 is shown in FIG. 35 and includes the nebulizer 1512 and a catheter 1514 such as described relative to FIG. 31, although different types of catheters can be used. An EMG pad 1516 is illustrated. The kits are contained in self-contained housings or packages 1502 with a quick-release. The various components as described are throw away components, except the processing device. The kit could include any necessary connector leads that connect into the handheld device.

Any catheter could include a wireless sensing device 1530 that is included in the kit in case wireless technology is used. Although a wireless sensing device could be separately connected to the catheter after the kit is opened, in one aspect, it is possible to include the wireless sensing device connected to any appropriate catheter such that the kit is open, the nebulizer removed, any pad and the catheter with wireless sensing device. The handheld device can be a separate device and the catheter used and wireless signals sent to the handheld device. After analysis and testing on a patient, the kit components such as the catheter and wireless sensing device, pads and nebulizer could be disposed of in the proper manner. It is possible that the EMG pads could connect into the wireless sensing device such that wireless signals are transmitted to the handheld device that includes the pressure readings and the EMG signals. Thus, the kit or system when removed would include the pressure sensing device with the attached leads and EMG pad and catheter that may be integrated together or separately removed and then connected to each other.

This application is related to copending patent application entitled, "INVOLUNTARY CONTRACTION INDUCED PRESSURE AS A MEDICAL DIAGNOSTIC TOOL USING INVOLUNTARY REFLEX COUGH TEST," which is filed on the same date and by the same assignee and inventors, the disclosure which is hereby incorporated by reference.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method of evaluating a patient for stress urinary incontinence, comprising:
   inducing an involuntary reflex cough event within the patient that activates the nucleus ambiguous and medial motor cell column of the patient and stimulates involuntary cough activated paraspinal muscles in the pelvis of the patient;
   obtaining an electromyogram (EMG) from the involuntary cough activated paraspinal muscles while inducing the involuntary reflex cough event and determining its duration;
   identifying any urine leakage time that occurs during the involuntary reflex cough event and correlating within a processor the urine leakage time with the EMG data received from the involuntary cough activated paraspinal muscles and duration of the cough event to determine stress urinary incontinence.

2. The method according to claim 1 and further comprising obtaining the EMG from the L5/S1 paraspinal muscles.

3. The method according to claim 1 and further comprising having the patient produce a voluntary cough before inducing an involuntary cough.

4. The method according to claim 3 and further comprising obtaining an EMG and identifying any urine leakage time during the voluntary cough and correlating any urine leakage time with the urine leakage time obtained during the involuntary reflex cough event.

5. The method according to claim 1 and further comprising determining the intra-abdominal pressure (IAP) during the involuntary reflex cough event and correlating the IAP with the duration of the involuntary reflex cough event and urine leakage time.

6. The method according to claim 5 and further comprising determining the peak IAP and correlating it with the IAP and duration of the involuntary reflex cough event.

7. The method according to claim 6 and further comprising determining average IAP and correlating it with the peak IAP and duration of the involuntary reflex cough event.

8. The method according to claim 7 and further comprising determining an area under the curve corresponding to IAP samples obtained during the involuntary reflex cough event and correlating it with the IAP and duration of the involuntary reflex cough event.

9. A method of evaluating a patient for stress urinary incontinence, comprising:
   having the patient produce a voluntary cough and identifying any urine leakage time during the voluntary cough;
   inducing an involuntary reflex cough event within the patient that activates the nucleus ambiguous and medial motor cell column of the patient and stimulates involuntary cough activated paraspinal muscles in the pelvis of the patient;
   obtaining an electromyogram (EMG) from the involuntary cough activated paraspinal muscles while inducing the involuntary reflex cough event; and
   identifying any urine leakage time that occurs during the involuntary reflex cough event and determining the cough event duration correlating within a processor the EMG data received from the involuntary cough activated paraspinal muscles urine leakage time for both the voluntary cough and involuntary cough event and their duration and cough event duration to determine stress urinary incontinence.

10. The method according to claim 9 and further comprising determining the intra-abdominal pressure (IAP) during the voluntary cough and involuntary reflex cough event and correlating the IAP with the duration of the involuntary reflex cough event and urine leakage time.

11. The method according to claim 10 and further comprising determining the peak IAP and correlating it with the IAP.

12. The method according to claim 11 and further comprising determining average IAP and correlating it with the peak IAP.

13. The method according to claim 12 and further comprising determining an area under the curve corresponding to IAP samples.

14. The method according to claim 9 and further comprising obtaining the EMG rom the L5/S1 paraspinal muscles.

15. A system for evaluating a patient for stress urinary incontinence, comprising:
a nebulizer containing an agent that induces an involuntary reflex cough event within the patient that activates the nucleus ambiguous and medial motor cell column of the patient and stimulates involuntary cough activated paraspinal muscles in the pelvis of the patient;
at least one electromyogram (EMG) pad configured to be attached to the lumbar region of the patient's back and obtain EMG signals from the involuntary cough activated paraspinal muscles;
a urine leak detect device configured to detect urine leakage; and
a processing device that receives the EMG data received from the involuntary cough activated paraspinal muscles and correlates the EMG data and duration of the involuntary reflex cough event with an urine leakage time to determine stress urinary incontinence.

16. The system according to claim 15 wherein said processing device comprises a portable handheld device comprising,
a housing configured for handheld use;
at least one interface carried by the housing and configured to receive the EMG and data related to urine leakage time; and
a processor carried by the housing and configured to correlate the EMG and duration of the involuntary reflex cough event and urine leakage time to determine stress urinary incontinence.

17. The system according to claim 15 wherein said at least one EMG pad is configured to obtain the EMG from the L5/S1 paraspinal muscles.

18. The system according to claim 15 a further comprising a catheter configured to fill the bladder with a fluid and measure the intra-abdominal pressure (IAP) during the involuntary reflex cough event.

19. The system according to claim 18 wherein said processing device is configured to determine the peak IAP and correlate it with the LAP and duration of the involuntary reflex cough event.

20. The system according to claim 19 wherein said processing device is configured to determine average IAP and correlate it with the peak IAP and duration of the involuntary reflex cough event.

21. The system according to claim 20 wherein said processing device is configured to calculate an area under the curve corresponding to IAP samples obtained during the involuntary reflex cough event and correlate it with the IAP and duration of the involuntary reflex cough event.

22. A device for evaluating a patient for stress urinary incontinence, comprising:
a housing configured for handheld use;
at least one interface carried by the housing and configured to receive an electromyogram (EMG) data from involuntary cough activated paraspinal muscles in the pelvis of the patient that had been activated by an involuntary reflex cough event that activates the nucleus ambiguous and medial motor cell column of the patient and data relating to an urine leakage time during the involuntary reflex cough test; and
a processor carried by the housing and configured to receive and process the EMG data received from the involuntary cough activated paraspinal muscles and urine leakage time and correlate the EMG data and data regarding the duration of the involuntary reflex cough event and urine leakage time to determine stress urinary incontinence.

23. The device according to claim 22 wherein said at least one interface is configured to receive pressure readings regarding intra-abdominal pressure (IAP) obtained during the involuntary cough reflex test, and said processor is configured to correlate the IAP with the EMG and urine leakage time and duration of the cough event to determine stress urinary incontinence.

24. The device according to claim 23 wherein said processor is configured to determine average IAP and peak IAP and correlate the average IAP with the peak IAP and duration of the involuntary cough reflex event.

25. The device according to claim 24 wherein said processor is configured to calculate an area under the curve corresponding to IAP samples obtained during the involuntary reflex cough event and correlate it with the IAP and duration of the involuntary reflex cough event.

* * * * *